(12) United States Patent
Ochiai et al.

(10) Patent No.: US 9,051,590 B2
(45) Date of Patent: Jun. 9, 2015

(54) ACETYL-COA CARBOXYLASE

(75) Inventors: Misa Ochiai, Osaka (JP); Eiji Sakuradani, Muko (JP); Sakayu Shimizu, Kyoto (JP); Jun Ogawa, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 416 days.

(21) Appl. No.: 13/254,512

(22) PCT Filed: Mar. 17, 2010

(86) PCT No.: PCT/JP2010/054582
§ 371 (c)(1),
(2), (4) Date: Sep. 2, 2011

(87) PCT Pub. No.: WO2010/107070
PCT Pub. Date: Sep. 23, 2010

(65) Prior Publication Data
US 2012/0264960 A1    Oct. 18, 2012

(30) Foreign Application Priority Data
Mar. 18, 2009  (JP) ................................ 2009-066147

(51) Int. Cl.
| C07H 21/02 | (2006.01) |
| C07H 21/04 | (2006.01) |
| C12Q 1/68 | (2006.01) |
| C12P 21/06 | (2006.01) |
| C12P 21/04 | (2006.01) |
| C12N 15/00 | (2006.01) |
| C12P 7/64 | (2006.01) |
| A23L 1/30 | (2006.01) |
| C12N 9/00 | (2006.01) |

(52) U.S. Cl.
CPC .............. *C12P 7/6427* (2013.01); *A23L 1/3006* (2013.01); *A23V 2002/00* (2013.01); *C12N 9/93* (2013.01); *C12Y 604/01002* (2013.01)

(58) Field of Classification Search
None
See application file for complete search history.

(56) References Cited

U.S. PATENT DOCUMENTS

2001/0053519 A1* 12/2001 Fodor et al. ....................... 435/6
2006/0094092 A1    5/2006 Damude et al.

OTHER PUBLICATIONS

Witkowski et al., Conversion of b-ketoacyl synthase to a Malonyl Decarboxylase by replacement of the active cysteine with glutamine. Biochemistry, 1999, vol. 38:11643-11650.*
Broun et al., Catalytic plasticity of fatty acid modification enzymes underlying chemical diversity of plant lipids. Science, 1998, vol. 282: 1315-1317.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
GenBank (Accession EF397565 GI: 146400062 Nov. 1, 2008).*
Database UniProt [Online] Jul. 5, 2004 "SubName: Full=Acetyl-CoA carboxylase; EC=6.4.1.2; Flags: Fragment;", retrieved from EBI accession No. UniProt:Q70BT2, Database Accession No. Q70BT2.
Extended European Search Report for EP Application No. 10753561.9, dated Dec. 5, 2012.
Ruenwai et al., "Overexpression of acetyl-CoA carboxylase gene of *Mucor rouxii* enhanced fatty acid content in *Hansenula polymorpha*" Molecular Biotechnology 42(3):327-32, published online Mar. 5, 2009.
"Mortierella alpine partial acc1 gene for acetyl-CoA carboxylase, exons 1-2", NCBI Sequence Revision History [online]; Accession: AJ586915, http://www.ncbi.nlm.nih.gov/sviewer/viewer.fcgi?46517881:EMBL:10650764 Nov. 14, 2006 uploaded, [retrieved on Apr. 23, 2010].
Wynn et al., "The role of malic enzyme in the regulation of lipid accumulation in filamentous fungi" Microbiology 145:1911-17, 1999.
International Search Report for PCT/JP2010/054582, mailed May 11, 2010.
Russian Office Action issued with respect to Russian Patent App. 2011142010, dated Mar. 20, 2014.

* cited by examiner

*Primary Examiner* — Amanda Haney
(74) *Attorney, Agent, or Firm* — Greenblum & Bernstein, P.L.C.

(57) ABSTRACT

The present invention provides a novel acetyl-CoA carboxylase.
The object of the present invention is attained by the nucleotide sequence of SEQ ID NO: 1 and the amino acid sequence of SEQ ID NO: 2 of the present invention.

6 Claims, 18 Drawing Sheets

Figure 1A

```
   1  TCCCACTGAC TCAAGCGGAA CTTCCAAGCA ACCATAATCC CATCATGACT ACCAACGTAC AGTCCTTCAT TGGAGGAAAC GCATTAGAGA ACGCCCCTGC
                                                              M  T  T  N  V  Q  S  F  I   G  G  N   A  L  E  N   A  P  A·

101  TGGAGCTGTC CGCGAGTTTG TTAACCAGCA TGGAGGCCAC AGCCGTGATCA CCAAGATCCT GATCGCCAAC AACGGTATTG CGGCCGTCAA GGAGATCCGA
      ·G  A  V   R  E  F  V   N  Q  H   G  G  H   S  V  I  T   K  I  L   I  A  N   N  G  I  A   A  V  K   E  I  R

201  TCTGTCCGCA AGTGGGCGTA CGAGACCTTT GGAGATGAGC GTGCGATCCA GTTCACGGTC ATGGCTACGC CAGAGGATCT GAAGATCAAT GCTGAATATA
      S  V  R  K   W  A  Y   E  T  F   G  D  E  R   A  I  Q   F  T  V   M  A  T  P   E  D  L   K  I  N   A  E  Y  I

301  TCCGCATGGC CGACCAGTAT GTCGAAGTAC CGGGAGGATC CAACAACAAC AACTACGCCA ACGTTGACCT CATTGTCGAC ATTGCCGAAC GCACCGGCGT
      ·R  M  A   D  Q  Y   V  E  V  P   G  G  S   N  N  N   N  Y  A  N   V  D  L   I  V  D   I  A  E  R   T  G  V·

401  CCATGCTGTG TGGGCTGGAT GGGGACATGC CTCGGAGAAC CCCAAACTCC CAGAGTCTCT TCGCGACAGC CCTCAAAAGA TCATCTTCAT CGGACCCCCC
      ·H  A  V   W  A  G  W   G  H  A   S  E  N   P  K  L  P   E  S  L   R  D  S   P  Q  K  I   I  F  I   G  P  P

501  GGCTCCGCCA TGCGCTCGTT GGGTGACAAG ATCTCGTCCA CGATCGTCGC TCAATCGGCC GACGTCCCTA CGATGGGCTG GTCCGGAACT GGCATCACAG
      G  S  A  M   R  S  L   G  D  K   I  S  S  T   I  V  A   Q  S  A   D  V  P  T   M  G  W   S  G  T   G  I  T  E

601  AGACTACCAT GGATGCTAAT GGTTTCGTCA TGGTGCCCGA GGATGCTTAC CAGGCTGCCT GTGTCACCGA TGCAGAGGAT GGTCTTCAGA AGCCCCACAC
      ·T  T  M   D  A  N   G  F  V  M   V  P  E   D  A  Y   Q  A  A  C   V  T  D   A  E  D   G  L  Q  K   A  H  T·

701  CATCGGCTTC CCGGTCATGA TCAAGGCTTC AGAGGGTGGT GGAGGAAAGG GTATTCGTAA GGTTGAGGAA CCAGAAAAGT TCGCTCAGGC CTTCAACCAG
      ·I  G  F   P  V  M  I   K  A  S   E  G  G   G  G  K  G   I  R  K   V  E  E   P  E  K  F   A  Q  A   F  N  Q

801  GTTTTGGGCG AGGTCCCCGG TTCCCCCGTC TTCATCATGA AGTTGGCTGG TAACGCGCGC CATCTGGAGG TCCAGCTTTT GGCCGATCAG TATGGAAATG
      V  L  G  E   V  P  G   S  P  V   F  I  M  K   L  A  G   N  A  R   H  L  E  V   Q  L  L   A  D  Q   Y  G  N  A

901  CCATCTCGCT CTTTGGACGC GATTGCTCTG TCCAGCGTCG CCATCAGAAG ATTATTGAGG AAGCTCCCGT CACCATTGCC AAGCCCGACA CCTTCGAGTC
      ·I  S  L   F  G  R   D  C  S  V   Q  R  R   H  Q  K   I  I  E  E   A  P  V   T  I  A   K  P  D  T   F  E  S·

1001  GATGGAGAAG GCTGCAGTGC GTCTGGCCAA GTTGGTCGGA TACGTTTCTG CAGGTACCGT CGAGTACCTG TACTCGCACT CGACTGACAC CTTCTTCTTC
      M  E  K   A  A  V  R   L  A  K   L  V  G   Y  V  S  A   G  T  V   E  Y  L   Y  S  H  S   T  D  T   F  F  F

1101  CTGGAGTTGA ACCCCAGACT TCAGGTCGAG CATCCTACCA CCGAGATGGT CTCAGGTGTC AACCTGCCAG CTGCTCAGCT CCAGATCGCC ATGGGTCTTC
      L  E  L  N   P  R  L   Q  V  E   H  P  T  T   E  M  V   S  G  V   N  L  P  A   A  Q  L   Q  I  A   M  G  L  P

1201  CTTTGAACCG CATCAAGGAC ATCCGTGTTC TCTATGGTCT TCAACCCACA GGAACGTCCG AGATCGACTT TGAGTTTTCA CAGCAGATCT CGTATGAGAC
      ·L  N  R   I  K  D   I  R  V  L   Y  G  L   Q  P  T   G  T  S  E   I  D  F   E  F  S   Q  Q  I  S   Y  E  T·

1301  TCAGCGCAAG CCCGCCCCTA AGGGACACGT CATTGCTGTC CGTATCACAG CCGAGAACCC CGATGCAGGA TTCAAGCCCT CAAGCGGAAT GATGCAGGAA
      Q  R  K   P  A  P  K   G  H  V   I  A  V   R  I  T  A   E  N  P   D  A  G   F  K  P  S   S  G  M   M  Q  E

1401  CTCAATTTCA GATCATCTAC CAACGTCTGG GGCTACTTCT CTGTCAACTC TGCAGGAGGA CTGCACGAGT TTGCCGATTC TCAGTTTGGT CATATCTTTG
      L  N  F  R   S  S  T   N  V  W   G  Y  F  S   V  N  S   A  G  G   L  H  E  F   A  D  S   Q  F  G   H  I  F  A

1501  CCTATGGACA GGATCGTGGT CAGTCTAGAA AGAACATGGT CGTTGCCCTC AAGGAACTCT CCATTCGTGG TGATTTCCGC ACTACGGTCG AGTACTTGAT
      ·Y  G  Q   D  R  G   Q  S  R  K   N  M  V   V  A  L   K  E  L  S   I  R  G   D  F  R   T  T  V  E   Y  L  I·

1601  CCGCCTTTTG GAGACACAGG AGTTCGAGGA AAACACCATT AACACTGGCT GGCTCGACAG CTTGATCTCC AACAACCTCA CTGCTGAACG CCCTGAGACC
      ·R  L  L   E  T  Q  E   F  E  E   N  T  I   N  T  G  W   L  D  S   L  I  S   N  N  L  T   A  E  R   P  E  T

1701  ATGTTGGCTG TCATGTGTGG TGCTGTTAAC AGAGCCCACA CCATCTCCGA GAACTGCATT AAGGAGTACA AGAAGTCGCT GGAGAAGGGT CAAGTGCCTA
      M  L  A  V   M  C  G   A  V  N   R  A  H  T   I  S  E   N  C  I   K  E  Y  K   K  S  L   E  K  G   Q  V  P  S

1801  GCAAGGACGT TCTGCGCTCG GTCAACCAGC TTGACTTTAT TTACGACGGC GTCCGCTACA ACTTCACCGC CACTCGCTCT GGACCCAACT CGTACACTCT
      ·K  D  V   L  R  S   V  N  Q  L   D  F  I   Y  D  G   V  R  Y  N   F  T  A   T  R  S   G  P  N  S   Y  T  L·

1901  GTACTTGAAT GGATCCATGA TCTCCATCTC TGTCCGTCCA TTGACCGATG GCGGTCTCTT GGTCCTTTTG GATGGCAAGG CTCACACGAC TTACTCGTTG
      ·Y  L  N   G  S  M  I   S  I  S   V  R  P   L  T  D  G   G  L  L   V  L  L   D  G  K  A   H  T  T   Y  S  L

2001  GAAGAGGTCC AGGCCACTCG CCTGATGGTC GATGGAAAGA CTTGTTTGTT GGAGAAGGAG AACGACCCTA CTCAACTCCG CTCCCCCTCC CCAGGCAAAC
      E  E  V  Q   A  T  R   L  M  V   D  G  K  T   C  L  L   E  K  E   N  D  P  T   Q  L  R   S  P  S   P  G  K  L
```

Figure 1B

```
2101    TTGTTCGCTA CCTTGTCGAG TCTGGCGACC ATGTTACGGC CAGCCAGGCC TATGCTGAGA TTGAGGTCAT GAAGATGTAT ATGCCCTTGA TCGCCACCGA
         V  R  Y   L  V  E    S  G  D  H   V  T  A   S  Q  A    Y  A  E  I   E  V  M    K  M  Y    M  P  L  I   A  T  E

2201    GGACGGTATT GTGCAGTTCA TCAAGCAACC CGGCACCACT CTGGATGCTG GTGATATCAT TGGTATCCTC AGCTTGGACG ATCCCTCCCG CGTTCGCCAC
         D  G  I   V  Q  F  I   K  Q  P   G  T  T    L  D  A  G   D  I  I   G  I  L    S  L  D  D   P  S  R    V  R  H

2301    GCTAAGCCCT TCGAAGGTCA GCTCCCTCCC ATGGGTCAGC CACCATTCA CGGAGCTAAG CCCCATCAGC GTTACCGCGA GCTGCGACTC GTCCTCGACA
         A  K  P  F   E  G  Q   L  P  P   M  G  Q  P   T  I  H   G  A  K    P  H  Q  R   Y  R  E    L  R  L    V  L  D  N

2401    ATGCCATGGA TGGCTACGAT AACCAGGCTT TGGTCCAGCC TACGCTGAAG GAGATCTTTG AGGTCCTCCA GACCCCGGAG CTGCCCTACT TGGAATTCAA
         M  D   G  Y  D    N  Q  A  L    V  Q  P    T  L  K    E  I  F  E   V  L  Q    T  P  E    L  P  Y  L   E  F  N

2501    CGAGGTCTTT GCTTCGCTAA GCGGAAGAAT CCCACCCAAG CTGGAAATTG CCCTGCACCA GGAGGTGGAT CAGTCCATGA AGAACCACGA GCACTTCCCC
         E  V  F   A  S  L  S   G  R  I   P  P  K    L  E  I  A   L  H  Q   E  V  D    Q  S  M  K   N  H  E    H  F  P

2601    GCTCGTACTC TTCAGGCCCT GATTGACTCG CACTGCCGCG CCAACTTCTC CAAGGCCGCC GATATCAATG CGTTCCAAGC CTCGGTGGGA CCTCTGACCG
         A  R  T  L   Q  A  L   I  D  S   H  C  R  A   N  F  S   K  A  A    D  I  N  A   F  Q  A    S  V  G    P  L  T  A

2701    CCATCATCAA GGAGTACCAA CACGGTTTGA AAACTCACTC CTGGGGCTTC ATTGCTGATT ACCTCAACAA GTACCATGAA GTCGAGTCGC TCTTTGATGA
         I  K   E  Y  Q    H  G  L  K    T  H  S    W  G  F    I  A  D  Y   L  N  K    Y  H  E    V  E  S  L   F  D  D

2801    CTCTGCTCGT GAGGAAGAGA TCTTCCTGTC CCTGCGTGAT CAGAACAAGG ACGACGTCGA GAAGGTCATC CGCATCGCAC TCTCGCACTC GCGTGTCACT
         S  A  R   E  E  E  I   F  L  S   L  R  D    Q  N  K  D   D  V  E   K  V  I    R  I  A  L   S  H  S    R  V  T

2901    GCCAAGAACA ACTTGGTTTT GACCCTTCTT GACCAGATCA AACCTACGGC CTCTGGAGGA GCGCTCGACA AGTTCTTCTC GCCTGTGCTC AAGAAGCTGG
         A  K  N  N   L  V  L   T  L  L   D  Q  I  K   P  T  A   S  G  G    A  L  D  K   F  F  S    P  V  L    K  K  L  A

3001    CTGAGCTTAC TGGCCGTCTC ACCGCCAAGG TCTCGCTCAA GGCCAGAGAG CTCCTTATTC ATGTTCAGTT GCCCAGCTTT GAGGAACGCC AGTCGCAGAT
         E  L  T   G  R  L    T  A  K  V   S  L  K   A  R  E    L  L  I  H   V  Q  L   P  S  F    E  E  R  Q   S  Q  M

3101    GGAGAAGATC CTCCGCTCGA GCGTCACTGA GGAGGTTTAT GGTGGTGAAC ACGAGGCCCG CATGCCTGCC TTTGAGAACA TCAAGGAGTT GGTCGACACC
         E  K  I   L  R  S  S   V  T  E   E  V  Y    G  G  E  H   E  A  R   M  P  A    F  E  N  I   K  E  L    V  D  T

3201    ACCTACACAG TCTTTGATGT CTTGCCTAAC TTCTTTTACC ATGAGTCGTT GCATGTCCGC ATTGCCGCGT TCGAGGTGTA CTGCCGTCGT GCCTACCATG
         T  Y  T  V   F  D  V   L  P  N   F  F  Y  H   E  S  L   H  V  R    I  A  A  F   E  V  Y    C  R  R    A  Y  H  A

3301    CGTACGAGAT TTTGGACATC AATTACCACA TGGAGCACCA GCCCTTGCTG ATCACTTGGA AGTTCTTGCT CAACACCCCC AACAAGTCCG AGTCTGGTCC
         Y   E  I   L  D  I    N  Y  H  M   E  H  Q   P  L  L    I  T  W  K   F  L  L   N  T  P    N  K  S  E   S  G  P

3401    CAACCGTGTG GCTAGTGTCA GTGACATGAG TTACTTGATC AACAAGGCTG ACCCTGAGCC TGTTCGTACC GGTGCCATTC TTGCCGTTCG CGACGTGAAG
         N  R  V   A  S  V  S   D  M  S   Y  L  I    N  K  A  D   P  E  P   V  R  T    G  A  I  L   A  V  R    D  V  K

3501    GAGCTGGAGG ACAGATTCGA GAGCATCCTC AACTTCTTCC CCTCTCACAA GTCGAACAAG CACTTGAGCC ATCTCGCTGC CGCCAGCGTC CACAACAATG
         E  L  E  D   R  F  E   S  I  L   N  F  F  P   S  H  K   S  N  K    H  L  S  H   L  A  A    A  S  V    H  N  N  V

3601    TGTTGAACGT TGTCATCAAG TCCGAGTCGG TTCACCCCAA CGATGATGAC TACTGGCTGA ACCTCCTCAG CCCCATCGTG AAGGGCGAGA CCGAGCGCCT
         L  N  V   V  I  K   S  E  S  V   H  P  N    D  D  D    Y  W  L  N   L  L  S    P  I  V    K  G  E  T   E  R  L

3701    TCGCTCGCAC GGCATCCGTC GCATGACCTT CTTGATCTTC CGTCAGGGCA ACTACCCCTC GTACTTCACC TTCCGTGAGC GTAACAACTA CGCTGAGGAT
         R  S  H   G  I  R  R   M  T  F   L  I  F    R  Q  G  N   Y  P  S   Y  F  T    F  R  E  R   N  N  Y    A  E  D

3801    CAGACCATCC GTCACATCGA GCCCGCCATG GCATACCGTC TTGAGTTGGC GCGCTTGTCC AACTTTGACA TCAAGCCCTG CTTCATTGAC AATCGCCAGG
         Q  T  I  R   H  I  E   P  A  M   A  Y  R  L   E  L  A   R  L  S    N  F  D  I   K  P  C    F  I  D    N  R  Q  V

3901    TTCATGTGTA CTATGCTGTG GGCAAGGAGA ACATTTCGGA CTGCCGCTTC TTTGTCTGCG CCTTGGTTCG TCCTGGTCGC CTGCGCTCTA GCGTTCGTAC
         H  V  Y   Y  A  V    G  K  E  N   I  S  D   C  R  F    F  V  C  A   L  V  R   P  G  R    L  R  S  S   V  R  T

4001    GGCGGATTAC TTGATTTCGG AGACCGACCG TCTGTTGAAC GATATTCTGG ATGCTCTGGA GATTGTGGGT GCCACCTACA AGCAGAGTGA CTGCAACCAC
         A  D  Y   L  I  S  E   T  D  R   L  L  N    D  I  L  D   A  L  E   I  V  G    A  T  Y  K   Q  S  D    C  N  H

4101    TTGTTTATCA ACTTCATCCC CACTTTCCAG TTGGACGCTA CCGAGGTTGA GACTGCCCTC AAGGGATTCA TTGACCGCCA CGGCAAGCGT CTCTGGCGTC
         L  F  I  N   F  I  P   T  F  Q   L  D  A  T   E  V  E   T  A  L    K  G  F  I   D  R  H    G  K  R    L  W  R  L
```

Figure 1C

```
4201    TTCGCGTCAC TGGCGCTGAG ATTCGCTTCA ATGTTCAGTC CAAGTCTGCG AATGGCGTTG AGGCCGACCC CGTTCCTCTT CGATTCATCA TCTCCAACGT
        ·R  V  T   G  A  E    I  R  F  N    V  Q  S     K  S  A    N  G  V  E    A  D  P     V  P  L   R  F  I  I   S  N  V·

4301    CTCTGGATAT GTCTTGAACG TCGACACCTA CCGCGAGGTT CAGACCGAGA AGGGTGCCAT CTTCAAGTCG GTTGGTCCTA CCGGTCCCTT CCATCTCTTG
        ·S  G  Y   V  L  N  V   D  T  Y   R  E  V     Q  T  E  K    G  A  I     F  K  S     V  G  P  T   G  P  F    H  L  L

4401    CCTGTGAACC AGCCCTACCC CACAAAGGAG TGGCTTCAGC CAGACGTTA CAAGGCACAC TTGATGGGCA CGACTTACGT CTATGACTTT GGCGAGCTCT
        P  V  N  Q   P  Y  P    T  K  E   W  L  Q  P   R  R  Y    K  A  H    L  M  G  T   T  Y  V    Y  D  F    G  E  L  F

4501    TCCGCCAGGC CGTCCGTGCT CAGTGGAACC ATGCCATCAA GCAGAACTCT TCGCTCAAGG TCCCATCCCA GGTCTGGAG ATGCGCGAGC TGGTCTTGGA
        ·R  Q  A   V  R  A    Q  W  N  H    A  I  K    Q  N  S    S  L  K  V    P  S  Q    V  L  E    M  R  E  L   V  L  D·

4601    TGAGAGACAG CAGTTGCAGC AGGTCGTTCG CGATGCCGGT TCCAACAACT GCGGCATGGT TGCCTGGATT TTCACTCTCC GTACCCCCGA GTACCCCGAG
        E  R  Q    Q  L  Q  Q    V  V  R   D  A  G     S  N  N  C   G  M  V    A  W  I    F  T  L  R    T  P  E    Y  P  E

4701    GGTCGACAGA TCATTGTCAT TGCCAACGAT ATCACCTTCA ACATTGGATC GTTTGGACCC GAGGAGGACC TGGTCTTCTA CAAGGCGTCC GAGATGGCCA
        G  R  Q  I   I  V  I    A  N  D    I  T  F  N    I  G  S    F  G  P    E  E  D     L  V  F  Y    K  A  S    E  M  A  R

4801    GAAAGTTGGG CATTCCCCGT GTTTACCTCT CTGCCAACTC TGGTGCCCGC ATTGGTCTTG CTAGTCAAGT GATTGGTCTC TTCAACTCTT GCTGGAACGA
        ·K  L  G    I  P  R    V  Y  L  S    A  N  S    G  A  R    I  G  L    A  S  E  V    I  G  L    F  N  S  C    W  N  D·

4901    CGCTTCCAAC CCCTCCAAGG GCTTCAAGTA CATCTACCTC ACGGACGCTG GACTGAAGCA GTTGGAGGCT CAGGAGGAGC GCTCTGGTAA GAAGAGCGTC
        ·A  S  N    P  S  K  G   F  K  Y     I  Y  L    T  D  A  G    L  K  Q     L  E  A    Q  E  E  R    S  G  K    K  S  V

5001    ATCACAGAGA CCATTGTTGA GGATGGCGAG ACCCGCCATA AGATCACGGA TGTCATCGGT GCTGTCGACG GTCTTGGTGT TGAGAACTTG CGCGGAAGTG
        I  T  E  T    I  V  E   D  G  E     T  R  H  K    I  T  D    V  I  G    A  V  D  G    L  G  V    E  N  L    R  G  S  G

5101    GTCTGATTGC TGGAGAGACC TCGCGAGCCT ACGACGACAT CTTTACCATT ACTTTGGTCA CCTGCCGCTC TGTTGGTATC GGTGCGTACT TGGTTCGTTT
        ·L  I  A   G  E  T    S  R  A  Y    D  D  I    F  T  I    T  L  V  T    C  R  S    V  G  I    G  A  Y  L    V  R  L·

5201    GGGTCAGCGT ACTATTCAGA ATGAGGGCCA GCCCATCATT TTGACTGGTG CCCCTGCCCT CAACAAGTTG CTTGGTCGCG ATGTCTACAC CTCGAACTTG
        G  Q  R    T  I  Q  N    E  G  Q    P  I  I    L  T  G  A    P  A  L    N  K  L    L  G  R  D    V  Y  T    S  N  L

5301    CAGCTCGGAG GCACTCAGAT TATGTACAAG AACGGAGTGT CGCACTTGAC CGCTCAGAAC GACTATGAGG GTATTGGCAA GATCGTCAAC TGGCTCTCGT
        Q  L  G  G    T  Q  I    M  Y  K    N  G  V  S    H  L  T    A  Q  N    D  Y  E  G    I  G  K    I  V  N    W  L  S  Y

5401    ACATTCCTGA GCGCAAGAAT GCACCGGTGC CCATCACGGT CAGCAACGAC ACCTGGGACC GCGACATCGA CTACTTGCCT CCCAAGGGTG CAGTCTATGA
        ·I  P  E   R  K  N    A  P  V  P    I  T  V    S  N  D    T  W  D  R    D  I  D    Y  L  P    P  K  G    A  V  Y  D·

5501    TCCCCGCTGG TTGATCGCTG GTAAGGAGGC TGAGGAGGAG GGCGCCTCTT TCCAGACTGG TTTCTTCGAC AAGGATTCGT TTACCGAGAC ATTGACGGGC
        P  R  W    L  I  A  G    K  E  A    E  E  E    G  A  S  F    Q  T  G    F  F  D    K  D  S  F    T  E  T    L  T  G

5601    TGGGCCCGCA CGGTTGTTGT TGGACGTGCC CGTCTCGGTG GTGTCCCTAT GGGAGTGATT GCAGTTGAGA CCCGCTCGGT CGAGCACATC ATCCCTGCTG
        W  A  R  T    V  V  V   G  R  A     R  L  G  G    V  P  M    G  V  I    A  V  E  T    R  S  V    E  H  I    I  P  A  D

5701    ATCCCGCCAA CGGCGACTCT GTCGAGCAGG TCTTGATGGA GGCTGGAAAT GTTTGGTACC CCAACTCGGC TTACAAGACT GCGCAGGCCA TCAACGACTT
        ·P  A  N    G  D  S    V  E  Q  V    L  M  E     A  G  N    V  W  Y  P    N  S  A    Y  K  T    A  Q  A    I  N  D  F·

5801    CAACAAGGGA GAGCAGCTTC CACTGATGAT CTTTGCCAAC TGGCGTGGAT TCTCGGGTGG TCAGCGCGAC ATGTACAATG AGATCCTCAA GTACGGTTCC
        ·N  K  G    E  Q  L  P    L  M  I    F  A  N    W  R  G  F    S  G  G    Q  R  D    M  Y  N  E    I  L  K    Y  G  S

5901    TTCATTGTCG ATGCTCTGAG CTCATACAAG CAGCCTGTGT TTGTCTATGT GGTTCCCAAC GGAGAGCTTC GTGGAGGTGC TTGGGTCGTC GTTGACCCTA
        F  I  V  D    A  L  S   S  Y  K     Q  P  V  F    V  Y  V    V  P  N    G  E  L  R    G  G  A    W  V  V    V  D  P  T

6001    CTATCAACGA GGACATGATG GAGATGTATG CTGACAAGCG GTCAAGAGCC GGTGTCTTGG AGCCTGAGGG TATTGTTGAG ATCAAGTTCC GTAAGGCCCA
        ·I  N  E   D  M  M    E  M  Y  A    D  K  R    S  R  A    G  V  L  E    P  E  G    I  V  E    I  K  F  R    K  A  Q·

6101    GTTGTTGGCG ACCATGGAGC GTTTGGACGA CAAGTACCGC GCATTGAAGG CCCAGTACGA GAACCCAGCC TTGGTTGGTA CCGAGCGCGA GGAGATCAAG
        ·L  L  A    T  M  E  R    L  D  D    K  Y  R    A  L  K  A    Q  Y  E    N  P  A    L  V  G  T    E  R  E    E  I  K

6201    ACGAAGCTGA CGGAGCGCGA GCAAGAGCTG TTGCCTGTGT ACCAGCAGCT GGCGATCCAA TTCGCGGATC TGCACGACAC TGCGGGACGC ATGAAGGCCA
        T  K  L  T    E  R  E    Q  E  L    L  P  V  Y    Q  Q  L    A  I  Q    F  A  D  L    H  D  T    A  G  R    M  K  A  K
```

Figure 1D

```
6301  AGGGCACGAT TCGTGAAGCC TTGGACTGGA CCAATGCCCG TCGCTACTTC TACTGGCGCG TGCGCAGAAG ATTGGCTGAG GAGTACATTC GTCGCAAGAT
      -G  T  I  R  E  A     L  D  W  T     N  A  R     R  Y  F     Y  W  R  V     R  R  R     L  A  E     E  Y  I  R     R  K  M-

6401  GGCTATTGCC AACAAGGACT TGAGCCGTGA GGAGCAGACC AAGTCGCTGC TGTCTTGGTT CGGCCGTGAC ACGGTGCACT CGAGCGAGAG CGAGCTGGAG
      -A  I  A     N  K  D  L     S  R  E     E  Q  T     K  S  L  L     S  W  F     G  R  D     T  V  H  S     S  E  S     E  L  E

6501  CAGATCTGGG AATCTGACGA TCGCGTGGTG TTGGAGTGGT TCGAGGGACA CGAGAGCAAG GTGACTGGAT TGATCCAGGA GCTGAACAAT GCGGCGACTG
      Q  I  W  E     S  D  D     R  V  V     L  E  W  F     E  G  H     E  S  K     V  T  G  L     I  Q  E     L  N  N     A  A  T  A

6601  CCAGCGAGGT GCTGAGAATG TACACCTCCA ACCGCGCTGG TGTGGTCGAG GGCTTCGATC GTATCCTTCA GAGCCTGTCG GACCAGGAGA AGCAGGACAT
      -S  E  V     L  R  M     Y  T  S  N     R  A  G     V  V  E     G  F  D  R     I  L  Q     S  L  S     D  Q  E  K     Q  D  I-

6701  CCTTGCCAAG TTCGCCACGA TGACCGTTTA AGAATTGATT TTTTNNGAAT CAATTTTTAG AGTAGAGTGA GAGTAGAACA GAGTGGAGGA ACTGGACACT
      -L  A  K     F  A  T  M     T  V

6801  CCTCCATCTT TGTGTTGTAA TTATAAAATT CATATCCATT TTCTTACAAA AAAAAAAAAA AAAAA
```

Figure 2A

```
                    1                                                                                                   100
     1S-4-cDNA      TCCCACTGACTCAAGCGGAACTTCCAAGCAACCATAATCCCATCATGACTACCAACGTACAGTCCTTCATTGGAGGAAACGCATTAGAGAACGCCCCTGC
     CBS528.72 gDNA -----------------------------------------------------------------------------------------------------
                    101                                                                                                 200
     1S-4-cDNA      TGGAGCTGTCCGCGAGTTTGTTAACCAGCATGGAGGCCACAGCGTGATCACCAAGATCCTGATCGCCAACAACGGTATTGCGGCCGTCAAGGAGATCCGA
     CBS528.72 gDNA -----------------------------------------------------------------------------------------------------
                    201                                                                                                 300
     1S-4-cDNA      TCTGTCCGCAAGTGGGCGTACGAGACCTTTGGAGATGAGCGTGCGATCCAGTTCACGGTCATGGCTACGCCAGAGGATCTGAAGATCAATGCTGAATATA
     CBS528.72 gDNA -----------------------------------------------------------------------------------------------------
                    301                                                                                                 400
     1S-4-cDNA      TCCGCATGGCCGACCAGTATGTCGAAGTACCGGGAGGATCCAACAACAACAACAGTACGGCAACGTTGACGTCATTGTCGACATTGCCGAACGGCACGGCGT
     CBS528.72 gDNA                                             AACAACAACAACTATGCGAACGTTGACGTCATTGTCGACATTGCCGAACGGCACGGCGT
                    401                                                                                                 500
     1S-4-cDNA      CCATGCTGTGTCGGCGTGGATG-------------------------------------------------------------------------------
     CBS528.72 gDNA TCATGCCGTGTGGGCTGGATGGTAAGTCAAGCAGTTTTGCCTGTTGGCAAATGGCAGATCGGGGTTCAATTTCATGGCGTGGCCGCCGTGTGGATGAAAA
                    501                                                                                                 600
     1S-4-cDNA      -----------------------------------------------------------------------------------------------------
     CBS528.72 gDNA GCGCTTGATGAGAGGCGAGGGAGGGCGAGGATGTCGCATGAATGTCGGCGTCTGTTCTCAGTGGGTGAAGATTGTACAACGAGGGTGTTTGTCCCCGGGC
                    601                                                                                                 700
     1S-4-cDNA      -----------------------------------------------------------------------------------------------------
     CBS528.72 gDNA GTGGCCATGGTTCGTGCTTGGGCATCTTTTTTGGGTTGTGTGTTTGATGCTGACAGCAAGGAATCGATGGTTGCTATCACCAATTTCATTCCCCAAAAAC
                    701                                                                                                 800
     1S-4-cDNA      -----------------------------------------------------------------------------------------------------
     CBS528.72 gDNA GAAAAAAAAAAAAAAAAGGGTCTCCCAAAAAAAAAAACTCCCCAGCAAAAAAAAAAAAAAATTGAAATGCGGTCACAGCGGACTCTTACAGAGAAAAAA
                    801                                                                                                 900
     1S-4-cDNA      -----------------------------------------------------------------------------------------------------
     CBS528.72 gDNA AAAAGAGCGGGGCAGAACCTTGTCCGAGTAAGAGTGCGGAAGAGTAGGGAACCCGGTGTCTATCTTTGGCCCACTGTTCACTCTTGCCTGTTGAGCCTCA
                    901                                                                                                 1000
     1S-4-cDNA      -----------------------------------------------------------------------------------------------------
     CBS528.72 gDNA AGGGTTTGGTGACCTCCGAGACGGCGCACAAGCGCGCGGGTCAGCAGCAGTGCGCTATGTGTGTGAAGAATCAACCGCGTCACCTGGCCATGGTAGCTCT
                    1001                                                                                                1100
     1S-4-cDNA      ---------------------------------------GGGACATGGCTCGGAGAACGCCAAAGTCGGAGAGTCTCTTCGGCGAGAGCGGTGAAAAGATC
     CBS528.72 gDNA CCACTCACCATGCATCACTTCCTTTCTCTCTCGCCACAGGGGACATGGCTCGGAAAAGGCGCAAGGTCGGAGAGTCCGTTCGGGAGAGCGGTGAAGAATC
                    1101                                                                                                1200
     1S-4-cDNA      ATCTTCATCGGACGCCCGGGTCCGGCATGGCGTCGTTGCGTGACAAGATCTCGTCGCAGGATGGTCGGCTCAATGCGGCGGACGTCGCCTAGGATGGGCTGGT
     CBS528.72 gDNA ATCTTCATCGGTCCGCGGGCTCCGGCATGGCGTCGCTGGGTGACAAGATCTCGTCGCACGATCGTCGCTCAGTCCGCCGACGGTTGCTAGTATGGGGTGGT
                    1201                                                                                                1300
     1S-4-cDNA      CCGGAACTGGCATCACAGAGAGTACCATGGATGCTAATGGTTTCGTCATGCTGCCCGACGATGCTTAGGAGCGTGCCTGTGTGCAGCGATGCAGAGGATGG
     CBS528.72 gDNA CCGGAACTGGCATCACAGAAACTCCATGGATGGCAATGGCTTTGTCACTGTGCCCGACGACGCTTAGGAGCGTGCCTGTGTCAGTGATGCAGAGGATGG
                    1301                                                                                                1400
     1S-4-cDNA      TCTTGAGAAGGCGACGACATCGGCTTGGGGGTGATGATCAAGGCTTGAGAGGGTGGTGGAGGAAACGGTATTCGTAAGGTTGAGGAACCGAGAAAGTTC
     CBS528.72 gDNA TCTTCAGAAGGGTGACAGGATTGGCTTGCCCATCATGATGAAAGGCTGCGACGGAGGTGGAGGAAAAGGTATCCGTAAGGTCGAGGATCGAGAAAGTTC
                    1401                                                                                                1500
     1S-4-cDNA      GCTCAGGCCTTCAACCAGTTTGGGCGAGGTCCCGGTTCCCGCGTCTTCATCATGAAGTTGGCTGGTAACGGCGCGATCTGGAGGTCGAGGTTTCG
     CBS528.72 gDNA GCTCAGGCCTTCAACCAAGTTCTGGGTGAGGTCGCCGGTTCCCGCGTCTTCATCATCAAGTTGGCCTCGTAATGGCGGCCATGTGGAGGTCGAGGTTTAG
                    1501                                                                                                1600
     1S-4-cDNA      CCGATCAGTATGGAAATGCCATCTCGGTCTTTGGACGGGATTGCTGTCTCGAGGGTCGGCATCAGAAGATTATTCGAGGAAGGCTCGGCGTCAGCATTCGCAA
     CBS528.72 gDNA CCGATCAGTACGGACACCGCATCTCGCTGTTCGGACGGGATTGCTCGGCAGCGGTCGGCATGAAAAGATCATTCGAGGACGGCTCGGCGTCAGCATTCGCAA
                    1601                                                                                                1700
     1S-4-cDNA      GCGGCGACAGCTTCGAGTCGATGGAGAAGGCTGCAGTGCGGTCTGGCCAAGTTGGTCGGATACGTTCTGGAGGTACGGTCGAGTACGCTGTACTCGGCACTCG
     CBS528.72 gDNA GCCGCGACAGCTTTTGAGTCGATGGAGAAGGCTGCAGTGCGGTCTGGCTAAGCTGGTCGGATACGTCTCTGGAGGTACGGTCGAATACCTCGTATTCGGCACTCG
                    1701                                                                                                1800
     1S-4-cDNA      AGTGACACGCTTCTTCTTCCTGGACTTGAACCCCAGAGTTCAGGTCGAGGATCGTACCACCGAGATGGTCTCAGGTGTCAACCTGCCCAGCTGCTCAGCTCG
     CBS528.72 gDNA ACCGACACGCTTCTTCTTCCTGGAATTGAACCCCAGAGTTCAGGTTGAGGATCCTACCACCGAGATGGTTTGTGGTGTTAACCTGCCAGCTGCTCAGCTTC
                    1801                                                                                                1900
     1S-4-cDNA      AGATCGCCATGGGTCTTCCTTTGAAGCGCATCAAGGACATCCGTGTTGTCTATGGTCTTCAACGCACAGGAACCTGGGAGATCGACTTTGAGTTTTCACA
     CBS528.72 gDNA AGCTCGCCATGGGTCTTCCTTTGAACCGGATCAAGGATATCCGTGTCGTCTATGGCTTCAGCCTACCGGAACCTGGGAGATCGACTTTGAGTTCTGTCA
                    1901                                                                                                2000
     1S-4-cDNA      GCAGATCTGGTATGAGAGTCAGGGCAAGGCGCCGGTAAGGGACACGTGATTGGTGTCCGGTATCAGAGGCGGAGAACCCCGATGCAGGATTCAAGCCCTCA
     CBS528.72 gDNA GCAGATCTGGTATGACGCCGAGCGCAAAGGCGGCGCAAGGGACACGTCATTGGCCGTTCGTATTAGGGCCGAGAAGCGTGATGCTGGATTCAAGCCCTCG
                    2001                                                                                                2100
     1S-4-cDNA      AGCGGAATGATGCAGGAACTCAATTTCAGATGCATCTACCAACGCTCTGGGGCTACTTCTCTGTCAACTCTGCAGGAGGACTGCACGAGTTTGCCCGATTCTC
     CBS528.72 gDNA AGCGGAATGATGCAGGAGCTCAACTTGCCGATCCTGCAGGAAGGTTTGGGGCTACTTT---------------------------------------------
```

Figure 2B

```
                    2101                                                                                         2200
        1S-4-cDNA   AGTTTGGTCATATCTTTGCCTATGGACAGGATCGTGGTCAGTCTAGAAAGAACATGGTCGTTGCCCTCAAGGAACTCTCCATTCGTGGTGATTTCCGCAC
     CBS528.72 gDNA ----------------------------------------------------------------------------------------------------
                    2201                                                                                         2300
        1S-4-cDNA   TACGGTCGAGTACTTGATCCGCCTTTTGGAGACACAGGAGTTCGAGGAAAACACCATTAACACTGGCTGGCTCGACAGCTTGATCTCCAACAACCTCACT
     CBS528.72 gDNA ----------------------------------------------------------------------------------------------------
                    2301                                                                                         2400
        1S-4-cDNA   GCTGAACGCCCTGAGACCATGTTGGCTGTCATGTGTGGTGCTGTTAACAGAGCCCACACCATCTCCGAGAACTGCATTAAGGAGTACAAGAAGTCGCTGG
     CBS528.72 gDNA ----------------------------------------------------------------------------------------------------
                    2401                                                                                         2500
        1S-4-cDNA   AGAAGGGTCAAGTGCCTAGCAAGGACGTTCTGCGCTCGGTCAACCAGCTTGACTTTATTTACGACGGCGTCCGCTACAACTTCACCGCCACTCGCTCTGG
     CBS528.72 gDNA ----------------------------------------------------------------------------------------------------
                    2501                                                                                         2600
        1S-4-cDNA   ACCCAACTCGTACACTCTGTACTTGAATGGATCCATGATCTCCATCTCTGTGCGTCCATTGACCGATGGCGGTCTCTTGGTCCTTTTGGATGGCAAGGCT
     CBS528.72 gDNA ----------------------------------------------------------------------------------------------------
                    2601                                                                                         2700
        1S-4-cDNA   CACACGACTTACTCGTTGGAAGAGGTCCAGGCCACTCGCCTGATGGTCGATGGAAAGACTTGTTTGTTGGAGAAGGAGAACGACCCTACTCAACTCCGCT
     CBS528.72 gDNA ----------------------------------------------------------------------------------------------------
                    2701                                                                                         2800
        1S-4-cDNA   CCCCCTCCCCAGGCAAACTTGTTCGCTACCTTGTCGAGTCTGGCGACCATGTTACGGCCAGCCAGGCCTATGCTGAGATTGAGGTCATGAAGATGTATAT
     CBS528.72 gDNA ----------------------------------------------------------------------------------------------------
                    2801                                                                                         2900
        1S-4-cDNA   GCCCTTGATCGCCACCGAGGACGGTATTGTGCAGTTCATCAAGCAACCCGGCACCACTCTGGATGCTGGTGATATCATTGGTATCCTCAGCTTGGACGAT
     CBS528.72 gDNA ----------------------------------------------------------------------------------------------------
                    2901                                                                                         3000
        1S-4-cDNA   CCCTCCCGCGTTCGCCACGCTAAGCCCTTCGAAGGTCAGCTCCCTCCCATGGGTCAGCCCACCATTCACGGAGCTAAGCCCCATCAGCGTTACCGCGAGC
     CBS528.72 gDNA ----------------------------------------------------------------------------------------------------
                    3001                                                                                         3100
        1S-4-cDNA   TGCGACTCGTCCTCGACAATGCCATGGATGGCTACGATAACCAGGCTTTGGTCCAGCCTACGCTGAAGGAGATCTTTGAGGTCCTCCAGACCCCGGAGCT
     CBS528.72 gDNA ----------------------------------------------------------------------------------------------------
                    3101                                                                                         3200
        1S-4-cDNA   GCCCTACTTGGAATTCAACGAGGTCTTTGCTTCGCTAAGCGGAAGAATCCCACCCAAGCTGGAAATTGCCCTGCACCAGGAGGTGGATCAGTCCATGAAG
     CBS528.72 gDNA ----------------------------------------------------------------------------------------------------
                    3201                                                                                         3300
        1S-4-cDNA   AACCACGAGCACTTCCCCGCTCGTACTCTTCAGGCCCTGATTGACTCGCACTGCCGCGCCAACTTCTCCAAGGCCGCCGATATCAATGCGTTCCAAGCCT
     CBS528.72 gDNA ----------------------------------------------------------------------------------------------------
                    3301                                                                                         3400
        1S-4-cDNA   CGGTGGGACCTCTGACCGCCATCATCAAGGAGTACCAACACGGTTTGAAAACTCACTCCTGGGGCTTCATTGCTGATTACCTCAACAAGTACCATGAAGT
     CBS528.72 gDNA ----------------------------------------------------------------------------------------------------
                    3401                                                                                         3500
        1S-4-cDNA   CGAGTCGCTCTTTGATGACTCTGCTCGTGAGGAAGAGATCTTCCTGTCCCTGCGTGATCAGAACAAGGACGACGTCGAGAAGGTCATCCGCATCGCACTC
     CBS528.72 gDNA ----------------------------------------------------------------------------------------------------
                    3501                                                                                         3600
        1S-4-cDNA   TCGCACTCGCGTGTCACTGCCAAGAACAACTTGGTTTTGACCCTTCTTGACCAGATCAAACCTACGGCCTCTGGAGGAGCGCTCGACAAGTTCTTCTCGC
     CBS528.72 gDNA ----------------------------------------------------------------------------------------------------
                    3601                                                                                         3700
        1S-4-cDNA   CTGTGCTCAAGAAGCTGGCTGAGCTTACTGGCCGTCTCACCGCCAAGGTCTCGCTCAAGGCCAGAGAGCTCCTTATTCATGTTCAGTTGCCCAGCTTTGA
     CBS528.72 gDNA ----------------------------------------------------------------------------------------------------
                    3701                                                                                         3800
        1S-4-cDNA   GGAACGCCAGTCGCAGATGGAGAAGATCCTCCGCTCGAGCGTCACTGAGGAGGTTTATGGTGGTGAACACGAGGCCCGCATGCCTGCCTTTGAGAACATC
     CBS528.72 gDNA ----------------------------------------------------------------------------------------------------
                    3801                                                                                         3900
        1S-4-cDNA   AAGGAGTTGGTCGACACCACCTACACAGTCTTTGATGTCTTGCCTAACTTCTTTTACCATGAGTCGTTGCATGTCCGCATTGCCGCGTTCGAGGTGTACT
     CBS528.72 gDNA ----------------------------------------------------------------------------------------------------
                    3901                                                                                         4000
        1S-4-cDNA   GCCGTCGTGCCTACCATGCGTACGAGATTTTGGACATCAATTACCACATGGAGCACCAGCCCTTGCTGATCACTTGGAAGTTCTTGCTCAACACCCCCAA
     CBS528.72 gDNA ----------------------------------------------------------------------------------------------------
                    4001                                                                                         4100
        1S-4-cDNA   CAAGTCCGAGTCTGGTCCCAACCGTGTGGCTAGTGTCAGTGACATGAGTTACTTGATCAACAAGGCTGACCCTGAGCCTGTTCGTACCGGTGCCATTCTT
     CBS528.72 gDNA ----------------------------------------------------------------------------------------------------
                    4101                                                                                         4200
        1S-4-cDNA   GCCGTTCGCGACGTGAAGGAGCTGGAGGACAGATTCGAGAGCATCCTCAACTTCTTCCCCTCTCACAAGTCGAACAAGCACTTGAGCCATCTCGCTGCCG
     CBS528.72 gDNA ----------------------------------------------------------------------------------------------------
```

Figure 2C

```
                      4201                                                                                       4300
       1S-4-cDNA      CCAGCGTCCACAACAATGTGTTGAACGTTGTCATCAAGTCCGAGTCGGTTCACCCCAACGATGATGACTACTGGCTGAACCTCCTCAGCCCCATCGTGAA
    CBS528.72 gDNA    ----------------------------------------------------------------------------------------------------
                      4301                                                                                       4400
       1S-4-cDNA      GGGCGAGACCGAGCGCCTTCGCTCGCACGGGCATCCGTCGCATGACCTTCTTGATCTTCCGTCAGGGCAACTACCCCTCGTACTTCACCTTCCGTGAGCGT
    CBS528.72 gDNA    ----------------------------------------------------------------------------------------------------
                      4401                                                                                       4500
       1S-4-cDNA      AACAACTACGCTGAGGATCAGACCATCCGTCACATCGAGCCCGCCATGGCATACCGTCTTGAGTTGGCGCGCTTGTCCAACTTTGACATCAAGCCCTGCT
    CBS528.72 gDNA    ----------------------------------------------------------------------------------------------------
                      4501                                                                                       4600
       1S-4-cDNA      TCATTGACAATCGCCAGGTTCATGTGTACTATGCTGTGGGCAAGGAGAACATTTCGGACTGCCGCCTTCTTTGTCTGCGCCTTGGTTCGTCCTGGTCGCCT
    CBS528.72 gDNA    ----------------------------------------------------------------------------------------------------
                      4601                                                                                       4700
       1S-4-cDNA      GCGCTCTAGCGTTCGTACGGCGGATTACTTGATTTCGGAGACCGACCGTCTGTTGAACGATATTCTGGATGCTCTGGAGATTGTGGGTGCCACCTACAAG
    CBS528.72 gDNA    ----------------------------------------------------------------------------------------------------
                      4701                                                                                       4800
       1S-4-cDNA      CAGAGTGACTGCAACCACTTGTTTATCAACTTCATCCCCACTTTCCAGTTGGACGCTACCGAGGTTGAGACTGCCCTCAAGGGATTCATTGACCGCCACG
    CBS528.72 gDNA    ----------------------------------------------------------------------------------------------------
                      4801                                                                                       4900
       1S-4-cDNA      GCAAGCGTCTCTGGCGTCTTCGCGTCACTGGCGCTGAGATTCGCTTCAATGTTCAGTCCAAGTCTGCGAATGGCGTTGAGGCCGACCCCGTTCCTCTTCG
    CBS528.72 gDNA    ----------------------------------------------------------------------------------------------------
                      4901                                                                                       5000
       1S-4-cDNA      ATTCATCATCTCCAACGTCTCTGGATATGTCTTGAACGTCGACACCTACCGCGAGGTTCAGACCGAGAAGGGTGCCATCTTCAAGTCGGTTGGTCCTACC
    CBS528.72 gDNA    ----------------------------------------------------------------------------------------------------
                      5001                                                                                       5100
       1S-4-cDNA      GGTCCCTTCCATCTCTTGCCTGTGAACCAGCCCTACCCCACAAAGGAGTGGCTTCAGCCCAGACGTTACAAGGCACACTTGATGGGCACGACTTACGTCT
    CBS528.72 gDNA    ----------------------------------------------------------------------------------------------------
                      5101                                                                                       5200
       1S-4-cDNA      ATGACTTTGGCGAGCTCTTCCGCCAGGCCGTCCGTGCTCAGTGGAACCATGCCATCAAGCAGAACTCTTCGCTCAAGGTCCCATCCCAGGTCTTGGAGAT
    CBS528.72 gDNA    ----------------------------------------------------------------------------------------------------
                      5201                                                                                       5300
       1S-4-cDNA      GCGCGAGCTGGTCTTGGATGAGAGACAGCAGTTGCAGCAGGTCGTTCGCGATGCCGGTTCCAACAACTGCGGCATGGTTGCCTGGATTTTCACTCTCCGT
    CBS528.72 gDNA    ----------------------------------------------------------------------------------------------------
                      5301                                                                                       5400
       1S-4-cDNA      ACCCCCGAGTACCCCGAGGGTCGACAGATCATTGTCATTGCCAACGATATCACCTTCAACATTGGATCGTTTGGACCCGAGGAGGACCTGGTCTTCTACA
    CBS528.72 gDNA    ----------------------------------------------------------------------------------------------------
                      5401                                                                                       5500
       1S-4-cDNA      AGGCGTCCGAGATGGCCAGAAAGTTGGGCATTCCCCGTGTTTACCTCTCTGCCAACTCTGGTGCCCGCATTGGTCTTGCTAGTGAAGTGATTGGTCTCTT
    CBS528.72 gDNA    ----------------------------------------------------------------------------------------------------
                      5501                                                                                       5600
       1S-4-cDNA      CAACTCTTGCTGGAACGACGCTTCCAACCCCTCCAAGGGCTTCAAGTACATCTACCTCACGGACGCTGGACTGAAGCAGTTGGAGGCTCAGGAGGAGCGC
    CBS528.72 gDNA    ----------------------------------------------------------------------------------------------------
                      5601                                                                                       5700
       1S-4-cDNA      TCTGGTAAGAAGAGCGTCATCACAGAGACCATTGTTGAGGATGGCGAGACCCGCCATAAGATCACGGATGTCATCGGTGCTGTCGACGGTCTTGGTGTTG
    CBS528.72 gDNA    ----------------------------------------------------------------------------------------------------
                      5701                                                                                       5800
       1S-4-cDNA      AGAACTTGCGCGGAAGTGGTCTGATTGCTGGAGAGACCTCGCGAGCCTACGACGACATCTTTACCATTACTTTGGTCACCTGCCGCTCTGTTGGTATCGG
    CBS528.72 gDNA    ----------------------------------------------------------------------------------------------------
                      5801                                                                                       5900
       1S-4-cDNA      TGCGTACTTGGTTCGTTTGGGTCAGCGTACTATTCAGAATGAGGGCCAGCCCATCATTTTGACTGGTGCCCCTGCCCTCAACAAGTTGCTTGGTCGCGAT
    CBS528.72 gDNA    ----------------------------------------------------------------------------------------------------
                      5901                                                                                       6000
       1S-4-cDNA      GTCTACACCTCGAACTTGCAGCTCGGAGGCACTCAGATTATGTACAAGAACGGAGTGTCGCACTTGACCGCTCAGAACGACTATGAGGGTATTGGCAAGA
    CBS528.72 gDNA    ----------------------------------------------------------------------------------------------------
                      6001                                                                                       6100
       1S-4-cDNA      TCGTCAACTGGCTCTCGTACATTCCTGAGCGCAAGAATGCACCGGTGCCCATCACGGTCAGCAACGACACCTGGGACCGCGACATCGACTACTTGCCTCC
    CBS528.72 gDNA    ----------------------------------------------------------------------------------------------------
                      6101                                                                                       6200
       1S-4-cDNA      CAAGGGTGCAGTCTATGATCCCCGCTGGTTGATCGCTGGTAAGGAGGCTGAGGAGGAGGGCGCCTCTTTCCAGACTGGTTTCTTCGACAAGGATTCGTTT
    CBS528.72 gDNA    ----------------------------------------------------------------------------------------------------
                      6201                                                                                       6300
       1S-4-cDNA      ACCGAGACATTGACGGGCTGGGCCCCGCACGGTTGTTGTTGGACGTGCCCCGTCTCGGTGGTGTCCCTATGGGAGTGATTGCAGTTGAGACCCGCTCGGTCG
    CBS528.72 gDNA    ----------------------------------------------------------------------------------------------------
```

*Figure 2D*

```
                 6301                                                                                       6400
      1S-4-cDNA  AGCACATCATCCCTGCTGATCCCGCCAACGGCGACTCTGTCGAGCAGGTCTTGATGGAGGCTGGAAATGTTTGGTACCCCAACTCGGCTTACAAGACTGC
    CBS528.72 gDNA  ----------------------------------------------------------------------------------------------------
                 6401                                                                                       6500
      1S-4-cDNA  GCAGGCCATCAACGACTTCAACAAGGGAGAGCAGCTTCCACTGATGATCTTTGCCAACTGGCGTGGATTCTCGGGTGGTCAGCGCGACATGTACAATGAG
    CBS528.72 gDNA  ----------------------------------------------------------------------------------------------------
                 6501                                                                                       6600
      1S-4-cDNA  ATCCTCAAGTACGGTTCCTTCATTGTCGATGCTCTGAGCTCATACAAGCAGCCTGTGTTTGTCTATGTGGTTCCCAACGGAGAGCTTCGTGGAGGTGCTT
    CBS528.72 gDNA  ----------------------------------------------------------------------------------------------------
                 6601                                                                                       6700
      1S-4-cDNA  GGGTCGTCGTTGACCCTACTATCAACGAGGACATGATGGAGATGTATGCTGACAAGCGGTCAAGAGCCGGTGTCTTGGAGCCTGAGGGTATTGTTGAGAT
    CBS528.72 gDNA  ----------------------------------------------------------------------------------------------------
                 6701                                                                                       6800
      1S-4-cDNA  CAAGTTCCGTAAGGCCCAGTTGTTGGCGACCATGGAGCGTTTGGACGACAAGTACCGCGCATTGAAGGCCCAGTACGAGAACCCAGCCTTGGTTGGTACC
    CBS528.72 gDNA  ----------------------------------------------------------------------------------------------------
                 6801                                                                                       6900
      1S-4-cDNA  GAGCGCGAGGAGATCAAGACGAAGCTGACGGAGCGCGAGCAAGAGCTGTTGCCTGTGTACCAGCAGCTGGCGATCCAATTCGCGGATCTGCACGACACTG
    CBS528.72 gDNA  ----------------------------------------------------------------------------------------------------
                 6901                                                                                       7000
      1S-4-cDNA  CGGGACGCATGAAGGCCAAGGGCACGATTCGTGAAGCCTTGGACTGGACCAATGCCCGTCGCTACTTCTACTGGCGCGTGCGCAGAAGATTGGCTGAGGA
    CBS528.72 gDNA  ----------------------------------------------------------------------------------------------------
                 7001                                                                                       7100
      1S-4-cDNA  GTACATTCGTCGCAAGATGGCTATTGCCAACAAGGACTTGAGCCGTGAGGAGCAGACCAAGTCGCTGCTGTCTTGGTTCGGCCGTGACACGGTGCACTCG
    CBS528.72 gDNA  ----------------------------------------------------------------------------------------------------
                 7101                                                                                       7200
      1S-4-cDNA  AGCGAGAGCGAGCTGGAGCAGATCTGGGAATCTGACGATCGCGTGGTGTTGGAGTGGTTCGAGGGACACGAGAGCAAGGTGACTGGATTGATCCAGGAGC
    CBS528.72 gDNA  ----------------------------------------------------------------------------------------------------
                 7201                                                                                       7300
      1S-4-cDNA  TGAACAATGCGGCGACTGCCAGCGAGGTGCTGAGAATGTACACCTCCAACCGCGCTGGTGTGGTCGAGGGCTTCGATCGTATCCTTCAGAGCCTGTCGGA
    CBS528.72 gDNA  ----------------------------------------------------------------------------------------------------
                 7301                                                                                       7400
      1S-4-cDNA  CCAGGAGAAGCAGGACATCCTTGCCAAGTTCGCCACGATGACCGTTTAAGAATTGATTTTTTNNGAATCAATTTTTAGAGTAGAGTGAGAGTAGAACAGA
    CBS528.72 gDNA  ----------------------------------------------------------------------------------------------------
                 7401                                                                                       7500
      1S-4-cDNA  GTGGAGGAACTGGACACTCCTCCATCTTTGTGTTGTAATTATAAAATTCATATCCATTTTCTTACAAAAAAAAAAAAAAAAAA-----------------
    CBS528.72 gDNA  ----------------------------------------------------------------------------------------------------
```

Figure 3A

```
         1                                                                                                   100
1S-4     MTTNVQSFIGGMALENAPAGAVREFVNQHGGHSVITKILIANNGIAAVKEIRSVRKWAYETFGDERAIQFTVMATPEDLKINAEYIRMADQYVEVPGGSN
CBS528.72                                                                                                  N 101                                                                                                 200
1S-4     NNNYANVDLIVDIAERTGVHAVWAGHGHASENPKLPESLRDSPQKLIFIGPPGGSAMRSLGDKLSSTIVAQSADVPTMGNSGTGITETTMDANGFVMVPED
CBS528.72 NNNYANVDLIVDIAERTGVHAVWAGHGHASENPKLPESLRDSPQKLIFIGPPGGSAMRSLGDKLSSTIVAQSADVPTMGWSGTGITETAMDANGFVTVPDD 201                                                                                                 300
1S-4     AYQAACVTDAEDGLQKAHTIGFPVMLKASEGGGGKGIRKVEEPEKFAQAFNQVLGEVPGSPVFIMKLAGNARHLEVQLLADYGNAISLFGRDCSVQRRH
CBS528.72 AYQAACVTDAEDGLQKAHTIGFPIMLKASEGGGGKGIRKVEDPEKFAQAFNQVLGEVPGSPVFIMKLAGNARHLEVQLLADYGHAISLFGRDCSVQRRH 301                                                                                                 400
1S-4     QKIEEAPVTIAKPDTFESMEKAAVRLAKLIGYVSAGTVEYLYSHSTDTFFFLEINPRLQVEHPTTEMVSGVNLPAAQLQIAMGLPLNRIKDIRVLYGLQ
CBS528.72 QKIEEAPVTIAKPDTFESMEKAAVRLAKIJGYVSAGTIVEYLYSHSTDTFFFLEINPRLQVEHPTTEMVSGVNLPAAQLQVAMGLPLNRIKDIRVLYGLQ 401                                                                                                 500
1S-4     PTGTSEIDFEFSQQISYETQRKPAPKGHVIAVRITAENPDAGFKPSSGMMQELNEFSSTINVNGYFSVNSAGGLHEFADSQFGHIFAYGQDRGQSRKNMVV
CBS528.72 PTGISEIDFEFSQQISYETQRKPAPKGHVFAVRITAENPDAGFKPSSGMMQELVFRSSTIKVWGYP 501                                                                                                 600
1S-4     ALKELSIRGDFRTTVEYLIRLLETQEFEENTINTGWLDSLISNNLTAERPETMLAVMCGAVNRAHTISENCIKEYKKSLEKGQVPSKDVLRSVNQLDFIY 601                                                                                                 700
1S-4     DGVRYNFTATRSGPNSYTYLNGSMISISVRPLTDGGLLVLLDGKAHTTYSLEEVQATRLMVDGKTCLLEKENDPTQLRSPSPGKLVRYLVESGDHVTAS 701                                                                                                 800
1S-4     QAYAEIEVMKMYMPLIATEDGIVQFIKQPGTTLDAGDIIGILSLDDPSRVRHAKPFEGQLPPMGQPTIHGAKPHQRYRELRLVLDNAMDGYDNQALVQPT 801                                                                                                 900
1S-4     LKEIFEVLQTPELPYLEFNEVFASLSGRIPPKLEIALHQEVDQSMKNHEHFPARTLQALIDSHCRANFSKAADINAFQASVGPLTAIIKEYQHGLKTHSW 901                                                                                                 1000
1S-4     GFIADYLNKYHEVESLFDDSAREEEIFLSLRDQNKDDVEKVIRIALSHSRVTAKNNLVLTLLDQIKPTASGGALDKFFSPVLKKLAELTGRLTAKVSLKA
```

Figure 3B

```
              1001                                                                                    1100
    1S-4      RELLIHVQLPSFEERQSQMEKILRSSVTEEVYGGEHEARMPAFENIKELVDTTYTVFDVLPNFFYHESLHVRIAAFEVYCRRAYHAYEILDINYHMEHQP
 CBS528.72
              1101                                                                                    1200
    1S-4      LLITWKFLLNTPNKSESGPNRVASVSDMSYLINKADPEPVRTGAILAVRDVKELEDRFESILNFFPSHKSNKHLSHLAAASVHNMVLNVVIKSESVHPND
 CBS528.72
              1201                                                                                    1300
    1S-4      DDYWLNLLSPIVKGETERLRSHGIRRMTFLIFRQGNYPSYFTFRERNMYAEDQTIRHIEPAMAYRLELARLSNFDIKPCFIDNRQVHVYYAVGKENISDC
 CBS528.72
              1301                                                                                    1400
    1S-4      RFFVCALVRPGRLRSSVRTADYLISETDRLLNDILDALEIVGATYKQSDCNHLFINFIPTFQLDATEVETALKGFIDRHGKRLWRLRVTGAEIRFNVQSK
 CBS528.72
              1401                                                                                    1500
    1S-4      SANGVEADPVPLRFIISNVSGYVLNVDTYREVQTEKGAIFKSVGPTGPFHLLPVNQPYPTKEWLQPRRYKAHLMGTTYVYDFGELFRQAVRAQWNHAIKQ
 CBS528.72
              1501                                                                                    1600
    1S-4      NSSLKVPSQVLEMRELVLDERQQLQQVVRDAGSNNCGMVAWIFTLRTPEYPEGRQIIVIANDITFNIGSFGPEEDLVFYKASEMARKLGIPRVYLSANSG
 CBS528.72
              1601                                                                                    1700
    1S-4      ARIGLASEVIGLFNSCWNDASNPSKGFKYIYLTDAGLKQLEAQEERSGKKSVITETIVEDGETRHKITDVIGAVDGLGVENLRGSGLIAGETSRAYDDIF
 CBS528.72
              1701                                                                                    1800
    1S-4      TITLVTCRSVGIGAYLVRLGQRTIQNEGQPIILTGAPALNKLLGRDVYTSNLQLGGTQIMYKNGVSHLTAQNDYEGIGKIVNWLSYIPERKNAPVPITVS
 CBS528.72
              1801                                                                                    1900
    1S-4      NDTWDRDIDYLPPKGAVYDPRWLIAGKEAEEEGASFQTGFFDKDSFTETLTGWARTVVVGRARLGGVPMGVIAVETRSVEHIIPADPANGDSVEQVLMEA
 CBS528.72
              1901                                                                                    2000
    1S-4      GNVWYPNSAYKTAQAINDFNKGEQLPLMIFANWRGFSGGQRDMYNEILKYGSFIVDALSSYKQPVFVYVVPNGELRGGAWVVVDPTINEDMMEMYADKRS
 CBS528.72
```

Figure 3C

```
           2001                                                                              2100
    1S-4   RAGVLEPEGIVEIKFRKAQLLATMERLDDKYRALKAQYENPALVGTEREEIKTKLTEREQELLPVYQQLAIQFADLHDTAGRMKAKGTIREALDWTNARR
CBS528.72  ------------------------------------------------------------------------------------------------

2101                                                                              2200
    1S-4   YFYWRVRRRLAEEYIRRKMAIANKDLSREEQTKSLLSWFGRDTVHSSESELEQIWESDDRVVLEWFEGHESKVTGLIQELNNAATASEVLRMYTSNRAGV
CBS528.72  ------------------------------------------------------------------------------------------------

2201              2228
    1S-4   VEGFDRILQSLSDQEKQDILAKFATMTV
CBS528.72  ----------------------------
```

```
          1001                                                                                      1100
MaACC     ALDKFFSPVIKKLAELTGRLTAKVSLKARELIHVQLRSFEERQSQMEKILRSSVTEEVYGGEHEAR--MPAFENIKELVDTITYTVFDVLPNFFYHESLHV
ScACC1    KVSAIFSTPLQHIVELESKATAKVALQAREILQGALPSVKERTEQIEHILKSSVVKVAYGSSNPKRSEPDLNILKDLDSNYVVFDVLQFLTHQDPVV
ScHFA1    KMSLKFRAVIHDEASLESKWAKENAVKARSVLRGIFPPIKKRKEHIKTLLQLHIKDTGAENIHSRNIYSCMRDFGNLHSNLIQLQDLFFFGHQDTAL 1101                                                                                      1200
MaACC     RIAAFEVYCRRAYHAVELLDINYFMEHQPLLITWKGELINTPNKS------------ESGPNRVASVSDMSYLINKADPEPVRTCAILAVRDVKELEDRFESIINF
ScACC1    TAAAQVYIRRAYRAYTIGDIRVHEGVTVPIVEHKFQIPSAAFSTFPTVKSKMGMNRAVSVSDLSMVANSQS--SPLREGILMAVDHLDDVDEILSQSLEV
ScHFA1    SSIASEIYARYAVGNVQLKSIKIHKGAPDLMSWQFSSLRNYLVNSDGESDEFTKLSKPPSTSGKSSAMS------------FGLLVNMRALESLEKTLDEVYEQ 1201                                                                                      1300
MaACC     FPSHKSNKHLS----HLAAASVHNNVLNVVIIKSESVHPNDDDYWLNILSPIVKGETERLRSHGIIRMTFLIFRQGNYPSYFTERERNNYAEDQTIRHIEPA
ScACC1    IPRHQSSSMGPAPDRSGSSASLSNVANVCVASTEGFESEEEILVRLREILDLNKQELINASIRRITFMEGEKDGSYPKYTENG-PNYNENETIRHIEPA
ScHFA1    IHIPEERLS-------SGENSLIVNILSPIRYRSENDLIKTLKIKHENERGISKLKVNRITEAFIAANAPAVKFYSFDG-TTYDEISQIRNMDPS 1301                                                                                      1400
MaACC     MAYRLELARLSNFEDIKPCFIDNRQVHVYYAVGKENISDCRFFVCALVRPGRLRSSVRIADYLISETDRILNDILDALEIVGATYKQSDCNHLFINFIPTE
ScACC1    LAFQLELGRLSNENIKPIFTDNRNHVYEAVSKTSPEDKRFFTRGIRTGHIRDDISIQEYLTSEANRLMSDILDNLEVTDTSN----SDLNHIFINFIANF
ScHFA1    YEAPLELGKMSNYKIRSLPLTYDSSIRIFEGISKFTPLDKRFFVRKIINSFMYNDQKTIEENLKAEIAQVVYMLEHLGAVDISN----SDLNHIFLSFNTVL 1401                                                                                      1500
MaACC     QLDATEVETALKGFIDRHGKRLWRLRVTGAEIRFMQSKSANGVEADPVPLRFISNVSGVYLNVDTYREVQTEKG-ALFKSVGPTGPFHLLPVNQPYPT
ScACC1    DISPEDVEAAFGGFLERFGKRLLRLRVSSAEIRIIKDPQTG-------APVPLRALINJVSGVVIKTEMVTEVKNAKGEWVFKSLGKPGSMHLRPIATPYPV
ScHFA1    NIPVHRLEEIVSTILKTHETRLFQERIIDVELCISVECLEIK------KPAPLRLISNKGVVVKIETYVEKIGKNGNLILEPCSEQHYSQKSLSLPMSV
```

```
              2001                                                                                                    2100
MaACC   SYKQPVFVYVVPNGELRGGAHVVVDPTINEDMMEMYADKRSRAGVIEPEGIVE KFRKAQL A ER DDKYRA KAQYENPA VGTEREE KTKL TERE
ScACC1  DYKQPI I YIPPTGELRGGSWVVVDPTINADQMEMYADVINARAGVIEPQGMMG KFRREKL D NR LDDKYRE RSQLSNKSLAPEVHQQUSKQLADRE
ScHFA1  DYKQPIL YIPPFGELRGGSWV IDPTINPEQMEMYADIES GG EEPDCVVS KYRKEKMIETNI RLDSTVGH RRTITEKKLSLEKQNDLTKRLKIRE 2101                                                                                                    2200
MaACC   QELLPVVQQLAI QFADLHDTAGRMKAKGTIREALDVNARRYFYMRVRRRLAFEYIRRKMAIANKDLSREEQTKSLLSWFGRDTVHSSESELEQIWESDD
ScACC1  REILPIVGQISLQFADLHDRSSRNVAKGVISKELEWIEARRFF MRLRRRLNEE L IKRL SHQVGEAS----------RLEKIARIIRSWYPASVDHEDD
ScHFA1  RQLIPIMNQISIQFADLHDRSTRMLVKGVIRNELEWKKSPRFLVMRLRRRLNEGQV KRLQKKTCDNKTK-------MKYDDLLK VQSWYNDLDVNDD 2201                                                                 2269
MaACC   RVWLEWFEGHESKVTGLIQELNNAATASEVLRMYTSNRAGVVEGFDRILQSSDQEKQDILAKFATMTV
ScACC1  RQVATWIEENYKTLDDKLKGIKLESFAQDLAKKIIRSDHDNAIDCISEVIKMISTDDKEKLIKTLK------
ScHFA1  RAVVEFIERNSKRIDKNIEEFEISLLIDELKKIFEDRRG---NIVLEELTRLVDSKRKR------
```

ACETYL-COA CARBOXYLASE

SEQUENCE LISTING

The instant application contains a Sequence Listing which has been submitted in ASCII format via EFS-Web and is hereby incorporated by reference in its entirety. Said ASCII copy, created on Nov. 10, 2011, is named P40704.txt and is 155,988 bytes in size.

TECHNICAL FIELD

The present invention relates to a novel acetyl-CoA carboxylase.

BACKGROUND ART

Fatty acids are important components of lipids such as phospholipids and triacylglycerols. Fatty acids containing two or more unsaturated bonds, which are collectively referred to as polyunsaturated fatty acids (PUFAs), and are known to include arachidonic acid, dihomo-γ-linolenic acid, eicosapentaenoic acid and docosahexaenoic acid. Various physiological activities have been reported for these fatty acids (non-patent document 1).

Among them, arachidonic acid has attracted attention as an intermediate metabolite in the synthesis of prostaglandins, leukotrienes and the like, and many attempts have been made to apply it as a material for functional foods and medicines. Furthermore, arachidonic acid is contained in breast milk so that it is important for the growth of infants, especially for the growth of fetal length and brain, and therefore, it also attracts attention as well as DHA (docosahexaenoic acid) in a nutritional aspect as a necessary component for the growth of infants.

These polyunsaturated fatty acids are expected to be applied in various fields, but some of them cannot be synthesized in vivo in animals. This has led to development of methods for obtaining polyunsaturated fatty acids by culturing various microorganisms. Attempts to produce polyunsaturated fatty acids in plants have also been made. In such cases, polyunsaturated fatty acids are known to be accumulated as components of reserve lipids such as triacylglycerols, for example, in microbial cells or plant seeds.

Although the molecular structures of enzymes involved in de novo fatty acid synthesis and fatty acid chain elongation differ between prokaryotes and eukaryotes, the mechanisms of enzymatic reactions are similar in any type of cells. Fatty acid biosynthesis starts from acetyl-CoA, and maronyl-CoA is produced from acetyl-CoA by catalysis of acetyl-CoA carboxylase (E.C.6.4.1.2). Various saturated fatty acids are synthesized by adding two carbon atoms via decarboxylative coupling of acetyl-CoA with malonyl-CoA in a series of condensation-reduction-dehydration-reduction reactions catalyzed by fatty acid synthetases (FASs). Similarly, fatty acid chain elongation reactions involve adding two carbon atoms via decarboxylative coupling of acyl-CoA with malonyl-CoA in a series of condensation-reduction-dehydration-reduction reactions.

Acetyl-CoA carboxylases (hereinafter also referred to as "ACCs") have been hitherto reported in several organisms. Mammalian ACCs are typical allosteric enzymes having the property of being activated by citric acid, inhibited by long-chain fatty acid CoA esters and inactivated by phosphorylation. In fungi, the ACC from yeast (*Saccharomyces cerevisiae*) has been extensively studied.

The ACC from *S. cerevisiae* is localized in the cytoplasm and mitochondria and encoded by the ACC1 and HFA1 genes, respectively. The ACC1 gene is known to be an essential gene whose deletion leads to death (non-patent document 2). Analysis of variant strains revealed that the ACC1 gene is also involved in the transport of polyA+ mRNA from the nucleus and other roles (non-patent document 3).

In plants, attempts were made to increase fats in seeds using ACC genes (non-patent document 4). For example, a report shows that the fatty acid content on a dry weight basis increased and compositional ratio of the fatty acids also changed in the seeds of transgenic *Brassica napus* L. expressing the ACC of *Arabidopsis thaliana* (non-patent document 5). However, the pattern of change in compositional ratio of fatty acids depends on the compositional ratio of fatty acids inherent in the host organism and the ACC gene transduced. On the other hand, ACC activity undergoes various regulations not only at the expression level but also at the protein level (non-patent documents 3 and 4), and it is also influenced by interactions with other enzymatic proteins functioning in a series of fatty acid synthesis systems. Therefore, a suitable ACC gene may be necessary to obtain a desired fatty acid composition depending on the host organism to be transformed.

As for the ACC gene of a lipid-producing fungus *Mortierella alpina* (hereinafter also referred to as "*M. alpina*"), a fragment of a gene for an ACC homolog from strain CBS 528.72 presumably having ACC activity has previously been known (non-patent document 6). However, it has not been confirmed yet that a protein having this fragment has ACC activity. *M. alpina* strain CBS696.70 has been assessed for fat accumulation and acetyl-CoA carboxylase activity (non-patent document 7).

REFERENCES

Non-Patent Documents

Non-patent document 1: Lipids, 39, 1147 (2004)
Non-patent document 2: Giaever G. et al. Nature 418, 387-91 (2002)
Non-patent document 3: O. Tehlivets et al., Biochimica et Biophysica Acta, 1771, 255-270 (2007)
Non-patent document 4: Biosci. Biotechnol. Biochem., 68 (6), 1175-1184, (2004)
Non-patent document 5: Plant Physiol. 113, 75-81 (1997)
Non-patent document 6: The International Nucleotide Sequence Database accession number AJ586915
Non-patent document 7: Microbiology, 145, 1911-1917 (1999)

SUMMARY OF INVENTION

Technical Problems

However, the ACC genes hitherto reported were said to have insufficient effect on lipid metabolism when they were transferred and expressed in host organisms. They also had the disadvantage that they were insufficiently effective to increase or decrease the accumulation of fats or fatty acids in some hosts. Therefore, there is a need to identify a novel protein that would influence lipid metabolism of a host when it is transferred and expressed in a host cell. There is also a need to identify a protein capable of producing fats with a high content of industrially valuable fatty acids.

Solution to Problems

An object of the present invention is to provide proteins and nucleic acids capable of producing valuable fats by expressing them in a host cell to influence lipid metabolism of the host or to increase the content of a desired fatty acid.

The inventors carefully studied to attain the above object. First, sequences sharing high identity to known ACC genes were extracted by EST analysis of a lipid-producing fungus *M. alpina*. To obtain a complete open reading frame (ORF) encoding an ACC, full-length cDNA was cloned by cDNA library screening or PCR. The inventors attempted to produce a fatty acid composition by transforming it into a highly proliferative host cell such as yeast, and succeeded in cloning a gene for a novel ACC capable of producing a fatty acid composition different from those produced by hosts expressing conventional ACCs, and finally accomplished the present invention. Accordingly, the present invention provides the following aspects:

(1) A nucleic acid of any one of (a)-(e) below:
(a) a nucleic acid that comprises a nucleotide sequence encoding a protein consisting of an amino acid sequence with deletion, substitution or addition of one or more amino acids in the amino acid sequence shown in SEQ ID NO: 2, and having acetyl-CoA carboxylase activity;
(b) a nucleic acid that hybridizes under stringent conditions to a nucleic acid consisting of a nucleotide sequence complementary to the nucleotide sequence of SEQ ID NO: 1 and that comprises a nucleotide sequence encoding a protein having acetyl-CoA carboxylase activity;
(c) a nucleic acid that comprises a nucleotide sequence sharing an identity of 80% or more with the nucleotide sequence consisting of SEQ ID NO: 1 and encoding a protein having acetyl-CoA carboxylase activity;
(d) a nucleic acid that comprises a nucleotide sequence encoding a protein consisting of an amino acid sequence sharing an identity of 80% or more with the amino acid sequence consisting of SEQ ID NO: 2 and having acetyl-CoA carboxylase activity; and
(e) a nucleic acid that hybridizes under stringent conditions to a nucleic acid consisting of a nucleotide sequence complementary to a nucleotide sequence encoding a protein consisting of the amino acid sequence shown in SEQ ID NO: 2 and that comprises a nucleotide sequence encoding a protein having acetyl-CoA carboxylase activity.

(2) The nucleic acid of (1), which is any one of (a)-(e) below:
(a) a nucleic acid that comprises a nucleotide sequence encoding a protein consisting of an amino acid sequence with deletion, substitution or addition of 1-200 amino acids in the amino acid sequence shown in SEQ ID NO: 2, and having acetyl-CoA carboxylase activity;
(b) a nucleic acid that hybridizes under conditions of 2×SSC, 50° C. to a nucleic acid consisting of a nucleotide sequence complementary to the nucleotide sequence of SEQ ID NO: 1 and that comprises a nucleotide sequence encoding a protein having acetyl-CoA carboxylase activity; and
(c) a nucleic acid that comprises a nucleotide sequence sharing an identity of 90% or more with the nucleotide sequence consisting of SEQ ID NO: 1 and encoding a protein having acetyl-CoA carboxylase activity;
(d) a nucleic acid that comprises a nucleotide sequence encoding a protein consisting of an amino acid sequence sharing an identity of 90% or more with the amino acid sequence consisting of SEQ ID NO: 2 and having acetyl-CoA carboxylase activity; and
(e) a nucleic acid that hybridizes under conditions of 2×SSC, 50° C. to a nucleic acid consisting of a nucleotide sequence complementary to a nucleotide sequence encoding a protein consisting of the amino acid sequence shown in SEQ ID NO: 2 and that comprises a nucleotide sequence encoding a protein having acetyl-CoA carboxylase activity.

(3) A nucleic acid of any one of (a)-(c) below:
(a) a nucleic acid that comprises the nucleotide sequence shown in SEQ ID NO: 1 or a fragment thereof;
(b) a nucleic acid that comprises a nucleotide sequence encoding a protein consisting of the amino acid sequence shown in SEQ ID NO: 2 or a fragment thereof;
(c) a nucleic acid that comprises the nucleotide sequence shown in SEQ ID NO: 4 or a fragment thereof.

(4) A nucleic acid of any one of (a)-(e) below:
(a) a nucleic acid that comprises a nucleotide sequence encoding a protein consisting of an amino acid sequence with deletion, substitution or addition of one or more amino acids in the amino acid sequence shown in SEQ ID NO: 2, and having the activity of complementing acetyl-CoA carboxylase deficiency of yeast;
(b) a nucleic acid that hybridizes under stringent conditions to a nucleic acid consisting of a nucleotide sequence complementary to the nucleotide sequence of SEQ ID NO: 1 and that comprises a nucleotide sequence encoding a protein having the activity of complementing acetyl-CoA carboxylase deficiency of yeast;
(c) a nucleic acid that comprises a nucleotide sequence sharing an identity of 80% or more with the nucleotide sequence consisting of SEQ ID NO: 1 and encoding a protein having the activity of complementing acetyl-CoA carboxylase deficiency of yeast;
(d) a nucleic acid that comprises a nucleotide sequence encoding a protein consisting of an amino acid sequence sharing an identity of 80% or more with the amino acid sequence consisting of SEQ ID NO: 2 and having the activity of complementing acetyl-CoA carboxylase deficiency of yeast; and
(e) a nucleic acid that hybridizes under stringent conditions to a nucleic acid consisting of a nucleotide sequence complementary to a nucleotide sequence encoding a protein consisting of the amino acid sequence shown in SEQ ID NO: 2 and that comprises a nucleotide sequence encoding a protein having the activity of complementing acetyl-CoA carboxylase deficiency of yeast.

(5) The nucleic acid of (4), which is any one of (a)-(e) below:
(a) a nucleic acid that comprises a nucleotide sequence encoding a protein consisting of an amino acid sequence with deletion, substitution or addition of 1-200 amino acids in the amino acid sequence shown in SEQ ID NO: 2, and having the activity of complementing acetyl-CoA carboxylase deficiency of yeast;
(b) a nucleic acid that hybridizes under conditions of 2×SSC, 50° C. to a nucleic acid consisting of a nucleotide sequence complementary to the nucleotide sequence of SEQ ID NO: 1 and that comprises a nucleotide sequence encoding a protein having the activity of complementing acetyl-CoA carboxylase deficiency of yeast;
(c) a nucleic acid that comprises a nucleotide sequence sharing an identity of 90% or more with the nucleotide sequence consisting of SEQ ID NO: 1 and encoding a protein having the activity of complementing acetyl-CoA carboxylase deficiency of yeast;
(d) a nucleic acid that comprises a nucleotide sequence encoding a protein consisting of an amino acid sequence sharing an identity of 90% or more with the amino acid sequence consisting of SEQ ID NO: 2 and having the activity of complementing acetyl-CoA carboxylase deficiency of yeast; and
(e) a nucleic acid that hybridizes under conditions of 2×SSC, 50° C. to a nucleic acid consisting of a nucleotide sequence complementary to a nucleotide sequence encoding a protein consisting of the amino acid sequence shown in SEQ ID NO:

2 and that comprises a nucleotide sequence encoding a protein having the activity of complementing acetyl-CoA carboxylase deficiency of yeast.

(6) A protein of (a) or (b) below:
(a) a protein consisting of an amino acid sequence with deletion, substitution or addition of one or more amino acids in the amino acid sequence of SEQ ID NO: 2, and having acetyl-CoA carboxylase activity; or
(b) a protein consisting of an amino acid sequence sharing an identity of 80% or more with the amino acid sequence consisting of SEQ ID NO: 2 and having acetyl-CoA carboxylase activity.

(7) A protein of (a) or (b) below:
(a) a protein consisting of an amino acid sequence with deletion, substitution or addition of 1-200 amino acids in the amino acid sequence of SEQ ID NO: 2, and having acetyl-CoA carboxylase activity; or
(b) a protein consisting of an amino acid sequence sharing an identity of 90% or more with the amino acid sequence of SEQ ID NO: 2 and having acetyl-CoA carboxylase activity.

(8) A protein of (a) or (b) below:
(a) a protein consisting of an amino acid sequence with deletion, substitution or addition of one or more amino acids in the amino acid sequence of SEQ ID NO: 2, and having the activity of complementing acetyl-CoA carboxylase deficiency of yeast; or
(b) a protein consisting of an amino acid sequence sharing an identity of 80% or more with the amino acid sequence consisting of SEQ ID NO: 2 and having the activity of complementing acetyl-CoA carboxylase deficiency of yeast.

(9) A protein of (a) or (b) below:
(a) a protein consisting of an amino acid sequence with deletion, substitution or addition of 1-200 amino acids in the amino acid sequence of SEQ ID NO: 2, and having the activity of complementing acetyl-CoA carboxylase deficiency of yeast; or
(b) a protein consisting of an amino acid sequence sharing an identity of 90% or more with the amino acid sequence consisting of SEQ ID NO: 2 and having the activity of complementing acetyl-CoA carboxylase deficiency of yeast.

(10) A protein consisting of the amino acid sequence shown in SEQ ID NO: 2.

(11) A recombinant vector comprising the nucleic acid of any one of (1)-(5).

(12) A cell transformed with the recombinant vector of (11).

(13) A fatty acid composition obtained by culturing the transformed cell of (12).

(14) A method for preparing the fatty acid composition of (13), comprising collecting the fatty acid composition from cultures of the transformed cell of (12).

(15) A food product comprising the fatty acid composition of (13).

(16) A nucleic acid of any one of (a)-(e) below:
(a) a nucleic acid that comprises a nucleotide sequence encoding a protein consisting of an amino acid sequence with deletion, substitution or addition of one or more amino acids in the amino acid sequence shown in SEQ ID NO: 2, and having the activity of increasing the arachidonic acid content inherent in a host;
(b) a nucleic acid that hybridizes under stringent conditions to a nucleic acid consisting of a nucleotide sequence complementary to the nucleotide sequence of SEQ ID NO: 1 and that comprises a nucleotide sequence encoding a protein having the activity of increasing the arachidonic acid content inherent in a host;
(c) a nucleic acid that comprises a nucleotide sequence sharing an identity of 80% or more with the nucleotide sequence consisting of SEQ ID NO: 1 and encoding a protein having the activity of increasing the arachidonic acid content inherent in a host;
(d) a nucleic acid that comprises a nucleotide sequence encoding a protein consisting of an amino acid sequence sharing an identity of 80% or more identity to the amino acid sequence consisting of SEQ ID NO: 2 and having the activity of increasing the arachidonic acid content inherent in a host; and
(e) a nucleic acid that hybridizes under stringent conditions to a nucleic acid consisting of a nucleotide sequence complementary to a nucleotide sequence encoding a protein consisting of the amino acid sequence shown in SEQ ID NO: 2 and that comprises a nucleotide sequence encoding a protein having the activity of increasing the arachidonic acid content inherent in a host.

(17) A protein of (a) or (b) below:
(a) a protein consisting of an amino acid sequence with deletion, substitution or addition of one or more amino acids in the amino acid sequence of SEQ ID NO: 2, and having the activity of increasing the arachidonic acid content inherent in a host; or
(b) a protein consisting of an amino acid sequence sharing an identity of 80% or more with the amino acid sequence consisting of SEQ ID NO: 2 and having the activity of increasing the arachidonic acid content inherent in a host.

Additionally, the present invention also encompasses the following aspects:

(A) A nucleic acid of any one of (a)-(e) below:
(a) a nucleic acid that comprises a nucleotide sequence encoding a protein consisting of an amino acid sequence with deletion, substitution or addition of 1-200 amino acids in the amino acid sequence shown in SEQ ID NO: 2, and having the activity of changing the content of fatty acids or compositional ratio of fatty acids inherent in a host;
(b) a nucleic acid that hybridizes under stringent conditions, preferably under conditions of 2×SSC, 50° C. to a nucleic acid consisting of a nucleotide sequence complementary to the nucleotide sequence of SEQ ID NO: 1 and that comprises a nucleotide sequence encoding a protein having the activity of changing the content of fatty acids or compositional ratio of fatty acids inherent in a host;
(c) a nucleic acid that comprises a nucleotide sequence sharing an identity of 80% or more, preferably 90% or more, with the nucleotide sequence of SEQ ID NO: 1 and encoding a protein having the activity of changing the content of fatty acids or compositional ratio of fatty acids inherent in a host;
(d) a nucleic acid that comprises a nucleotide sequence encoding a protein consisting of an amino acid sequence sharing an identity of 80% or more, preferably 90% or more, with the amino acid sequence of SEQ ID NO: 2 and having the activity of changing the content of fatty acids or compositional ratio of fatty acids inherent in a host; and
(e) a nucleic acid that hybridizes under stringent conditions, preferably under conditions of 2×SSC, 50° C. to a nucleic acid consisting of a nucleotide sequence complementary to a nucleotide sequence encoding a protein consisting of the amino acid sequence shown in SEQ ID NO: 2 and that comprises a nucleotide sequence encoding a protein having the activity of changing the content of fatty acids or compositional ratio of fatty acids inherent in a host.

(B) A protein of (a) or (b) below:
(a) a protein consisting of an amino acid sequence with deletion, substitution or addition of 1-200 amino acids in the amino acid sequence of SEQ ID NO: 2, and having the activity of changing the content of fatty acids or compositional ratio of fatty acids inherent in a host; or (b) a protein consisting of an amino acid sequence sharing an identity of 80% or more, preferably 90% or more, with the amino acid sequence of SEQ ID NO: 2 and having the activity of changing the content of fatty acids or compositional ratio of fatty acids inherent in a host.

Additionally, the present invention also encompasses: (C) a recombinant vector comprising any one of the nucleic acids shown in (A); (D) a cell transformed with the recombinant vector; (E) a fatty acid composition obtained by culturing the transformed cell having changed content of fatty acids or compositional ratio of fatty acids as compared with those inherent in cultures of a host not transformed with the recombinant vector of (C); (F) a method for preparing the fatty acid composition (E), comprising collecting the fatty acid composition (E) from cultures of the transformed cell of (D); and (G) a food product comprising the fatty acid composition (E).

Advantageous Effects of Invention

The ACC of the present invention allows an improvement in the ability to produce fatty acids and/or reserve lipids, and hence is preferred as means for improving the productivity of polyunsaturated fatty acids in microorganisms and plants. Thus, they can provide lipids having desired characteristics or effects so that they are useful for use in foods, cosmetics, pharmaceuticals, soaps, etc.

BRIEF DESCRIPTION OF DRAWINGS

FIG. 1A shows the full-length cDNA sequence (SEQ ID NO: 4) of ACC from *M. alpina* strain 1S-4 and the amino acid sequence (SEQ ID NO: 2) deduced therefrom.

FIG. 1B shows the full-length cDNA sequence (SEQ ID NO: 4 continued) of ACC from *M. alpina* strain 1S-4 and the amino acid sequence (SEQ ID NO: 2 continued) deduced therefrom.

FIG. 1C shows the full-length cDNA sequence (SEQ ID NO: 4 continued) of ACC from *M. alpina* strain 1S-4 and the amino acid sequence (SEQ ID NO: 2 continued) deduced therefrom.

FIG. 1D shows the full-length cDNA sequence (SEQ ID NO: 4 continued) of ACC from *M. alpina* strain 1S-4 and the amino acid sequence (SEQ ID NO: 2 continued) deduced therefrom.

FIG. 2A shows a comparison between the full-length cDNA sequence of ACC from *M. alpina* strain 1S-4 (SEQ ID NO: 4) and the nucleic acid sequence of a fragment of an ACC homolog from a known *M. alpina* strain CBS528.72 (SEQ ID NO: 24).

FIG. 2B shows a comparison between the full-length cDNA sequence of ACC from *M. alpina* strain 1S-4 (SEQ ID NO: 4 continued) and the nucleic acid sequence of a fragment of an ACC homolog from a known *M. alpina* strain CBS528.72 (SEQ ID NO: 24 continued).

FIG. 2C shows a comparison between the full-length cDNA sequence of ACC from *M. alpina* strain 1S-4 (SEQ ID NO: 4 continued) and the nucleic acid sequence of a fragment of an ACC homolog from a known *M. alpina* strain CBS528.72 (SEQ ID NO: 24 continued).

FIG. 2D shows a comparison between the full-length cDNA sequence of ACC from *M. alpina* strain 1S-4 (SEQ ID NO: 4 continued) and the nucleic acid sequence of a fragment of an ACC homolog from a known *M. alpina* strain CBS528.72 (SEQ ID NO: 24 continued).

FIG. 3A shows a comparison between the amino acid sequence (SEQ ID NO: 2) deduced from the full-length cDNA sequence of ACC from *M. alpina* strain 1S-4 and the amino acid sequence (SEQ ID NO: 25) deduced from a cDNA fragment of ACC from *M. alpina* strain CBS528.72.

FIG. 3B shows a comparison between the amino acid sequence (SEQ ID NO: 2 continued) deduced from the full-length cDNA sequence of ACC from *M. alpina* strain 1S-4 and the amino acid sequence (SEQ ID NO: 25 continued) deduced from a cDNA fragment of ACC from *M. alpina* strain CBS528.72.

FIG. 3C shows a comparison between the amino acid sequence (SEQ ID NO: 2 continued) deduced from the full-length cDNA sequence of ACC from *M. alpina* strain 1S-4 and the amino acid sequence (SEQ ID NO: 25 continued) deduced from a cDNA fragment of ACC from *M. alpina* strain CBS528.72.

FIG. 4A shows a comparison of the amino acid sequence (SEQ ID NO: 2) deduced from the full-length cDNA sequence of ACC from *M. alpina* strain 1S-4 with the amino acid sequence (SEQ ID NO: 34) of cytoplasmic ACC Acc1p and the amino acid sequence (SEQ ID NO: 35) of mitochondrial ACC Hfa1p from the yeast *Saccharomyces cerevisiae*.

FIG. 4B shows a comparison of the amino acid sequence (SEQ ID NO: 2 continued) deduced from the full-length cDNA sequence of ACC from *M. alpina* strain 1S-4 with the amino acid sequence (SEQ ID NO: 34 continued) of cytoplasmic ACC Acc1p and the amino acid sequence (SEQ ID NO: 35 continued) of mitochondrial ACC Hfa1p from the yeast *Saccharomyces cerevisiae*.

FIG. 4C shows a comparison of the amino acid sequence (SEQ ID NO: 2 continued) deduced from the full-length cDNA sequence of ACC from *M. alpina* strain 1S-4 with the amino acid sequence (SEQ ID NO: 34 continued) of cytoplasmic ACC Acc1p and the amino acid sequence (SEQ ID NO: 35 continued) of mitochondrial ACC Hfa1p from the yeast *Saccharomyces cerevisiae*.

FIG. 4D shows a comparison of the amino acid sequence (SEQ ID NO: 2 continued) deduced from the full-length cDNA sequence of ACC from *M. alpina* strain 1S-4 with the amino acid sequence (SEQ ID NO: 34 continued) of cytoplasmic ACC Acc1p and the amino acid sequence (SEQ ID NO: 35 continued) of mitochondrial ACC Hfa1p from the yeast *Saccharomyces cerevisiae*.

FIG. 4E shows a comparison of the amino acid sequence (SEQ ID NO: 2 continued) deduced from the full-length cDNA sequence of ACC from *M. alpina* strain 1S-4 with the amino acid sequence (SEQ ID NO: 34 continued) of cytoplasmic ACC Acc1p and the amino acid sequence (SEQ ID NO: 35 continued) of mitochondrial ACC Hfa1p from the yeast *Saccharomyces cerevisiae*.

DESCRIPTION OF EMBODIMENTS

Figure 5:
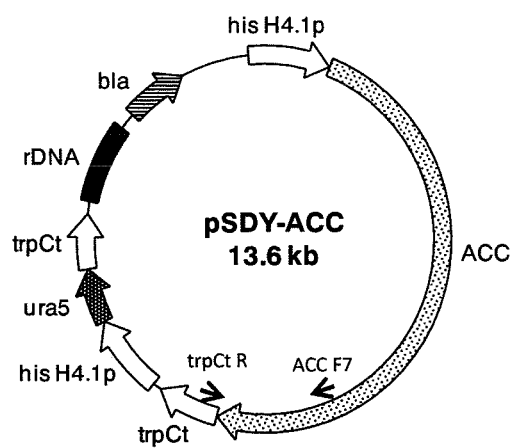
FIG. 5 is a schematic diagram showing plasmid pSDY-ACC. In the figure, hisH4.1p represents the promoter of the histone H4.1 gene from *M. alpina*, trpCt represents the terminator of the trpC gene from *Aspergillus nidulans*, ura5 represents the ura5 gene from *M. alpina*, and rDNA represents a part of 18S rDNA from *M. alpina*. The arrows (→) in the schematic diagram indicate the positions of the primers ACC-F7 and trpCt-R used for identifying transformed strains.

The present invention relates to a novel acetyl-CoA carboxylase from the genus *Mortierella*, characterized by catalyzing the reaction of producing malonyl-CoA via ATP-dependent carboxylation of acetyl-CoA.

The reaction of producing malonyl-CoA from acetyl-CoA mediated by the acetyl-CoA carboxylase of the present invention (hereinafter also referred to as "ACC") is a key rate-limiting step in fatty acid biosynthesis. This means that ACC is a crucial enzyme responsible for supplying malonyl-CoA that is an important intermediate in fatty acid synthesis. Specifically, ACC is an enzyme catalyzing the following reaction:

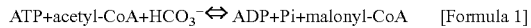   [Formula 1]

Thus, they catalyze the reaction of producing malonyl-CoA via ATP-dependent carboxylation of acetyl-CoA. This reaction takes place in the two steps below.

[Formula 2]

   (1)

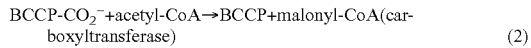   (2)

BCCP*:biotin carboxyl carrier protein

The malonyl-CoA produced by this reaction serves as a substrate for de novo fatty acid synthesis reaction or fatty acid chain elongation reaction to generate various fatty acids. In this manner, the ACC of the present invention is known to play an important role in controlling fatty acid biosynthesis or lipid metabolism.

The malonyl-CoA produced by the ACC of the present invention is a substrate for fatty acid synthesis, as described above, and the rate at which this malonyl-CoA is produced determines the rate of in vivo fatty acid biosynthesis. Specifically, de novo fatty acid synthesis starts from acetyl-CoA to synthesize new fatty acids by adding two carbon atoms via decarboxylative coupling with malonyl-CoA in a series of condensation-reduction-dehydration-reduction reactions. For example, palmitic acid containing 16 carbon atoms is produced by seven cycles of the series of condensation-reduction-dehydration-reduction reactions, and two carbon atoms at the methyl end of this palmitic acid are derived from acetyl-CoA and the others are derived from malonyl-CoA. Malonyl-CoA is not only an intermediate in fatty acid biosynthesis but also an intermediate in polyketide biosynthesis.

Furthermore, the acetyl-CoA carboxylase of the present invention have the activity of complementing acetyl-CoA carboxylase deficiency of yeast, as explained in detail below.

Nucleic Acids Encoding the Acetyl-CoA Carboxylase of the Present Invention

Sequences related to the acetyl-CoA carboxylase of the present invention (ACC) include SEQ ID NO: 1 representing the ORF region of ACC from *M. alpina* 1S-4; SEQ ID NO: 2 representing its amino acid sequence; SEQ ID NO: 3 representing the CDS region; SEQ ID NO: 4 representing the nucleotide sequence of cDNA; and SEQ ID NO: 5 representing the genomic nucleotide sequence. More specifically, SEQ ID NO: 3 corresponds to nucleotides 45-6734 of SEQ ID NO: 4, and SEQ ID NO: 1 corresponds to nucleotides 45-6731 of SEQ ID NO: 4 and nucleotides 1-6684 of SEQ ID NO: 3. The genomic sequence of SEQ ID NO: 5 contains five introns and exon regions corresponding to nucleotides 1-27, 315-665, 1271-2828, 2917-3463, 3590-6239, and 6339-7889 of SEQ ID NO: 5.

The nucleic acids of the present invention include single-stranded and double-stranded DNAs as well as RNA complements thereof, and may be either naturally occurring or artificially prepared. DNAs include, but are not limited to, genomic DNAs, cDNAs corresponding to the genomic DNAs, chemically synthesized DNAs, PCR-amplified DNAs and combinations thereof, as well as DNA/RNA hybrids, for example.

Preferred embodiments of the nucleic acids of the present invention include (a) a nucleic acid that comprises the nucleotide sequence shown in SEQ ID NO: 1; (b) a nucleic acid that comprises a nucleotide sequence encoding a protein consisting of the amino acid sequence shown in SEQ ID NO: 2; (c) a nucleic acid that comprises the nucleotide sequence shown in SEQ ID NO: 4; or (d) a nucleic acid that comprises the nucleotide sequence shown in SEQ ID NO: 5, etc.

To obtain the above nucleotide sequences, nucleotide sequence data of EST or genomic DNA from an organism having ACC activity can be searched for nucleotide sequences encoding proteins sharing high identity to a known protein having ACC activity. The organism having ACC activity is preferably a lipid-producing fungus such as, but not limited to, *M. alpina*.

To perform EST analysis, a cDNA library is first constructed. Procedures for cDNA library construction can be found in "Molecular Cloning, A Laboratory Manual 3rd ed." (Cold Spring Harbor Press (2001)). Commercially available cDNA library construction kits may also be used. A procedure for cDNA library construction suitable for the present invention is as follows, for example. That is, an appropriate strain of a lipid-producing fungus *M. alpina* is inoculated into an appropriate medium and precultured for an appropriate period. Culture conditions suitable for this pre-culture include a medium composition of 1.8% glucose, 1% yeast extract, pH 6.0 for an incubation period of 3 days at an incubation temperature of 28° C., for example. The pre-cultured product is then subjected to main culture under appropriate conditions. A culture medium composition suitable for the main culture may comprise, for example, 1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$, pH 6.0. Incubation conditions suitable for the main culture include incubation with aeration and agitation at 300 rpm, 1 vvm, 26° C. for 8 days, for example. An appropriate amount of glucose may be added during the incubation period. The cultures are collected at appropriate time points during the main culture and cells are harvested to prepare total RNA. Total RNA can be prepared using a known technique such as the guanidine hydrochloride/CsCl method. Poly(A)$^+$ RNA can be purified from the resulting total RNA using a commercially available kit. Further, a cDNA library can be constructed using a commercially available kit. Then, ESTs can be obtained by determining the nucleotide sequences of any clones from the constructed cDNA library, by using primers designed to allow sequencing of an insert on a vector. For example, directional cloning can be performed when the cDNA library has been constructed using a ZAP-cDNA Giga-packIII Gold Cloning Kit (STRATAGENE).

As a result of homology analysis using BLASTX against amino acid sequences deposited in GenBank, the cDNA sequence of the ACC of the present invention showed homology to ACC homologs of eukaryotic microorganisms. Among known amino acid sequences, the putative protein RO3G_04977 from *Rhizopus oryzae* showed the highest identity and the nucleotide sequence identity and amino acid sequence identity between the CDS encoding this protein and the CDS of the ACC of the present invention determined by clustalW are 65.5% and 66.3%, respectively. The identities to the putative amino acid sequences of ACC homologs from other fungi are 58.8% to a homolog from *Neurospora crassa* (accession number EAA33781), 58.3% to a homolog from *Aspergillus fumigatus* (accession number EAL93163), and 55.1% to the cytoplasmic ACC Acc1p (SEQ ID NO: 34) and 44.7% to the mitochondrial ACC Hfa1p (SEQ ID NO: 35) of the yeast *Saccharomyces cerevisiae*.

As for the ACC gene from *M. alpina*, a fragment of an ACC homolog from CBS528.72 strain has been known and previously deposited in Genbank (nucleic acid sequence: accession number AJ586915 (non-patent document 6); amino acid sequence: accession number CAE52914). The CDS region from CBS528.72 strain corresponds to nucleotides 342-1439 of SEQ ID NO: 1, and its amino acid sequence corresponds to amino acids 100-465 of SEQ ID NO: 4. As compared with these sequences, the CDS region from CBS528.72 strain in the cDNA from *M. alpina* 1S-4 newly obtained has 91.3% nucleotide sequence identity and 97.8% amino acid sequence identity. In the cDNA from *M. alpina* 1S-4 of the present invention, the sequences of undisclosed regions in the known CBS528.72 strain have not been reported yet, and therefore, the complete sequence of the ACC gene of *M. alpina* was first elucidated by the present invention. The sequences of regions newly elucidated were shown to contain multiple regions or other elements crucial for the function of ACC, specifically a biotin carboxyl carrier protein domain, a carboxyltransferase domain, a conserved biotin acceptor protein domain and biotin acceptor residues, all of which are essential for the activity of ACC.

The present invention also encompasses nucleic acids functionally equivalent to a nucleic acid that comprises the nucleotide sequence shown in SEQ ID NO: 1 above (herein also referred to as "the nucleotide sequence of the present invention") or a nucleotide sequence encoding a protein consisting of the amino acid sequence shown in SEQ ID NO: 2 (herein also referred to as "the amino acid sequence of the present invention"). The expression "functionally equivalent" means that a protein encoded by the nucleotide sequence of the present invention and a protein consisting of the amino acid sequence of the present invention have ACC activity. ACC activity can be assayed by known methods including, for example, the method described in J.B.C., 279, 21779-21786, 2004.

In addition to the above ACC activity, the protein encoded by the nucleotide sequence of the present invention or the protein consisting of the amino acid sequence of the present invention may also be a protein having the activity of complementing ACC deficiency of yeast (hereinafter also referred to as "a protein having the activity of complementing yeast ACC deficiency of the present invention"). The ACC of yeast (*S. cerevisiae*) is localized in the cytoplasm and mitochondria, of which the ACC1 gene encoding ACC present in the cytoplasm is known to be an essential gene whose deletion leads to death (Biochim. Biophys. Acta, 1771, 255-270, 2007). In other words, yeast lacking the ACC1 gene cannot grow normally, but it is complemented and can grow when a gene functionally equivalent to the ACC1 gene is expressed.

In this connection, the method for confirming that yeast ACC deficiency has been complemented by the ACC of the present invention may be any method for confirming that ACC activity has been restored in an ACC-deficient strain of yeast when an ACC gene of the present invention is expressed. As a specific example, the following method can be used for the ACC1 gene encoding the cytoplasmic ACC, for example.

Thus, a heterozygous strain lacking only one of alleles of the ACC1 gene encoding cytoplasmic ACC in diploid yeast is prepared, and then a strain carrying an expression cassette of an ACC gene of the present invention on a chromosome other than the one carrying ACC1 is prepared, as also specifically explained in Example 4 below. These strains are spread on sporulation plates to form ascospores. The resulting cells can be subjected to random spore analysis or tetrad analysis to select spore-derived haploid strains. The haploid yeast thus obtained is genotyped to assess that otherwise non-viable ACC1-deficient strains can grow only in the presence of an expression cassette of the ACC gene of the present invention, indicating that the ACC of the present invention could complement ACC activity in *S. cerevisiae*.

In addition to the ACC activity above, the protein encoded by the nucleotide sequence of the present invention or the protein consisting of the amino acid sequence of the present invention may also be a protein having the activity of changing the arachidonic acid content or fatty acid composition inherent in a host. Thus, when a host cell is transformed with a nucleic acid encoding the protein of the present invention and the protein is expressed, the amount or compositional ratio of fatty acids produced by the transformed cell can be changed as compared with those of non-transformed host cells. The host used herein can be any member of the list shown in the section of "Construction of vectors for expressing the ACC of the present invention and preparation of transformed cells" below. The fatty acids produced by the host may be those shown in the section "Fatty acid compositions of the present invention" below.

Such nucleic acids functionally equivalent to the nucleic acids of the present invention include a nucleic acid of any one of (a)-(e) below. As used herein below, "the above activity of the present invention" refers to "ACC activity, the activity of complementing yeast ACC deficiency of the present invention, and/or the activity of changing the arachidonic acid content or fatty acid composition inherent in a host" defined above.

(a) A nucleic acid that comprises a nucleotide sequence encoding a protein consisting of an amino acid sequence with deletion, substitution or addition of one or more amino acids in the amino acid sequence shown in SEQ ID NO: 2, and having the above activity of the present invention.

The nucleic acid of the present invention comprises a nucleotide sequence encoding a protein consisting of an amino acid sequence with deletion, substitution or addition of one or more amino acids in the amino acid sequence shown in SEQ ID NO: 2, and having the above activity of the present invention.

Specifically, it comprises a nucleotide sequence encoding a protein consisting of:
(i) an amino acid sequence with deletion of one or more (preferably one or several (e.g., 1-400, 1-200, 1-100, 1-50, 1-30, 1-25, 1-20, 1-15, more preferably 10, 9, 8, 7, 6, 5, 4, 3, 2, or 1)) amino acids in the amino acid sequence shown in SEQ ID NO: 2;
(ii) an amino acid sequence with substitution of other amino acids for one or more (preferably one or several (e.g., 1-400, 1-200, 1-100, 1-50, 1-30, 1-25, 1-20, 1-15, more preferably 10, 9, 8, 7, 6, 5, 4, 3, 2, or 1)) amino acids in the amino acid sequence shown in SEQ ID NO: 2;
(iii) an amino acid sequence with addition of other one or more (preferably one or several (e.g., 1-400, 1-200, 1-100, 1-50, 1-30, 1-25, 1-20, 1-15, more preferably 10, 9, 8, 7, 6, 5, 4, 3, 2, or 1)) amino acids in the amino acid sequence shown in SEQ ID NO: 2; or (iv) an amino acid sequence with any combination of (i)-(iii) above; and having the above activity of the present invention.

Among the above modifications, the substitution is preferably conservative. Conservative substitution refers to replacement of a particular amino acid residue by another residue having similar physicochemical characteristics, and may be any substitution that does not substantially change the structural characteristics of the original sequence, e.g., it may be any substitution so far as the substituted amino acids do not disrupt a helix present in the original sequence or do not disrupt any other type of secondary structure characteristic of the original sequence.

Conservative substitution is typically introduced by synthesis in biological systems or chemical peptide synthesis, preferably by chemical peptide synthesis. Substituents here may include unnatural amino acid residues, as well as peptidomimetics, and reversed or inverted forms of amino acid sequences in which unsubstituted regions are reversed or inverted.

A non-limitative list of groups of amino acid residues that can be substituted for each other is shown below.

Group A: leucine, isoleucine, norleucine, valine, norvaline, alanine, 2-aminobutanoic acid, methionine, O-methylserine, t-butylglycine, t-butylalanine and cyclohexylalanine;
Group B: aspartic acid, glutamic acid, isoaspartic acid, isoglutamic acid, 2-aminoadipic acid and 2-aminosuberic acid;
Group C: asparagine and glutamine;
Group D: lysine, arginine, ornithine, 2,4-diaminobutanoic acid and 2,3-diaminopropionic acid;
Group E: proline, 3-hydroxyproline and 4-hydroxyproline;
Group F: serine, threonine and homoserine; and
Group G: phenylalanine and tyrosine.

Non-conservative substitution may include replacement of a member of one of the above groups by a member of another group, in which case, the hydropathic indices of amino acids (amino acid hydropathic indices) should preferably be considered in order to retain biological functions of the proteins of the present invention (Kyte et al., J. Mol. Biol., 157:105-131 (1982)).

Non-conservative substitution may also include amino acid replacement based on hydrophilicity.

In the specification and drawings herein, nucleotide and amino acid notions and abbreviations are based on the IUPAC-IUB Commission on Biochemical Nomenclature or protocols conventionally used in the art as described, for example, in Immunology—A Synthesis (second edition, edited by E. S. Golub and D. R. Gren, Sinauer Associates, Sunderland, Mass. (1991)). Any optical isomers of amino acids that may exist refer to L-isomers, unless otherwise specified.

Stereoisomers of the above amino acids such as D-amino acids, unnatural amino acids such as α,α-disubstituted amino acids, N-alkylamino acids, lactic acid, and other non-canonical amino acids may also constitute the proteins of the present invention.

Proteins are herein written with the amino-terminus on the left and the carboxy-terminus on the right in accordance with standard usage and convention in the art.

Similarly and normally, single-stranded polynucleotide sequences are written with the 5'-end on the left end and double-stranded polynucleotide sequences are written with the 5'-end of one strand on the left, unless otherwise specified.

One skilled in the art will be able to design and generate suitable variants of the proteins described herein using techniques known in the art. For example, one may identify suitable areas of the protein molecule that may be structurally changed without destroying biological activity of a protein of the present invention by targeting areas not believed to be important for the biological activity of the protein of the present invention. Also, one may identify residues and areas conserved between similar proteins. Furthermore, one will be able to introduce conservative amino acid substitutions into areas that may be important for the biological activity or structure of the protein of the present invention without destroying the biological activity and without adversely affecting the polypeptide structure of the protein.

Figure 4A:
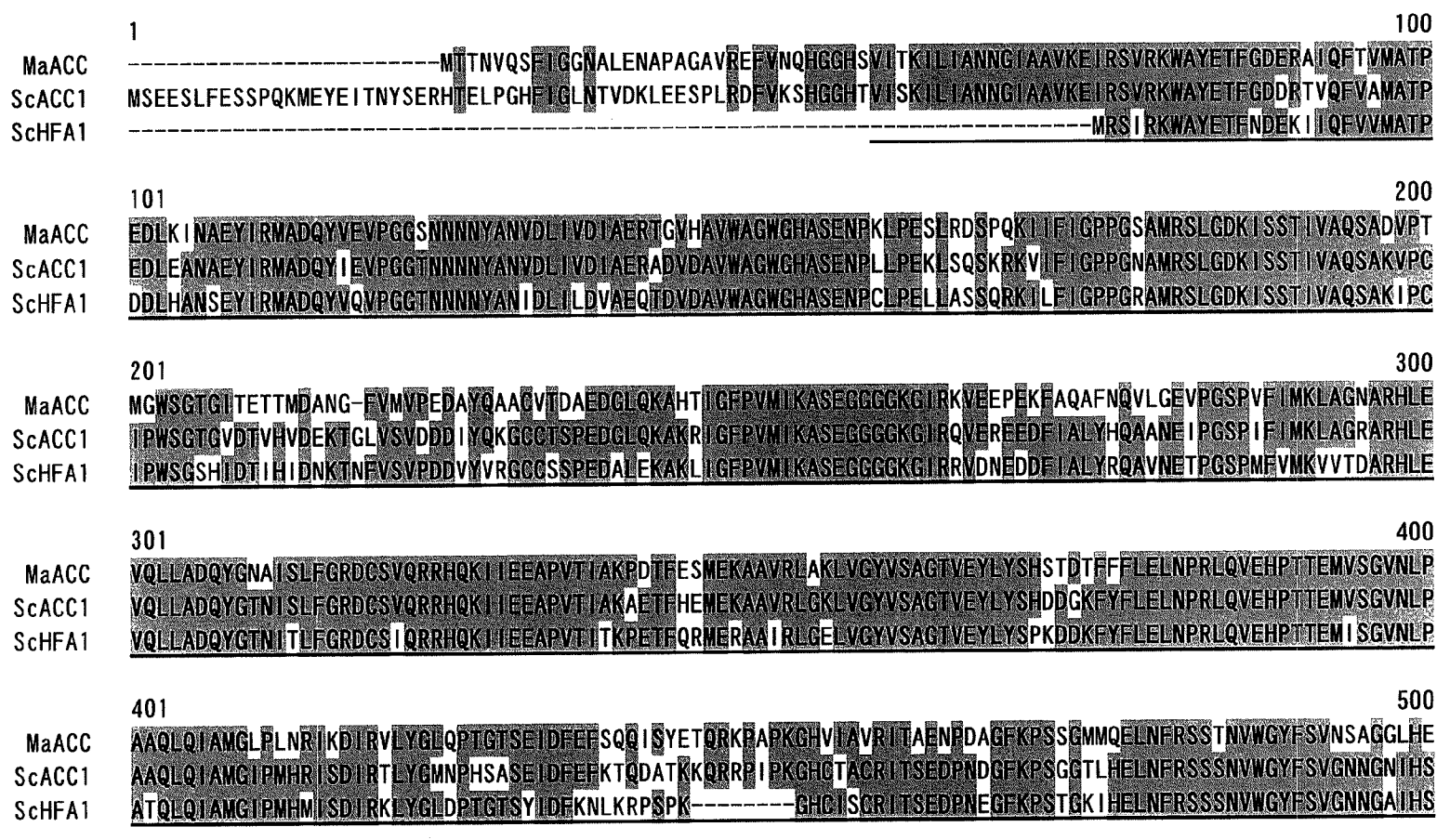
Figure 4B:
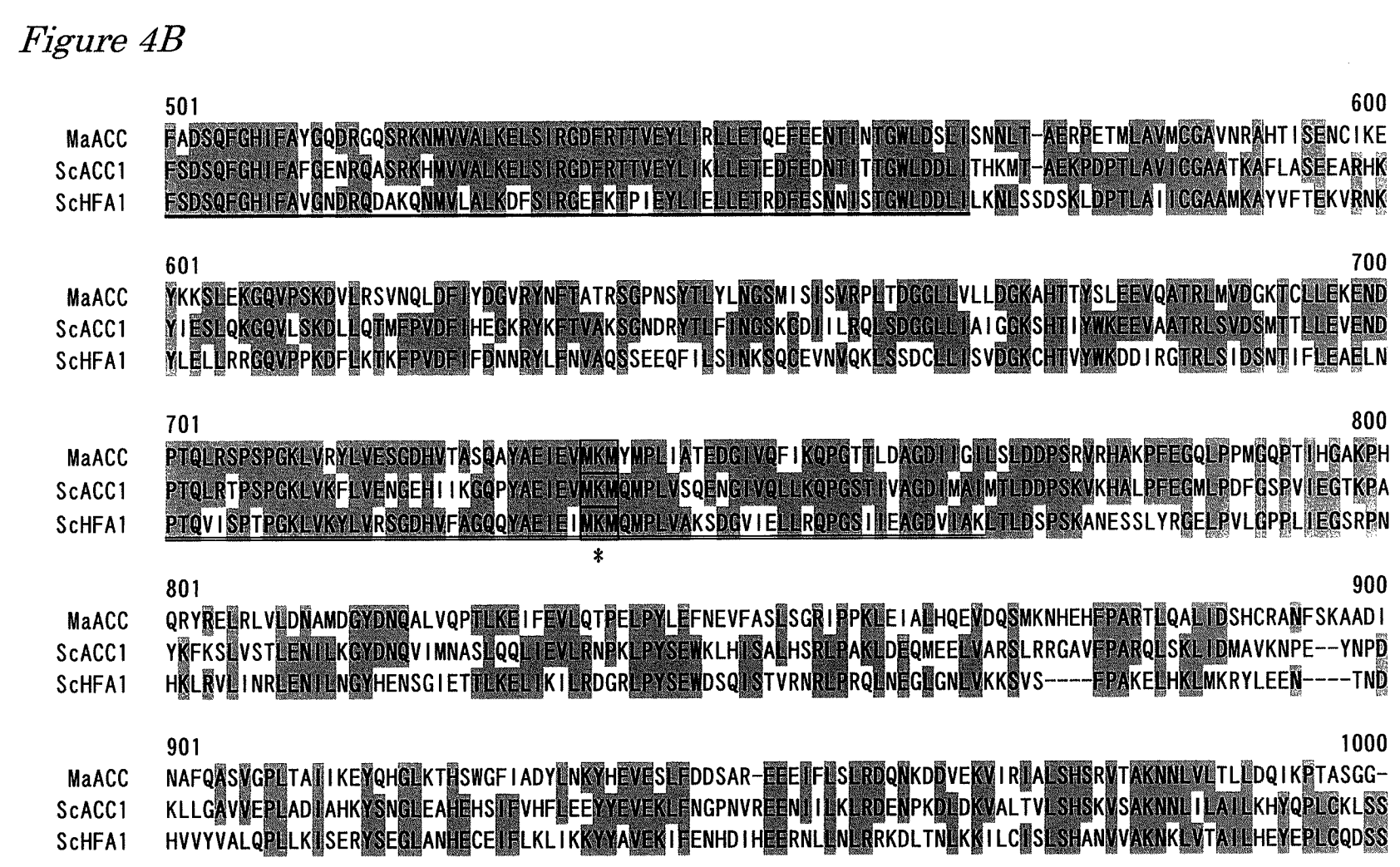
Figure 4D:
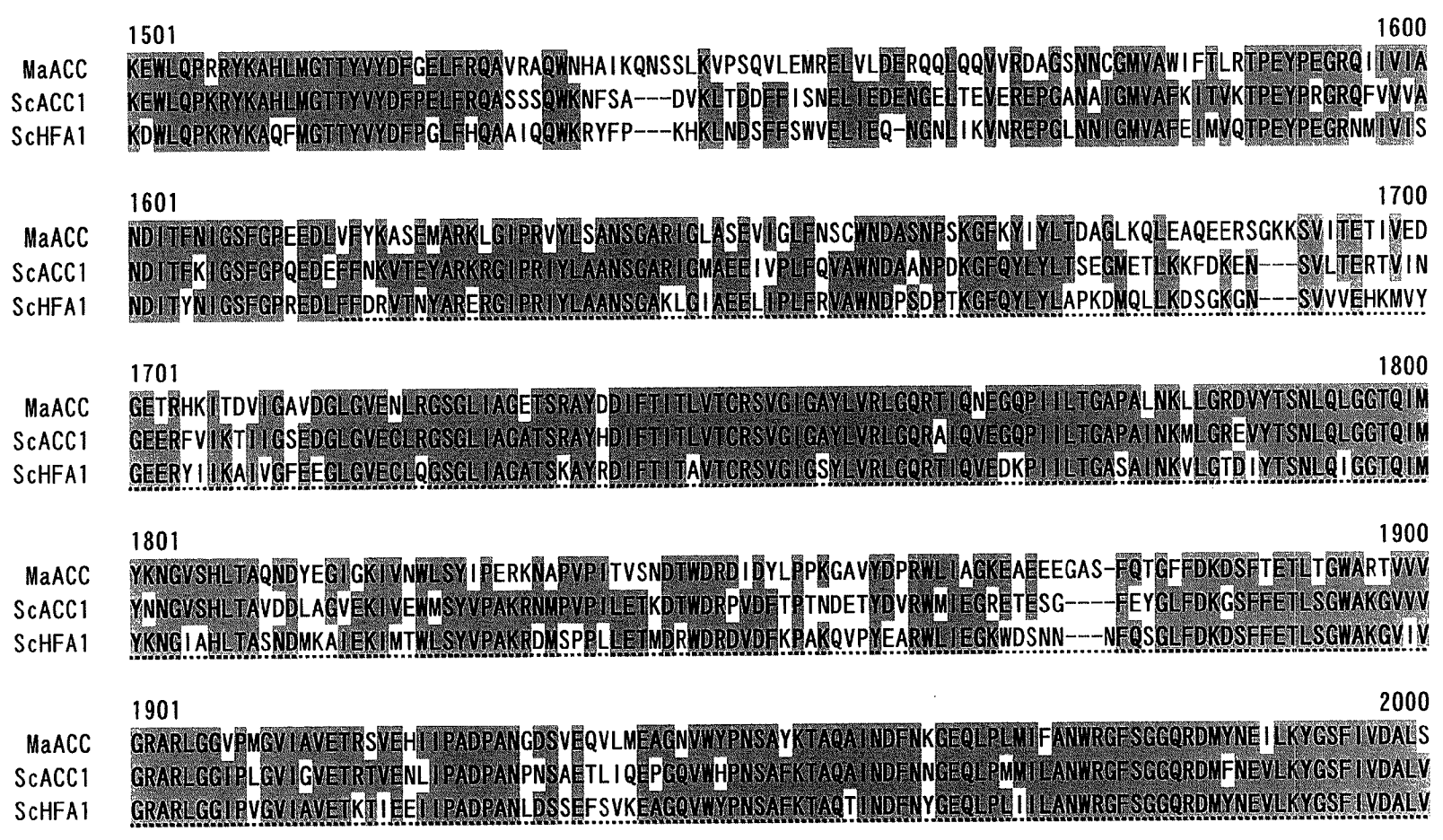

Especially, the amino acid sequence of the ACC of the present invention contains a conserved motif of biotin-containing enzymes called "MKM motif". This motif is essential for ACC and conserved in the amino acid sequences of biotin-containing enzymes, and corresponds to amino acid residues 736-738 in FIG. 4. As shown, FIG. 4 compares the amino acid sequences of ACC from *M. alpina* and ACC1 from yeast. In FIG. 4, the single underline indicates biotin-carboxylase (BC) domains, the double underline indicates biotin carboxyl carrier protein (BCCP) domains, and the broken underline indicates carboxyltransferase (CT) domains. K (Lys) residues marked with an asterisk represent biotin acceptor residues, and boxed regions indicate the MKM motif. Accordingly, variants of the present invention may be any variant so far as the above conserved motif is conserved and the above activity of the present invention is not impaired.

One skilled in the art can perform so-called structure-function studies identifying residues of a peptide similar to a peptide of the protein of the present invention that are important for biological activity or structure of said protein, and comparing the amino acid residues in the two peptides to predict which residues in a protein similar to the protein of the present invention are amino acid residues that correspond to amino acid residues that are important for biological activity or structure. Further, one may choose variants that retain the biological activity of the protein of the present invention by opting for chemically similar amino acid substitutions for such predicted amino acid residues. One skilled in the art can also analyze the three-dimensional structure and amino acid sequence of the variants of the protein. In view of the analytical results, one may further predict the alignment of amino acid residues with respect to the three-dimensional structure of the protein. Based on the analytical results as described above, one skilled in the art may also generate variants containing no changes to amino acid residues predicted to be on the surface of the protein, since such residues may be involved in important interactions with other molecules. Moreover, one skilled in the art may generate variants containing a single amino acid substitution among the amino acid residues constituting the protein of the present invention. The variants can be screened by known assays to gather information about the individual variants. As a result, one may evaluate usefulness of the individual amino acid residues constituting the protein of the present invention by comparing variants containing a substitution of a particular amino acid residue to assess whether they show reduced biological activity as compared with the biological activity of the protein of the present invention, or they show no such biological activity, or they show unsuitable activity inhibiting the biological activity of the protein of the present invention. Moreover, based on information gathered from such routine experiments, one skilled in the art can readily analyze undesirable amino acid substitutions for variants of the protein of the present invention either alone or in combination with other mutations.

As described above, proteins consisting of an amino acid sequence with deletion, substitution, or addition of one or more amino acids in the amino acid sequence shown in SEQ ID NO: 2, can be prepared by such techniques as site-directed mutagenesis as described in "Molecular Cloning, A Laboratory Manual 3rd ed." (Cold Spring Harbor Press (2001)); "Current Protocols in Molecular Biology" (John Wiley & Sons (1987-1997); Kunkel (1985) Proc. Natl. Acad. Sci. USA 82: 488-92; Kunkel (1988) Method. Enzymol. 85: 2763-6, etc. Preparation of such variants containing amino acid deletions, substitutions or additions or the like can be carried out by known procedures such as, for example, the Kunkel method or the Gapped duplex method, using a mutation-introducing kit based on site-directed mutagenesis such as, for example, a QuikChange™ Site-Directed Mutagenesis Kit (Stratagene), a GeneTailor™ Site-Directed Mutagenesis System (Invitrogen) or a TaKaRa Site-Directed Mutagenesis System (Mutan-K, Mutan-Super Express Km, etc.; Takara Bio Inc.).

In addition to the site-directed mutagenesis mentioned above, techniques for introducing deletion, substitution or addition of one or more amino acids in the amino acid sequences of proteins while retaining their activity may include a method of treating a gene with a mutagen, and a method comprising selective cleavage of a gene to remove, substitute or add a selected nucleotide followed by ligation.

The nucleotide sequence that the nucleic acid of the present invention comprises is preferably a nucleotide sequence encoding a protein consisting of an amino acid sequence with deletion, substitution, or addition of 1-200 amino acids in the amino acid sequence shown in SEQ ID NO: 2, and having ACC activity.

The nucleotide sequence that the nucleic acid of the present invention comprises also includes a nucleotide sequence encoding a protein consisting of an amino acid sequence with deletion, substitution, or addition of 1-200 amino acids in the amino acid sequence shown in SEQ ID NO: 2, and having the above activity of the present invention. There is no limitation on the number or sites of amino acid changes or modifications in the protein of the present invention so far as the above activity of the present invention is retained. The method for assaying the above activity of the present invention is as described above.

(b) A nucleic acid that hybridizes under stringent conditions to a nucleic acid consisting of a nucleotide sequence complementary to the nucleotide sequence of SEQ ID NO: 1 and that comprises a nucleotide sequence encoding a protein having the above activity of the present invention.
The nucleic acid of the present invention hybridizes under stringent conditions to a nucleic acid consisting of a nucleotide sequence complementary to the nucleotide sequence of SEQ ID NO: 1 and comprises a nucleotide sequence encoding a protein having the above activity of the present invention. SEQ ID NO: 1 and ACC activity are as described above.

The above nucleotide sequence can be obtained from a cDNA library and a genomic library or the like by a known hybridization technique such as colony hybridization, plaque hybridization or Southern blotting using a probe prepared from an appropriate fragment by a method known to those skilled in the art.

Detailed procedures for hybridization can be found in "Molecular Cloning, A Laboratory Manual 3rd ed." (Cold Spring Harbor Press (2001); especially Sections 6-7); "Current Protocols in Molecular Biology" (John Wiley & Sons (1987-1997); especially Sections 6.3-6.4); "DNA Cloning 1: Core Techniques, A Practical Approach 2nd ed." (Oxford University (1995); especially Section 2.10 for hybridization conditions), etc.

The strength of hybridization conditions is determined primarily by hybridization conditions, more preferably by hybridization conditions and washing conditions. As used herein, "stringent conditions" include moderately or highly stringent conditions.

Specifically, moderately stringent conditions include, for example, hybridization conditions of 1×SSC-6×SSC at 42° C.-55° C., more preferably 1×SSC-3×SSC at 45° C.-50° C., most preferably 2×SSC at 50° C. When the hybridization solution contains about 50% formamide, for example, temperatures 5-15° C. below the temperatures indicated above are used. Washing conditions include 0.5×SSC-6×SSC at 40° C.-60° C. During hybridization and washing, typically 0.05-0.2%, preferably about 0.1% SDS may be added.

Highly stringent (high stringent) conditions include hybridization and/or washing at higher temperatures and/or lower salt concentrations than those of the moderately stringent conditions. For example, hybridization conditions include 0.1×SSC-2×SSC at 55° C.-65° C., more preferably 0.1×SSC-1×SSC at 60° C.-65° C., most preferably 0.2×SSC at 63° C. Washing conditions include 0.2×SSC-2×SSC at 50° C.-68° C., more preferably 0.2×SSC at 60-65° C.

Hybridization conditions specifically used in the present invention include for example, but are not limited to, prehybridization in 5×SSC, 1% SDS, 50 mM Tris-HCl (pH 7.5) and 50% formamide at 42° C. followed by hybridization with a probe at 42° C. overnight, and then washing three times in 0.2×SSC, 0.1% SDS at 65° C. for 20 minutes.

Commercially available hybridization kits using no radioactive probe can also be used. Specifically, hybridization may be performed using a DIG nucleic acid detection kit (Roche Diagnostics) or an ECL direct labeling & detection system (Amersham), etc.

Nucleic acids encompassed within the present invention preferably include a nucleic acid that hybridizes under conditions of 2×SSC, 50° C. to a nucleic acid consisting of a nucleotide sequence complementary to the nucleotide sequence of SEQ ID NO: 1 and comprises a nucleotide sequence encoding a protein having ACC activity.

(c) A nucleic acid that comprises a nucleotide sequence sharing an identity of 80% or more with the nucleotide sequence consisting of SEQ ID NO: 1 and encoding a protein having the above activity of the present invention.
The nucleotide sequence that the nucleic acids of the present invention comprises shares an identity of at least 80% with the nucleotide sequence shown in SEQ ID NO: 1 and encodes a protein having the above activity of the present invention.

Preferably, the nucleic acid comprises a nucleotide sequence sharing an identity of at least 80%, more preferably 85%, still more preferably 90% (e.g., 92% or more, still more preferably 95% or more, even 97%, 98% or 99%) with the nucleotide sequence shown in SEQ ID NO: 1 and encoding a protein having the above activity of the present invention.

The percent identity between two nucleic acid sequences can be determined by visual inspection and mathematical calculation, or preferably by comparing sequence information of the two nucleic acids using a computer program. Computer programs for sequence comparison include, for example, the BLASTN program (Altschul et al. (1990) J. Mol. Biol. 215: 403-10) version 2.2.7 available from the website of the U.S. National Library of Medicine: http://www.ncbi.nlm.nih.gov/blast/bl2seq/bls.html, or the WU-BLAST 2.0 algorithm, etc. Standard default parameter settings for WU-BLAST 2.0 are available at the following Internet site: http://blast.wustl.edu.

(d) A nucleic acid that comprises a nucleotide sequence encoding a protein consisting of an amino acid sequence sharing an identity of 80% or more with the amino acid sequence consisting of SEQ ID NO: 2 and having the above activity of the present invention.

The nucleic acid of the present invention comprises a nucleotide sequence encoding a protein consisting of an amino acid sequence sharing an identity of 80% or more with the amino acid sequence consisting of SEQ ID NO: 2 and having the above activity of the present invention. The protein encoded by the nucleic acid of the present invention may be ACC or a protein having identity to the amino acid sequence of ACC so far as it is functionally equivalent to a protein having the above activity of the present invention.

Specifically, the amino acid sequence shares an identity of 80% or more, preferably 85% or more, more preferably 90%, still more preferably 95% or more, even more preferably 97% (e.g., 98%, even 99%) or more with the amino acid sequence of SEQ ID NO: 2 or the like.

The nucleic acid of the present invention preferably comprises a nucleotide sequence encoding a protein consisting of an amino acid sequence sharing an identity of 95% or more with the amino acid sequence of SEQ ID NO: 2 and having the above activity of the present invention. More preferably, the nucleic acid comprises a nucleotide sequence encoding a protein consisting of an amino acid sequence sharing an identity of 98% or more with the amino acid sequence of SEQ ID NO: 2 and having the above activity of the present invention.

The percent identity between two amino acid sequences can be determined by visual inspection and mathematical calculation. Alternatively, the percent identity can be determined by using a computer program. Such computer programs include, for example, BLAST, FASTA (Altschul et al., J. Mol. Biol., 215:403-410 (1990)) and ClustalW, etc. In particular, various conditions (parameters) for an identity search with the BLAST program are described by Altschul et al. (Nucl. Acids. Res., 25, p. 3389-3402, 1997) and publicly available from the website of the National Center for Biotechnology Information (NCBI) or the DNA Data Bank of Japan (DDBJ) (BLAST Manual, Altschul et al., NCB/NLM/NIH Bethesda, Md. 20894; Altschul et al.). The percent identity can also be determined using genetic information processing programs such as GENETYX Ver. 7 (Genetyx), DNASIS Pro (Hitachisoft), Vector NTI (Infomax), etc.

Certain alignment schemes for aligning amino acid sequences may result in the matching of even a specific short region of the sequences, and thereby it is possible to detect a region with very high sequence identity in such a small aligned region, even when there is no significant relationship between the full-length sequences used. In addition, the BLAST algorithm may use the BLOSUM62 amino acid scoring matrix and optional parameters as follows: (A) inclusion of a filter to mask off segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 554-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported).

(e) A nucleic acid that hybridizes under stringent conditions to a nucleic acid consisting of a nucleotide sequence complementary to a nucleotide sequence encoding a protein consisting of the amino acid sequence shown in SEQ ID NO: 2 and that comprises a nucleotide sequence encoding a protein having the above activity of the present invention. The nucleic acid of the present invention hybridizes under stringent conditions to a nucleic acid consisting of a nucleotide sequence complementary to a nucleotide sequence encoding a protein consisting of the amino acid sequence shown in SEQ ID NO: 2 and comprises a nucleotide sequence encoding a protein having the above activity of the present invention.

The protein consisting of the amino acid sequence shown in SEQ ID NO: 2 and hybridization conditions are as described above. The nucleic acid of the present invention includes a nucleic acid that hybridizes under stringent conditions to a nucleic acid consisting of a nucleotide sequence complementary to a nucleotide sequence encoding a protein consisting of the amino acid sequence shown in SEQ ID NO: 2 and that comprises a nucleotide sequence encoding a protein having the above activity of the present invention.

The nucleic acid of the present invention also includes a nucleic acid that comprises a nucleotide sequence with deletion, substitution or addition of one or more nucleotides in the nucleotide sequence consisting of SEQ ID NO: 1, and encoding a protein having the above activity of the present invention. Specifically, it is also possible to use a nucleic acid which comprises a nucleotide sequences selected from:

(i) a nucleotide sequence with deletion of one or more (preferably one or several (e.g., 1-1500, 1-1000, 1-500, 1-300, 1-250, 1-200, 1-150, 1-100, 1-50, 1-30, 1-25, 1-20, 1-15, more preferably 10, 9, 8, 7, 6, 5, 4, 3, 2, or 1)) nucleotides in the nucleotide sequence shown in SEQ ID NO: 1;

(ii) a nucleotide sequence with substitution of other nucleotides for one or more (preferably one or several (e.g., 1-1500, 1-1000, 1-500, 1-300, 1-250, 1-200, 1-150, 1-100, 1-50, 1-30, 1-25, 1-20, 1-15, more preferably 10, 9, 8, 7, 6, 5, 4, 3, 2, or 1)) nucleotides in the nucleotide sequence shown in SEQ ID NO: 1;

(iii) a nucleotide sequence with addition of other one or more (preferably one or several (e.g., 1-1500, 1-1000, 1-500, 1-300, 1-250, 1-200, 1-150, 1-100, 1-50, 1-30, 1-25, 1-20, 1-15, more preferably 10, 9, 8, 7, 6, 5, 4, 3, 2, or 1)) nucleotides in the nucleotide sequence shown in SEQ ID NO: 1; or (iv) a nucleotide sequence with any combination of (i)-(iii) above; and encoding a protein having the above activity of the present invention.

Preferred embodiments of the nucleic acids of the present invention also include a nucleic acid of any one of (a)-(c) below:

(a) a nucleic acid that comprises the nucleotide sequence shown in SEQ ID NO: 1 or a fragment thereof;

(b) a nucleic acid that comprises a nucleotide sequence encoding the amino acid sequence shown in SEQ ID NO: 2 or a fragment thereof;

(c) a nucleic acid that comprises the nucleotide sequence shown in SEQ ID NO: 4 or a fragment thereof.

The (a) nucleic acid that comprises the nucleotide sequence shown in SEQ ID NO: 1; (b) nucleic acid that comprises a nucleotide sequence encoding a protein consisting of the amino acid sequence shown in SEQ ID NO: 2; and (c) nucleic acid that comprises the nucleotide sequence shown in SEQ ID NO: 4 are as described above. The fragments of the above sequences are regions contained in the above nucleotide sequences including ORFs, CDSs, biologically active regions, regions used as primers as described below, and regions capable of serving as probes, and may be naturally occurring or artificially prepared.

The nucleic acids of the present invention also include:
(1) (a) a nucleic acid that comprises a nucleotide sequence encoding a protein consisting of an amino acid sequence with deletion, substitution, or addition of one or more amino acids in the amino acid sequence shown in SEQ ID NO: 2;
(b) a nucleic acid that hybridizes under stringent conditions to a nucleic acid consisting of a nucleotide sequence complementary to the nucleotide sequence consisting of SEQ ID NO: 1;
(c) a nucleic acid that comprises a nucleotide sequence consisting of a nucleotide sequence sharing an identity of 80% or more with the nucleotide sequence consisting of SEQ ID NO: 1 and encoding a protein;
(d) a nucleic acid that comprises a nucleotide sequence encoding a protein consisting of an amino acid sequence sharing an identity of 80% or more with the amino acid sequence consisting of SEQ ID NO: 2;
(e) a nucleic acid that hybridizes under stringent conditions to a nucleic acid consisting of a nucleotide sequence complementary to a nucleotide sequence encoding a protein consisting of the amino acid sequence shown in SEQ ID NO: 2; and
(2) the nucleic acid of (1), which is any one of (a)-(e):
(a) a nucleic acid that comprises a nucleotide sequence encoding a protein consisting of an amino acid sequence with deletion, substitution or addition of 1-200 amino acids in the amino acid sequence shown in SEQ ID NO: 2;
(b) a nucleic acid that hybridizes under conditions of 2×SSC, 50° C. to a nucleic acid consisting of a nucleotide sequence complementary to the nucleotide sequence of SEQ ID NO: 1;
(c) a nucleic acid that comprises a nucleotide sequence sharing an identity of 90% or more with the nucleotide sequence consisting of SEQ ID NO: 1;
(d) a nucleic acid that comprises a nucleotide sequence encoding a protein consisting of an amino acid sequence sharing an identity of 90% or more with the amino acid sequence consisting of SEQ ID NO: 2;
(e) a nucleic acid that hybridizes under conditions of 2×SSC, 50° C. to a nucleic acid consisting of a nucleotide sequence complementary to a nucleotide sequence encoding a protein consisting of the amino acid sequence shown in SEQ ID NO: 2.

Acetyl-CoA Carboxylase Proteins of the Present Invention

The proteins of the present invention include a protein consisting of the amino acid sequence shown in SEQ ID NO: 2 and functionally equivalent proteins to this protein, and may be naturally occurring or artificially prepared. The protein consisting of the amino acid sequence shown in SEQ ID NO: 2 is as described above. The "functionally equivalent proteins" refer to proteins having "the above activity of the present invention," as explained above in the section "Nucleic acids encoding the acetyl-CoA carboxylase of the present invention".

In the present invention, the functionally equivalent proteins to a protein consisting of the amino acid sequence shown in SEQ ID NO: 2 include a protein shown in (a) or (b) below:
(a) a protein consisting of an amino acid sequence with deletion, substitution or addition of one or more amino acids in the amino acid sequence of SEQ ID NO: 2, and having the above activity of the present invention;
(b) a protein consisting of an amino acid sequence sharing an identity of 80% or more with the amino acid sequence consisting of SEQ ID NO: 2 and having the above activity of the present invention.

Here, the amino acid sequence with deletion, substitution or addition of one or more amino acids in the amino acid sequence of SEQ ID NO: 2 or the amino acid sequence sharing an identity of 80% or more with the amino acid sequence of SEQ ID NO: 2 is as explained above in the section "Nucleic acids encoding the acetyl-CoA carboxylase of the present invention". The "protein having the above activity of the present invention" also includes a variant of a protein encoded by a nucleic acid comprising the nucleotide sequence of SEQ ID NO: 1, or a variant of a protein containing multiple types of modifications such as substitution, deletion or addition of one or more amino acids in the amino acid sequence shown in SEQ ID NO: 2, or a modified protein having a modified amino acid side chain, or a fusion protein with another protein and having ACC activity and/or the activity of complementing yeast ACC deficiency the present invention and/or the activity of forming a compositional ratio of fatty acids of the present invention.

The proteins of the present invention may be artificially prepared by chemical synthesis techniques such as Fmoc method (fluorenylmethyloxycarbonyl method) and tBoc method (t-butyloxycarbonyl method). They can also be chemically synthesized using a peptide synthesizer available from Advanced ChemTech, Perkin Elmer, Pharmacia, Protein Technology Instrument, Synthecell-Vega, PerSeptive, Shimadzu Corporation or the like.

The proteins of the present invention also include:
(1) (a) a protein consisting of an amino acid sequence with deletion, substitution or addition of one or more amino acids in the amino acid sequence of SEQ ID NO: 2;
(b) a protein consisting of an amino acid sequence sharing an identity of 80% or more with the amino acid sequence consisting of SEQ ID NO: 2;
(2) a protein of (a) or (b) below:
(a) a protein consisting of an amino acid sequence with deletion, substitution or addition of 1-200 amino acids in the amino acid sequence of SEQ ID NO: 2;
(b) a protein consisting of an amino acid sequence sharing an identity of 90% or more with the amino acid sequence of SEQ ID NO: 2.

Cloning of the Nucleic Acids of the Present Invention

The nucleic acids for the ACC of the present invention can be cloned by, for example, screening from a cDNA library using an appropriate probe. They can also be cloned by PCR amplification with appropriate primers followed by ligation to an appropriate vector. The clone may further be subcloned into another vector.

For example, commercially available plasmid vectors can be used, such as pBlue-Script™ SK (+) (Stratagene), pGEM-T (Promega), pAmp (TM: Gibco-BRL), p-Direct (Clontech) and pCR2.1-TOPO (Invitrogen). For amplification by PCR, any regions of the nucleotide sequences shown in SEQ ID NO: 1 and the like above may be used as primers, such as for example,

```
                                              (SEQ ID NO: 6)
upstream primer:    5'-GCCAACTGGCGTGGATTCTC-3'
and
                                              (SEQ ID NO: 7)
downstream primer:  5'-GTCCTCGTTGATAGTAGGGTC-3'.
```

PCR is performed by adding the above primers and a heat-resistant DNA polymerase or the like to act on cDNA prepared from *M. alpina* cells. Although this procedure can be readily accomplished by those skilled in the art according to, e.g., "Molecular Cloning, A Laboratory Manual 3rd ed."

(Cold Spring Harbor Press (2001)), PCR conditions in the present invention may be set as follows:
Denaturation temperature: 90-95° C.
Annealing temperature: 40-60° C.
Elongation temperature: 60-75° C.
Number of cycles: 10 or more.

The resulting PCR product can be purified using known methods. For example, these methods use kits such as GENECLEAN (Funakoshi Co., Ltd.), QIAquick PCR purification Kits (QIAGEN), ExoSAP-IT (GE Healthcare Bio-Sciences); or DEAE-cellulose filters or dialysis tubes, etc. When an agarose gel is used, the PCR products are subjected to agarose gel electrophoresis and nucleic acid fragments are excised from the agarose gel, followed by purification with GENECLEAN (Funakoshi Co., Ltd.), QIAquick Gel extraction Kits (QIAGEN), a freeze-squeeze method, etc.

The nucleotide sequences of the cloned nucleic acids can be determined using a nucleotide sequencer.

Construction of Vectors for Expressing ACC of the Present Invention and Preparation of Transformed Cells The present invention also provides recombinant vectors comprising a nucleic acid encoding the ACC of the present invention. The present invention further provides cells transformed with the recombinant vectors.

Such recombinant vectors and transformed cells can be obtained as follows. Namely, a plasmid carrying a nucleic acid encoding the ACC of the present invention is digested with restriction endonucleases. The restriction endonucleases used include for example, but not limited to, EcoRI, KpnI, BamHI and SalI, etc. The plasmid may be blunt-ended by T4 polymerase treatment. The digested nucleotide fragment is purified by agarose gel electrophoresis. This fragment may be inserted into an expression vector by a known method, thereby giving a vector for expressing ACC. This expression vector is transformed into a host to generate a transformed cell, which is used for the expression of a desired protein.

The expression vector and host here are not specifically limited so far as a desired protein can be expressed, and hosts include fungi, bacteria, plants and animals or cells thereof, for example. Fungi include filamentous fungi such as a lipid-producing fungus *M. alpina*, yeast such as *Saccharomyces cerevisiae*, etc. Bacteria include *Escherichia coli*, *Bacillus subtilis*, etc. Further, plants include oil-producing plants such as rapeseed, soybean, cotton, safflower and flax.

Lipid-producing fungi that can be used include, for example, strains described in MYCOTAXON, Vol. XLIV, NO. 2, pp. 257-265 (1992), specifically microorganisms belonging to the genus *Mortierella*, including microorganisms belonging to the subgenus *Mortierella* such as *Mortierella elongata* (*M. elongata*) IFO8570, *Mortierella exigua* (*M. exigua*) IFO8571, *Mortierella hygrophila* (*M. hygrophila*) IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70, CBS754.68, or microorganisms belonging to the subgenus *Micromucor* such as *Mortierella isabellina* (*M. isabellina*) CBS194.28, IFO6336, IFO7824, IFO7873, IFO7874, IFO8286, IFO8308, IFO7884, *Mortierella nana* (*M. nana*) IFO8190, *Mortierella ramanniana* (*M. ramanniana*) IFO5426, IFO8186, CBS112.08, CBS212.72, IFO7825, IFO8184, IFO8185, IFO8287, *Mortierella vinacea* (*M. vinacea*) CBS236.82. Among others, *M. alpina* is preferred.

When a fungus is used as a host, the vector preferably has a structure that allows a nucleic acid of the present invention to be self-replicable in the host or to be inserted onto a chromosome of the fungus. Also, it preferably contains a promoter and a terminator. When *M. alpina* is used as a host, the expression vector may be, for example, pD4, pDuraSC, pDura5 or the like. Any promoter that can be expressed in the host may be used, including *M. alpina*-derived promoters such as the promoter of the histone H4.1 gene, the promoter of the GAPDH (glyceraldehyde-3-phosphate dehydrogenase) gene and the promoter of the TEF (translation elongation factor) gene.

Techniques for transforming a recombinant vector into filamentous fungi such as *M. alpina* include electroporation, the spheroplast method, particle delivery, and direct microinjection of DNA into nuclei, etc. When an auxotrophic host strain is used, transformed strains can be obtained by selecting strains growing on a selective medium lacking its essential nutrients. When a drug resistance marker gene is used for transformation, cell colonies showing drug resistance can be obtained by culturing in a selective medium containing the drug.

When yeast is used as a host, the expression vector may be, for example, pYE22m or the like. Commercially available yeast expression vectors such as pYES (Invitrogen) and pESC (STRATAGENE) may also be used. Yeast hosts suitable for the present invention include, but are not limited to, *S. cerevisiae* strain EH13-15 (trp1, MATα), etc. Promoters used include, for example, those derived from yeast or the like, such as GAPDH promoter, GAL1 promoter and GAL10 promoter.

Techniques for transforming a recombinant vector into yeast include, for example, the lithium acetate method, electroporation, the spheroplast method, dextran-mediated transfection, calcium phosphate precipitation, polybrene-mediated transfection, protoplast fusion, encapsulation of (one or more) polynucleotide(s) in liposomes, and direct microinjection of DNA into nuclei, etc.

When a bacterium such as *E. coli* is used as a host, the expression vector may be, for example, pGEX, pUC18 or the like available from Pharmacia. Promoters that can be used include those derived from *E. coli*, phages and the like, such as trp promoter, lac promoter, PL promoter and PR promoter, for example. Techniques for transforming a recombinant vector into bacteria include, for example, electroporation and the calcium chloride method.

Methods for Preparing Fatty Acid Compositions of the Present Invention

The present invention provides methods for preparing a fatty acid composition from the transformed cell described above. That is, methods for preparing a fatty acid composition from cultured product obtained by culturing the above transformed cell. Specifically, it can be prepared by the procedure described below. However, the present methods are not limited to the following procedures, and can also be carried out by using other conventional known procedures.

Any culture medium may be used for culturing ACC-expressing organisms so far as it has appropriate pH and osmotic pressure and contains nutrients required for growth of each host, trace elements, and biological materials such as sera or antibiotics. For example, media that can be used for yeast cells transformed to express ACC include, but not limited to, SC-Trp medium, YPD medium, YPD5 medium and the like. As a composition of a specific medium, SC-Trp medium is exemplified: it contains per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil).

Any culture conditions suitable for host growth and adequate for stably maintaining the generated enzyme may be used, and specifically, various conditions can be adjusted, including anaerobicity, incubation period, temperature, humidity, static or shaking culture, etc. Cultivation may be performed under the same conditions (one-step culture) or may be so-called two-step or three-step culture using two or more different culture conditions, but two-step culture and the like are preferred for large-scale culture, because of high culture efficiency.

As a specific method for preparing a fatty acid composition of the present invention using yeast as a host in two-step culture is exemplified and illustrated below. That is, as a pre-culture, colonies obtained as above are inoculated into the above SC-Trp medium or the like, for example, and precultured with shaking at 30° C. for 2 days. Then, as a main culture, 500 µl of the preculture is added to 10 ml of YPD5 (2% yeast extract, 1% polypeptone, 5% glucose) medium, and cultured with shaking at 30° C. for 2 days.

Fatty Acid Composition of the Present Invention

The present invention also provides a fatty acid composition, which is an assembly of one or more fatty acids in a cell expressing the ACC of the present invention. Preferably, it provides a fatty acid composition obtained by culturing a transformed cell expressing the ACC of the present invention. The fatty acids may be free fatty acids or triglycerides, phospholipids or the like.

The fatty acids contained in the fatty acid composition of the present invention are linear or branched monocarboxylic acids of long-chain carbohydrates, including for example, but not limited to, myristic acid (tetradecanoic acid) (14:0), myristoleic acid (tetradecenoic acid) (14:1), palmitic acid (hexadecanoic acid) (16:0), palmitoleic acid (9-hexadecenoic acid) (16:1), stearic acid (octadecanoic acid) (18:0), oleic acid (cis-9-octadecenoic acid) (18:1 (9)), vaccenic acid (11-octadecenoic acid) (18:1 (11)), linolic acid (cis,cis-9,12 octadecadienoic acid) (18:2 (9,12)), α-linolenic acid (9,12,15-octadecatrienoic acid) (18:3 (9,12,15)), γ-linolenic acid (6,9,12-octadecatrienoic acid) (18:3 (6,9,12)), stearidonic acid (6,9,12,15-octadecatetraenoic acid) (18:4 (6,9,12,15)), arachidic acid (icosanoic acid) (20:0), (8,11-icosadienoic acid) (20:2 (8,11)), mead acid (5,8,11-icosatrienoic acid) (20:3 (5,8,11)), dihomo-γ-linolenic acid (8,11,14-icosatrienoic acid) (20:3 (8,11,14)), arachidonic acid (5,8,11,14-icosatetraenoic acid) (20:4 (5,8,11,14)), eicosatetraenoic acid (8,11,14,17-icosatetraenoic acid) (20:4 (8,11,14,17)), eicosapentaenoic acid (5,8,11,14,17-icosapentaenoic acid) (20:5 (5,8,11,14,17)), behenic acid (docosanoic acid) (22:0), (7,10,13,16-docosatetraenoic acid) (22:4 (7,10,13,16)), (7,10,13,16,19-docosapentaenoic acid) (22:5 (7,10,13,16,19)), (4,7,10,13,16-docosapentaenoic acid) (22:5 (4,7,10,13,16)), (4,7,10,13,16,19-docosahexaenoic acid) (22:6 (4,7,10,13,16,19)), lignoceric acid (tetradocosanoic acid) (24:0), nervonic acid (cis-15-tetradocosanoic acid) (24:1), cerotic acid (hexadocosanoic acid) (26:0), etc. The chemical names shown above are common names defined by the IUPAC Biochemical Nomenclature, and each followed by the systematic name and then the number of carbon atoms and the number and positions of double bonds in parentheses.

The fatty acid composition of the present inventions may be composed of any number and any type of fatty acids so far as they comprise a combination of one or more of the fatty acids listed above.

Lyophilized cells obtained by the methods for preparing fatty acid compositions of the present invention described above are stirred with a chloroform/methanol mixture prepared in a suitable ratio, and then heated for a suitable period. Further, separation of the cells by centrifugation and solvent recovery are repeated several times. Then, lipids are dried by a suitable method and then dissolved in a solvent such as chloroform. An aliquot of this sample is collected and fatty acids in the cells are converted into methyl esters using methanolic HCl, then extracted with hexane, and hexane is distilled off and the residue is analyzed by gas chromatography. When the ACC of the present invention is expressed in yeast, for example, a fatty acid composition can be obtained, which is characterized by, in compositional ratio of fatty acids, a higher proportion of palmitoleic acid and/or docosanoic acid or a lower proportion of palmitic acid, stearic acid and/or hexadocosanoic acid than found in cultures of hosts that are not transformed with a recombinant vector of the present invention.

The ACC of the present invention sometimes has a different compositional ratio of fatty acids from those of known ACC fatty acid compositions, showing that the ACC of the present invention has a different influence from those of known ACCs on the lipid metabolism of hosts.

Food or Other Products Comprising Fatty Acid Compositions of the Present Invention The present invention also provides food products comprising the above fatty acid compositions. The fatty acid compositions of the present invention can be routinely used to produce food products and industrial raw materials containing fats and oils (raw materials for cosmetics, pharmaceuticals (e.g., topical skin medicines), soaps, etc.) or for other purposes. Cosmetics (compositions) or pharmaceuticals (compositions) may be presented in any form including, but not limited to, solution, paste, gel, solid, powder or the like. Food products may also be presented in the form of a pharmaceutical formulation such as a capsule, or a processed food such as a natural liquid diet, low residue diet, elemental diet, nutritional drink or enteral feeding formula comprising a fatty acid composition of the present invention in combination with proteins, sugars, fats, trace elements, vitamins, emulsifiers, flavorings, etc.

Other examples of food products of the present invention include, but are not limited to, dietary supplements, health foods, functional foods, diets for children, modified milk for infants, modified milk for premature infants, geriatric diets, etc. The food product as used herein collectively refers to edible products in the form of solid, fluid, liquid or a mixture thereof.

Dietary supplements refer to food products fortified with specific nutritional ingredients. Health foods refer to food products known to be healthy or good for health, and include dietary supplements, natural foods, dietetic foods, etc. Functional foods refer to food products for supplying nutritional ingredients having physiological control functions, and may also be called foods for specified health use. Diets for children refer to food products intended for children up to about 6 years of age. Geriatric diets refer to food products treated to ease digestion and absorption as compared with untreated foods. Modified milk for infants refers to modified milk intended for children up to about one year of age. Modified milk for premature infants refers to modified milk intended for premature infants of up to about 6 months of age.

These food products include natural foods such as meat, fish, nuts (treated with fats and oils); foods cooked with fats and oils such as Chinese foods, Chinese noodles, soups; foods using fats and oils as heating media such as Tempura (deep-fried fish and vegetables), deep-fried foods coated in bread-crumbs, fried bean curd, Chinese fried rice, doughnuts, Karinto (Japanese fried dough cookies); fat- and oil-based foods or food products processed with fats and oils such as butter, margarine, mayonnaise, salad dressing, chocolate, instant noodles, caramel, biscuits, cookies, cake, ice cream; and foods sprayed or coated with fats and oils during finishing such as rice crackers, hard biscuits, sweet bean paste bread. However, the food products of the present invention are not limited to fat- and oil-containing foods, but also include processed agricultural foods such as bread, noodles, cooked rice, sweets (candies, chewing gums, gummies, tablets, Japanese sweets), bean curd and processed products thereof; fermented foods such as Sake (Japanese rice wine), medicinal liquor, Mirin (sweet cooking sherry), vinegar, soy sauce and Miso (soy bean paste); livestock food products such as yogurt, ham, bacon and sausage; processed seafood products such as Kamaboko (fish cake), Ageten (deep-fried fish cake) and Hanpen (puffy fish cake); and fruit drinks, soft drinks, sports drinks, alcoholic beverages, tea and the like.

Method for Evaluating or Selecting Strains Using a Nucleic Acid Encoding ACC or an ACC Protein of the Present Invention The present invention also provides methods for evaluating or selecting lipid-producing strains using a nucleic acid encoding ACC or an ACC protein of the present invention. The methods are specifically described below.

(1) Evaluation Methods

One embodiment of the present invention is a method for evaluating a lipid-producing strain using a nucleic acid encoding ACC or an ACC protein of the present invention. The evaluation method of the present invention may comprise evaluating a lipid-producing test strain for the above activity of the present invention using a primer or probe designed on the basis of a nucleotide sequence of the present invention. General procedures for such an evaluation method are known and described in, e.g., WO01/040514 or JP HEI 8-205900 A. This evaluation method is briefly explained below.

First, the genome of a test strain is prepared. Any known preparation method can be used such as the Hereford method or potassium acetate method (see, e.g., Methods in Yeast Genetics, Cold Spring Harbor Laboratory Press, p 130 (1990)).

A primer or probe is designed on the basis of a nucleotide sequence of the present invention, preferably SEQ ID NO: 1. The primer or probe can be designed from any region of the nucleotide sequence of the present invention using known procedures. The number of nucleotides in a polynucleotide used as a primer is typically 10 or more, preferably 15 to 25. Typically, the number of nucleotides appropriate for a region to be flanked by the primers is generally 300 to 2000.

The primer or probe prepared above is used to assess whether or not the genome of the above test strain contains a sequence specific to the nucleotide sequence of the present invention. A sequence specific to the nucleotide sequence of the present invention may be detected using known procedures. For example, a polynucleotide comprising a part or all of a sequence specific to the nucleotide sequence of the present invention or a polynucleotide comprising a nucleotide sequence complementary to the above nucleotide sequence is used as one primer, and a polynucleotide comprising a part or all of a sequence upstream or downstream of this sequence or a polynucleotide comprising a nucleotide sequence complementary to the above nucleotide sequence is used as the other primer to amplify the nucleic acid of the test strain by PCR or the like, thereby determining the presence or absence of an amplified product, the molecular weight of the amplified product, etc.

PCR conditions suitable for the method of the present invention are not specifically limited, but include for example:

Denaturation temperature: 90-95° C.
Annealing temperature: 40-60° C.
Elongation temperature: 60-75° C.
Number of cycles: 10 or more.

The resulting reaction product, i.e., the amplified product can be separated by electrophoresis on agarose gel or the like to determine the molecular weight of the amplified product. Thus, the above activity of the present invention of the test strain can be predicted or evaluated by assessing whether or not the molecular weight of the amplified product is enough to cover a nucleic acid molecule corresponding to a region specific to the nucleotide sequence of the present invention. Moreover, the above activity of the present invention can be more accurately predicted or evaluated by analyzing the nucleotide sequence of the amplified product by the method described above or the like. The method for evaluating the above activity of the present invention is as described above.

Alternatively, the evaluation method of the present invention may comprise culturing a test strain and determining the expression level of ACC encoded by a nucleotide sequence of the present invention such as SEQ ID NO: 1, thereby evaluating the test strain for the above activity of the present invention. The expression level of ACC can be determined by culturing the test strain under appropriate conditions and quantifying mRNA of ACC or the protein. Quantification of mRNA or the protein may be accomplished by using known procedures. Quantification of mRNA may be accomplished by, for example, Northern hybridization or quantitative RT-PCR, while quantification of the protein may be accomplished by, for example, Western blotting (Current Protocols in Molecular Biology, John Wiley & Sons 1994-2003).

(2) Selection Methods

Another embodiment of the present invention is a method for selecting a lipid-producing strain using a nucleic acid encoding ACC or an ACC protein of the present invention. The selection method of the present invention may comprise culturing test strains and determining the expression level of ACC encoded by a nucleotide sequence of the present invention such as SEQ ID NO: 1 to select a strain having a desired expression level, whereby a strain having a desired activity can be selected. Alternatively, it may comprise predetermining a type strain, separately culturing the type strain and test strains, determining the above expression level in each strain, and comparing the expression level between the type strain and each test strain, whereby a desired strain can be selected. Specifically, a strain having a desired activity can be selected by culturing a type strain and test strains under appropriate conditions, determining the expression level in each strain, and selecting a test strain showing a higher or lower expression level than that of the type strain, for example. The desired activity may be assessed by determining the expression level of ACC, as described above.

Alternatively, the selection method of the present invention may comprise culturing test strains and selecting a strain showing a higher or lower level of the above activity of the present invention, whereby a strain having a desired activity can be selected. The desired activity may be assessed by determining the expression level of ACC, as described above.

Examples of test strains or type strains that can be used include for example, but are not limited to, a strain transformed with the above vector of the present invention, a strain with suppressed expression of the above nucleic acid of the present invention, a mutagenized strain, a naturally mutated strain, etc. It should be noted that ACC activity of the present invention and/or the activity of complementing yeast ACC deficiency of the present invention can be assayed by the method described in the section "Nucleic acids encoding the acetyl-CoA carboxylase of the present invention", for example. Mutagenesis techniques include, but not limited to, physical methods such as UV or radioactive irradiation, and chemical methods such as chemical treatments with EMS (ethylmethane sulfonate), N-methyl-N-nitrosoguanidine or the like (see, e.g., Yasuji Oshima ed., Biochemistry Experiments vol. 39, Experimental Protocols for Yeast Molecular Genetics, pp. 67-75, Japan Scientific Societies Press).

Strains used as type and test strains of the present invention include, but are not limited to, the lipid-producing fungi or yeast listed above. Specifically, the type and test strains may be a combination of any strains belonging to different genera or species, and one or more test strains may be used simultaneously.

The following examples further illustrate the present invention. However, it should be understood that the present invention is not limited to the examples below.

EXAMPLES

Example 1

(1) Construction of a cDNA Library and EST Analysis

*M. alpina* strain 1S-4 was inoculated into 100 ml of a medium (1.8% glucose, 1% yeast extract, pH 6.0) and incubated with shaking for 4 days at 28° C. The cells were harvested to prepare total RNA using guanidine hydrochloride/CsCl. Using an Oligotex-dT30<Super> mRNA Purification Kit (Takara Bio Inc.) ("dT30" disclosed as SEQ ID NO: 40), poly(A)+RNA was purified from the total RNA. This was used to construct a cDNA library using a ZAP-cDNA GigapackIII Gold Cloning Kit (STRATAGENE). One-pass sequence analysis was performed from the 5'-end of cDNA (about 2000 clones).

(2) Search for ACC Homologs

The sequences obtained by the above EST analysis were searched against amino acid sequences deposited in GENEBANK using the homology search program BLASTX, to extract homologs of acetyl-CoA carboxylase. As a result, a sequence having the highest identity to an acetyl-CoA carboxylase homolog from *Schizosaccharomyces pombe* (accession number P78820), i.e., a sequence corresponding to nucleotides 5833-6026 of SEQ ID NO: 1, was found.

Example 2

(1) Cloning of MaACC

The cDNA library was screened for the sequence corresponding to nucleotides 5833-6026 of SEQ ID NO: 1 found in Example 1, because this sequence seemed to encode a fragment of an acetyl-CoA carboxylase homolog of *M. alpina* (MaACC). To prepare a probe by PCR, primers 931-F and 931-R were first designed.

```
                                    (SEQ ID NO: 6)
931-F: 5'-GCCAACTGGCGTGGATTCTC-3'

(SEQ ID NO: 7)
931-R: 5'-GTCCTCGTTGATAGTAGGGTC-3'
```

PCR was performed using the cDNA library (2.6×10$^6$ pfu/µl) as a template along with ExTaq (Takara Bio Inc.) and primers 931-F and 931-R. PCR conditions included 94° C. for 2 min followed by 30 cycles of 94° C. for 1 min, 55° C. for 1 min and 72° C. for 3 min.

The amplified fragments were TA-cloned using a TOPO-TA cloning Kit (INVITROGEN CORPORATION). The nucleotide sequences of some clones were determined, and a clone containing nucleotides 5835-6014 of SEQ ID NO: 4 was designated as pCR-MaACC-P1. Then, PCR was performed using this plasmid as a template along with the above primers. ExTaq (Takara Bio Inc.) was used for the reaction, but the amplified DNA was labeled with digoxigenin (DIG) by using a PCR labeling mix (Roche Diagnostics) instead of the dNTP mix included in the kit, thereby generating a probe for screening the cDNA library. This probe was used to screen the cDNA library. Hybridization conditions are as follows.

Buffer: 5×SSC, 1% SDS, 50 mM Tris-HCl (pH 7.5), 50% formamide;
Temperature: 42° C. (overnight);
Washing conditions: 3 times in a solution of 0.2×SSC, 0.1% SDS (65° C.) for 20 minutes. Detection was accomplished by using a DIG nucleic acid detection kit (Roche Diagnostics). Plasmids were excised by in vivo excision from phage clones obtained by screening. The nucleotide sequence of the plasmid pBMaACC-p38 containing a segment corresponding to nucleotides 5833-6026 of SEQ ID NO: 1 and having the longest insert among these plasmids was determined. The plasmid pBMaACC-P38 contained nucleotides 1892-6865 of SEQ ID NO: 4. This clone seemed not to contain total MaACC in view of a comparison to known acetyl-CoA carboxylase homologs, the presence or absence of a start codon, etc.

In order to obtain total MaACC, three rounds of 5'-RACE were performed using a 5'-Full RACE Core Set (Takara Bio Inc.) following the manufacturer's protocol, as follows. Total RNA was the same as used for the cDNA library construction. To perform 5'-RACE (first round), the following primers were designed on the basis of the nucleotide sequence of the insert of pBMaACC-P38:

```
                                    (SEQ ID NO: 8)
ACC-RT-1 primer: pTGGTGCCGGGTTGCT (SEQ ID NO: 9)
ACC-S1-1 primer: GCAAACTTGTTCGCTACCTTG (SEQ ID NO: 10)
ACC-A1-1 primer: TCGTTCTCCTTCTCCAACAA (SEQ ID NO: 11)
ACC-S2-1 primer: CAGGCCTATGCTGAGATTGAG (SEQ ID NO: 12)
ACC-A2-1 primer: TGGACCTCTTCCAACGAGTAA.
```

In the 5'-RACE (first round), DNA fragments amplified with the ACC-S2-1 primer and ACC-A2-1 primer were TA-cloned, and the longest clone containing a partial sequence of MaACC among the resulting clones was designated as pCR-MaACC-P2-5. This clone contained nucleotides 1183-2011 of SEQ ID NO: 4.

To further perform 5'-RACE (second round), the following primers were designed on the basis of this sequence:

```
5'-RACE (second round)
                                    (SEQ ID NO: 13)
ACC-RT-2 primer: pCAGGGCGTTCAGCAGTG (SEQ ID NO: 14)
ACC-S1-2 primer: CGAGTACTTGATCCGCCTTT (SEQ ID NO: 15)
ACC-A1-2 primer: GGAAATCACCACGAATGGAG
```

-continued

```
                                    (SEQ ID NO: 16)
ACC-S2-2 primer: GGAGTTCGAGGAAAACACCA (SEQ ID NO: 17)
ACC-A2-2 primer: TGACCACGATCCTGTCCATA.
```

In the 5'-RACE (second round), DNA fragments amplified with the ACC-S2-2 primer and ACC-A2-2 primer were TA-cloned, and the longest clone containing a partial sequence of MaACC among the resulting clones was designated as pCR-MaACC-P7-15. This clone contained nucleotides 738-1522 of SEQ ID NO: 4.

To further perform 5'-RACE (third round), the following primers were designed on the basis of this sequence:

```
5'-RACE (third round)
                                    (SEQ ID NO: 18)
ACC-RT-3 primer: pTCGGGCTTGGCAATG (SEQ ID NO: 19)
ACC-S1-3 primer: ATCTGGAGGTCCAGCTTTTG (SEQ ID NO: 20)
ACC-A1-3 primer: GCGTTACCAGCCAACTTCAT (SEQ ID NO: 21)
ACC-S2-3 primer: GCGTCGCCATCAGAAGATTA (SEQ ID NO: 22)
ACC-A2-3 primer: AGGCCTGAGCGAACTTTTCT.
```

In the 5'-RACE (third round), DNA fragments amplified with the ACC-S2-3 primer and ACC-A2-3 primer were TA-cloned, and the longest clone containing a fragment of MaACC among the resulting clones was designated as pCRMaACC-P9-2. This clone contained nucleotides 1-792 of SEQ ID NO: 4, and seemed to contain a start codon of MaACC in view of a comparison with known acetyl-CoA carboxylase homologs or the like. The sequences obtained in this manner were ligated to give the sequence of SEQ ID NO: 4 representing a cDNA sequence containing the complete CDS of MaACC.

Then, a plasmid containing SEQ ID NO: 4 was constructed as follows. First, a DNA fragment of about 8 kbp obtained by digesting plasmid pBMaACC-P38 with restriction endonucleases NotI and BamHI and a DNA fragment of about 0.8 kbp obtained by digesting plasmid pCRMaACC-P2-5 with restriction endonucleases NotI (MCS of vector pCR2.1, located 5'-upstream of MaACC) and BamHI were ligated to generate plasmid pBMaACC-P4. On the other hand, cDNA was synthesized by a SuperScript First-Strand system for RT-PCR (Invitrogen) using the same total RNA as used for the cDNA library construction along with random primers.

This was used as a template to further perform PCR using ExTaq (Takara Bio) with primer ACC-NotI: GCGGCGGC-CGCTCCCACTGACTCAAGCGG (SEQ ID NO: 23) and the ACC-A1-2 primer, and the resulting DNA fragments were TA-cloned A DNA fragment of about 1.5 kb obtained by digesting a clone containing a correct segment of nucleotides 1-1578 of SEQ ID NO: 4 with restriction endonucleases NotI and XbaI and a DNA fragment of about 8.4 kb obtained by digesting plasmid pBMaACC-P4 with restriction endonucleases NotI and XbaI were ligated to generate plasmid pB-MaACC.

(2) Sequence Analysis

The cDNA sequence (SEQ ID NO: 4) of ACC from *M. alpina* (MaACC) obtained as above was subjected to ORF analysis. As a result, it was predicted that the CDS region of ACC of the present invention corresponds to nucleotides 45-6734 of SEQ ID NO: 4 (SEQ ID NO: 3) and the ORF region corresponds to nucleotides 45-6731 of SEQ ID NO: 4 (SEQ ID NO: 1). The cDNA sequence (SEQ ID NO: 4) of ACC from *M. alpina* (hereinafter also referred to as "MaACC") and its putative amino acid sequence (SEQ ID NO: 2) are shown in FIG. 1.

Furthermore, SEQ ID NO: 4 was subjected to homology analysis using BLASTX against amino acid sequences registered in GenBank. As a result, MaACC showed homology to ACC homologs of eukaryotic microorganisms, especially the highest identity to the putative protein RO3G_04977 from *Rhizopus oryzae* among known amino acid sequences. The nucleotide sequence identity between the CDS of this protein and the CDS of MaACC and the identity between its amino acid sequence and the putative amino acid sequence of MaACC protein were determined by clustalW to be 65.5% and 66.3%, respectively. The identities to the putative amino acid sequences of ACC homologs from other fungi were 58.8% to a homolog from *Neurospora crassa* (accession number EAA33781), 58.3% to a homolog from *Aspergillus fumigatus* (accession number EAL93163), and 55.1% to the cytoplasmic ACC Acc1p and 44.7% to the mitochondrial ACC Hfa1p of yeast *S. cerevisiae*.

On the other hand, a fragment of an ACC homolog from *M. alpina* strain CBS528.72 has been previously registered in Genbank (nucleic acid sequence: accession number AJ586915 (non-patent document 6) (SEQ ID NO: 24); amino acid sequence: accession number CAE52914 (SEQ ID NO: 25)). The newly obtained full-length cDNA sequence from *M. alpina* 1S-4 and its putative amino acid sequence were compared with these sequences. The comparison of the nucleic acid sequences was shown in FIG. 2, and the comparison of the amino acid sequences was shown in FIG. 3. The CDS region of the nucleotide sequence of the accession number AJ586915 corresponds to nucleotides 342-1439 of SEQ ID NO: 4 and showed 91.3% identity so far as this region is concerned. The amino acid sequence of accession number CAE52914 corresponds to amino acids 100-465 of SEQ ID NO: 2 and showed 97.8% identity so far as this region is concerned.

Example 3

Construction of an Expression Vector

The yeast expression vector pYE22m was digested with restriction endonuclease EcoRI and blunt-ended using a Blunting Kit (Takara Bio). Into this was inserted a NotI linker (p-GCGGCCGC: SEQ ID NO: 26) to construct vector pYE22mN. A fragment obtained by digesting vector pYE22mN with restriction endonucleases NotI and SalI and a fragment of about 6.9 kb obtained by digesting plasmid pB-MaACC with restriction endonucleases NotI and XhoI were ligated using Ligation high (TOYOBO) to generate plasmid pYE-MaACC. Then, the plasmid pYE-MaACC was digested with restriction endonuclease HindIII and blunt-ended using a Blunting Kit (Takara Bio), and inserted into the SmaI site of plasmid pUC-URA3 to construct plasmid pUC-URA3-MaACC. This plasmid is digested with restriction endonuclease HindIII and transformed into the yeast strain Δura3 so that an expression cassette of ACC from *M. alpina* is inserted downstream of URA3 on a yeast chromosome.

Example 4

Acquisition of Yeast Strains Transformed with a Cassette for Expressing ACC from M. Alpina Strain 1S-4 and Random Spore Analysis The yeast knockout strain YSC1021-673427 (Δacc1: KanMX/ACC1, his3Δ1/his3Δ1, leu2Δ0/leu2Δ0, ura3Δ0/ura3Δ0, LYS2/lys2Δ0, MET15/met15Δ0, open biosystems), which is a heterozygous diploid lacking the yeast cytoplasmic ACC gene, was transformed with a DNA fragment obtained by digesting pUC-URA3-MaACC constructed in Example 3 with restriction endonuclease HindIII. Transformed strains were selected on the basis of growth on SD-Ura agar plates. Strains randomly selected in this manner were designated as MaACC-HD-#1 strain and MaACC-HD-#2 strain (Δacc1: KanMX/ACC1, his3Δ1/his3Δ1, leu2Δ0/leu2Δ0, MaACC-URA3/ura3Δ0, LYS2/lys2Δ0, MET15/met15Δ0).

To induce sporulation in the MaACC-HD-#1 strain and MaACC-HD-#2 strain, these strains were spread on YPD agar plates and incubated at 30° C. for 2 days. Grown cells were spread on sporulation agar plates (1% potassium acetate, 0.1% yeast extract, 0.05% glucose, 2% agar) and incubated at 25° C. for 4 days. One loopful of the cell culture was suspended in 1 ml of a Zymolyase solution (1.2 M sorbitol, 50 mM potassium phosphate buffer (pH 7.5), 14 mM 2-mercaptoethanol, 0.2 mg/ml Zymolyase 100T (Seikagaku Corporation)) and incubated with shaking at 30° C. for 24 hours. Then, the cells were harvested by centrifugation and the supernatant was removed. The cells were vigorously stirred with 1 ml of sterilized water and then collected by centrifugation and the supernatant was removed. This operation was repeated further twice.

The resulting cells were suitably diluted with sterilized water, and spread on YPD agar plates to form single colonies. One hundred random strains of the resulting colonies (in a total of 200 strains) were replicated on YPD, YPD+G418 (200 mg/L), SD-Ura, SD-Met and SD-Lys agar plates and assessed for growth on each plate. The results are shown in Table 1.

TABLE 1

Growth of transformed strains of a heterozygous diploid lacking the yeast cytoplasmic ACC gene

| | | YPD | YPD + G418 | SD – Ura | SD – Met | SD – Lys | number | |
|---|---|---|---|---|---|---|---|---|
| I | a | ○ | ○ | ○ | ○ | ○ | 30* | 74 |
| | b | ○ | ○ | ○ | ○ | X | 12 | |
| | c | ○ | ○ | ○ | X | ○ | 11 | |
| | d | ○ | ○ | ○ | X | X | 21 | |
| II | a | ○ | X | X | ○ | ○ | 12 | 61 |
| | b | ○ | X | X | ○ | X | 16 | |
| | c | ○ | X | X | X | ○ | 9 | |
| | d | ○ | X | X | X | X | 24 | |
| III | a | ○ | X | ○ | ○ | ○ | 17 | 65 |
| | b | ○ | X | ○ | ○ | X | 20 | |
| | c | ○ | X | ○ | X | ○ | 20 | |
| | d | ○ | X | ○ | X | X | 8 | |
| IV | a | ○ | ○ | X | ○ | ○ | 0 | 0 |
| | b | ○ | ○ | X | ○ | X | 0 | |
| | c | ○ | ○ | X | X | ○ | 0 | |
| | d | ○ | ○ | X | X | X | 0 | |

The ACC1 gene from S. cerevisiae and MaACC may be segregated into four genotypes:
(1) Δacc1: KanMX, MaACC-URA3;
(2) ACC1, ura3Δ0;
(3) ACC1, MaACC-URA3; and
(4) Δacc1: KanMX, ura3Δ0.

The phenotypes of strains having these genotypes correspond to the numbers (I-IV) shown in the first column in Table 1, but some strains growing on all of the test agar plates are diploid.

From eight of these strains, genomic DNA was isolated using Dr. GenTLE (for yeast) (Takara Bio) and subjected to PCR using ExTaq (Takara Bio) with a combination of primers ScACC1-19/ScACC1+658, primers ScACC1-19/KanB and primers ACC1-scf5/ACC1-scr5. As a result, three of the eight strains showed amplification of DNA to a suitable size with the combination of primers, indicating that they are diploid. The sequences of the above primers are shown below:

```
                            (SEQ ID NO: 27)
ScACC1-19:    CCCGAAACAGCGCAGAAAATTAG (SEQ ID NO: 28)
ScACC1+658:   CCAGACCGGTTTTCTCGTCCACGTG (SEQ ID NO: 29)
KanB:         CTGCAGCGAGGAGCCGTAAT (SEQ ID NO: 30)
ACC1-scf5:    CGCATTGGTCTTGCTAGTGA (SEQ ID NO: 31)
ACC1-scr5:    AAGTGCGACACTCCGTTCTT.
```

Thus, the 74 strains of phenotype I in Table 1 include about 60 haploid strains, showing that strains of the above genotypes (1):(2):(3):(4) appear in a segregation ratio of about 1:1:1:0.

It should be noted here that Δacc1 strains are known to be lethal in S. cerevisiae. No strain of genotype (4) was obtained because they are Δacc1 and lethal. However, strains of genotype (1) are obtained though they are Δacc1, showing that MaACC could complement Δacc1. In other words, MaACC was shown to have ACC activity functioning in the cytoplasm.

Example 5

Southern Analysis

Two strains were randomly selected from each of groups I-a (strains shown to be haploid by PCR), II-a and III-a in Table 1 obtained in Example 4. Genomic DNA was isolated in the same manner as above. This was digested with restriction endonuclease BamHI or HindIII and electrophoresed on 0.8% agarose gel, and DNA was transferred and fixed to Hybond N+. Probes used were (1) a DNA fragment from –500 to –157 upstream of the S. cerevisiae ACC1 gene, (2) a DNA fragment from 101 to 658 within the S. cerevisiae ACC1 gene, and (3) a DNA fragment of MaACC (SEQ ID NO: 4). AlkPhos Direct (GE Healthcare) was used for labeling and detecting the probes. Southern analysis was performed using probe (1) or probe (2) for DNA digested with restriction endonuclease BamHI and probe (3) for DNA digested with restriction endonuclease HindIII. As a result, in I-a, a strain shown to be haploid by PCR, probe (1) detected a 3.2 kb signal, probe (2) detected no signal, and probe (3) detected a 8.2 kb signal. On the other hand, probe (1) and probe (2) detected a 7.6 kb signal and probe (3) detected no signal in II-a, while probe (1) and probe (2) detected a 7.6 kb signal and probe (3) detected a 8.2 kb signal in III-a.

These results showed that these strains contain the following cytoplasmic ACC genes; I-a contains MaACC from M. alpina strain 1S-4 alone, II-a contains ACC1 from S. cerevisiae alone, and III-a contains both MaACC and ACC1.

Example 6

Analysis of MaACC-Expressing Yeast

One loopful each of four random strains from each of groups I-a (strains shown to be haploid by PCR), II-a and III-a in Table 1 obtained in Example 4 was inoculated into 10 ml of YPD5+Ura (2% yeast extract, 1% polypeptone, 5% glucose, 0.002% uracil) liquid medium and incubated with shaking at 30° C. for 24 hours or 72 hours. At the end of the incubation, the absorbance of the cultures at 600 nm was measured to assess cell growth (Table 2).

TABLE 2

| | Cell growth -OD600 nm | | |
|---|---|---|---|
| | I-a | II-a | III-a |
| 24 hr | 7.08 ± 0.72 | 6.12 ± 0.35 | 7.4 ± 0.54 |
| 72 hr | 8.97 ± 2.26 | 7.55 ± 1.21 | 9.88 ± 2.4 | mean ± SD

Cells were harvested by centrifugation and lyophilized and then fatty acids in the cells were converted into methyl esters using methanolic HCl, then extracted with hexane, and hexane was distilled off and the residue was analyzed by gas chromatography to determine fatty acid compositions at the different incubation periods (Tables 3 and 4).

TABLE 3

| | Compositional ratio of fatty acids of yeast strains (after incubation of 24 hours) | | |
|---|---|---|---|
| | I-a | II-a | III-a |
| 16:0 | 13.22 ± 0.59 | 21.83 ± 0.49 | 20.54 ± 0.65 |
| 16:1 | 50.06 ± 1.12 | 39.62 ± 0.50 | 42.62 ± 1.09 |
| 18:0 | 1.98 ± 0.17 | 5.87 ± 0.51 | 4.91 ± 0.50 |
| 18:1 | 23.24 ± 0.81 | 26.21 ± 1.31 | 24.60 ± 1.68 |
| 22:0 | 1.48 ± 0.33 | 0.23 ± 0.08 | 0.83 ± 0.18 |
| 26:0 | 0.00 ± 0.00 | 1.16 ± 0.09 | 0.93 ± 0.11 |
| other | 10.02 ± 0.35 | 5.08 ± 0.91 | 5.58 ± 0.55 | mean ± SD

TABLE 4

| | Compositional ratio of fatty acids of yeast strains (after incubation of 72 hours) | | |
|---|---|---|---|
| | I-a | II-a | III-a |
| 16:0 | 8.10 ± 1.73 | 16.55 ± 3.69 | 13.15 ± 3.91 |
| 16:1 | 50.52 ± 0.54 | 40.51 ± 0.16 | 42.61 ± 1.73 |
| 18:0 | 1.79 ± 0.20 | 6.31 ± 0.84 | 6.23 ± 0.32 |
| 18:1 | 22.43 ± 4.27 | 29.23 ± 1.76 | 31.28 ± 5.75 |
| 22:0 | 1.12 ± 0.38 | 0.50 ± 0.42 | 0.98 ± 0.51 |
| 26:0 | 0.48 ± 0.13 | 1.76 ± 0.18 | 1.30 ± 0.58 |
| other | 15.55 ± 6.16 | 5.14 ± 0.54 | 4.45 ± 1.13 | mean ± SD

As a result, I-a containing MaACC from *M. alpina* alone showed better growth than II-a containing the ACC gene from *S. cerevisiae* alone. III-a containing both ACC genes showed further better growth than I-a.

Moreover, the strains of different genotypes showed different compositional ratio of fatty acids, i.e., I-a containing MaACC from *M. alpina* alone showed a marked decrease in the proportions of palmitic acid, stearic acid and hexadocosanoic acid among saturated fatty acids as well as a decreased proportion of oleic acid among monounsaturated fatty acids, as compared with II-a containing ACC from *S. cerevisiae* alone. On the other hand, it showed an increase in the proportion of tetradocosanoic acid among saturated fatty acids and the proportion of palmitoleic acid among monosaturated fatty acids. III-a containing both MaACC from *M. alpina* and ACC1 from *S. cerevisiae* showed an intermediate compositional ratio of fatty acids between I-a and II-a.

Example 7

Acquisition of the Genomic Sequence of the ACC Gene

*M. alpina* strain 1S-4 was inoculated into 100 ml of liquid medium (1% glucose, 0.5% yeast extract, pH 6.0) and incubated with shaking at 28° C. for 4 days. The cells were harvested by filtration and genomic DNA was isolated using DNeasy Plant (Quiagen).

To determine the genomic DNA sequence of ACC of *M. alpina* strain 1S-4, the following primers were designed:

```
                                          (SEQ ID NO: 32)
ACC-G1: atgactaccaacgtacagtccttcattg (SEQ ID NO: 33)
ACC-G2: ttaaacggtcatcgtggcgaacttggc.
```

The genomic DNA of *M. alpina* strain 1S-4 was used as a template to perform 30 cycles of PCR at 98° C. for 10 sec and 68° C. for 15 min using LATaq (Takara Bio). The resulting DNA fragments of about 8 kb were TA-cloned. The genomic DNA sequence (SEQ ID NO: 5) of ACC of *M. alpina* strain 1S-4 was determined by nucleotide sequencing of inserts of multiple clones.

The genomic DNA sequence of the ACC gene of *M. alpina* strain 1S-4 was compared with the cDNA sequence to reveal that it contained five introns and exon regions corresponding to nucleotides 1-27, 315-665, 1271-2828, 2917-3463, 3590-6239, and 6339-7889 of SEQ ID NO: 5.

Example 8

Increased Expression of ACC in *Mortierella* Alpina (1) Construction of an Expression Vector PCR was performed using plasmid pB-MaACC (see Example 2) as a template along with the following primers ACCExF-SpeI and ACCExR-SpeI to give a PCR product of about 6.7 kbp.

```
primer ACCExF-SpeI:
                                          (SEQ ID NO: 36)
5'-ATACTAGTATGACTACCAACGTACAGTCC-3' primer ACCExR-SpeI:
                                          (SEQ ID NO: 37)
5'-GGACTAGTCTTAAACGGTCATCGTGGCG-3'.
```

This was digested with restriction endonuclease SpeI and ligated to a fragment obtained by digesting plasmid pSDY with restriction endonuclease SpeI to generate plasmid pSDY-ACC (FIG. 5).

(2) Transformation of *Mortierella alpina*

An uracil-auxotrophic strain Aura-3, which was derived from *M. alpina* by a method according to International Publication No. WO2005/019437 (entitled "Method of Breeding Lipid-Producing Fungus"), was used as a host and transformed by the particle delivery method. SC agar medium (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, and 2% agar) was used for selecting transformed strains.

(3) Selection of Transformed Strains

About 50 transformed strains were isolated and inoculated into 15 ml of GY (2% glucose, 1% yeast extract pH 6.0) liquid medium and incubated with shaking at 28° C. for 8 days. The cells were harvested and dried by maintaining at 120° C. for 2 hours, and fatty acids in the cells were converted into methyl esters using methanolic HCl and subjected to fatty acid analysis. Four strains showing high-level production of fatty acids and a high proportion of arachidonic acid, A4, H9, H11 and H20 were selected for the subsequent experiments.

(4) Verification of Transformation of the MaACC Expression Cassette

The four transformed strains selected as above were incubated in GY liquid medium and genomic DNA was isolated. To assess whether or not the expression cassette of MaACC has been transformed into the transformed strains, PCR was performed using the genomic DNA as a template along with the primers ACC-F7 and trpCt-R set forth below. When pSDY-ACC is used as a template in this reaction, a PCR product of about 1.6 kbp is amplified. In each transformed strain, a PCR product of this size was found, indicating that the MaACC expression cassette has been transformed into these strains. However, no PCR product could be detected in the host Aura-3 strain under the same conditions.

```
                                     (SEQ ID NO: 38)
ACC-F7:   5'-GCTTGGTCGCGATGTCTACACCTCG-3'

(SEQ ID NO: 39)
trpCt-R:  5'-ACGTATCTTATCGAGATCCTGAACACCA-3'
```

(5) Evaluation of Transformed Strains

Figure 6:
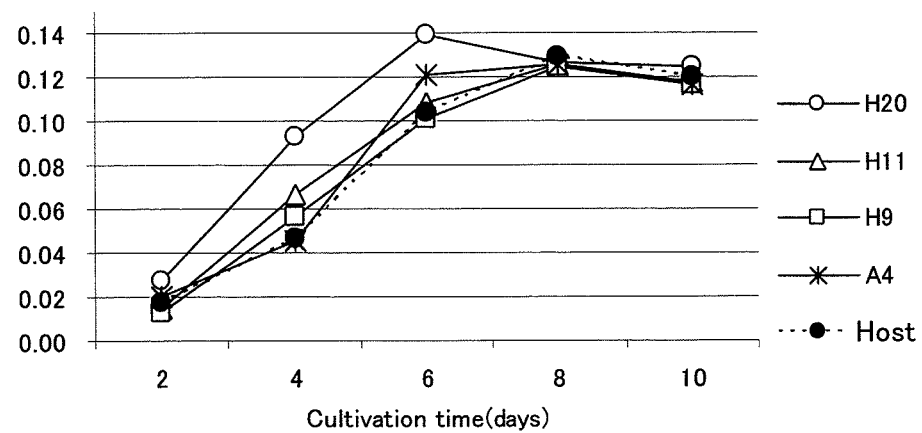
FIG. 6 is a graph showing changes over time in the dry cell weight of transformed strains of *M. alpina*. Ordinate: dry cell weight (g/tube); abscissa: incubation period (days).
Figure 7:
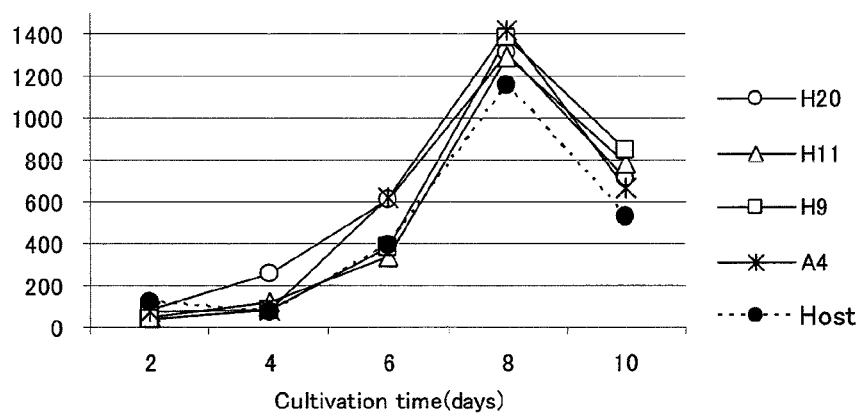
FIG. 7 is a graph showing changes over time in the amount of fatty acids produced by transformed strains of *M. alpina*. Ordinate: the amount of fatty acids produced (mg/L medium); abscissa: incubation period (days).

The four transformed strains were evaluated for changes in growth and fatty acid production over time. That is, each strain was inoculated into 15 ml of GY liquid medium and incubated with shaking at 28° C. On days 2, 4, 6, 8, and 10, all cells were harvested and assessed for dry cell weight and fatty acid production level (FIGS. 6 and 7). As a result, the transformed strains and host Aura-3 strain all showed the highest level of fatty acids production on day 8.

Figure 8:
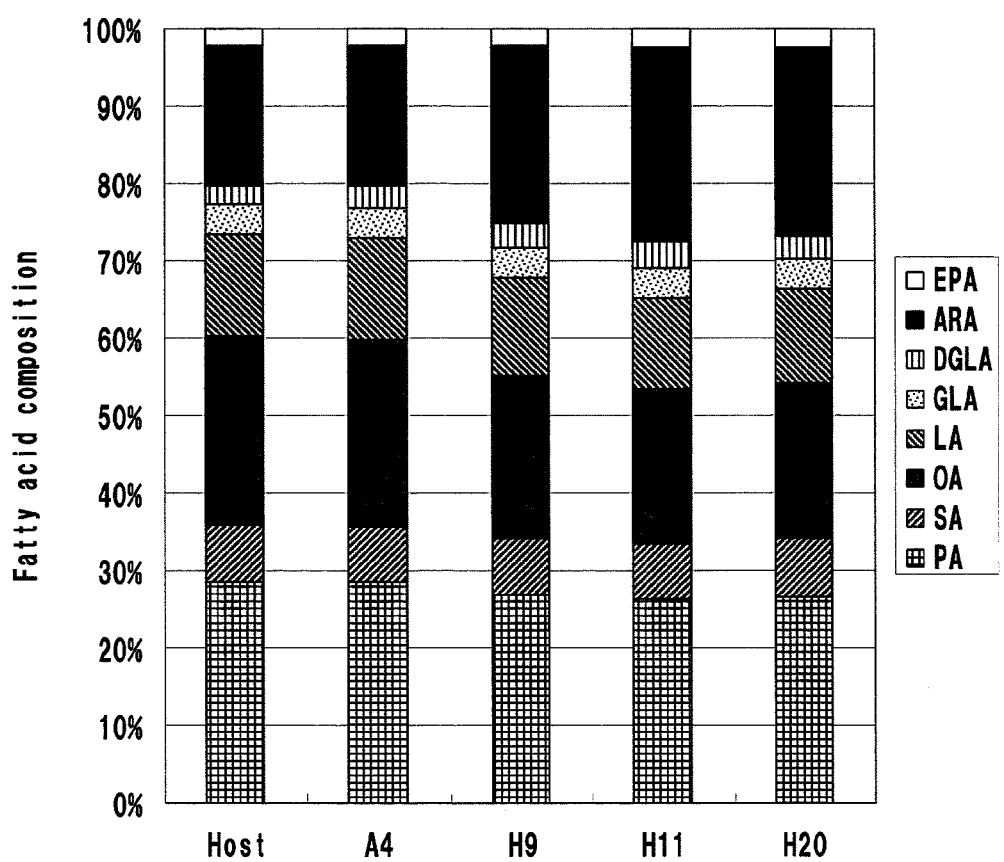
FIG. 8 is a graph showing compositional ratio of fatty acids of transformed strains of *M. alpina* on day 8 of incubation. Ordinate: compositional ratio of fatty acids; abscissa: host cell and transformed strains. The legend for the graph is as follows: EPA: eicosapentaenoic acid; ARA: arachidonic acid; DGLA: dihomo-γ-linolenic acid; GLA:γ-linolenic acid; LA: linolic acid; OA: oleic acid; SA: stearic acid; PA: palmitic acid.

Thus, the fatty acid compositions, dry cell weights, total fatty acids and arachidonic acid production levels on day 8 were compared (FIG. 8, Table 5). As a result, the host Δura-3 strain and transformed strains showed a nearly equal dry cell weight, but the amount of fatty acids produced per medium increased 1.1-1.2-fold and the amount of arachidonic acid produced per medium increased 1.2-1.6-fold.

The values in the parentheses represent the ratios to the host.

In this manner, increased expression of ACC in *Mortierella alpine* improved fatty acid production level, especially improved arachidonic acid production level among fatty acids.

SEQUENCE LISTING FREE TEXT

SEQ ID NO: 6: primer
SEQ ID NO: 7: primer
SEQ ID NO: 8: primer
SEQ ID NO: 9: primer
SEQ ID NO: 10: primer
SEQ ID NO: 11: primer
SEQ ID NO: 12: primer
SEQ ID NO: 13: primer
SEQ ID NO: 14: primer
SEQ ID NO: 15: primer
SEQ ID NO: 16: primer
SEQ ID NO: 17: primer
SEQ ID NO: 18: primer
SEQ ID NO: 19: primer
SEQ ID NO: 20: primer
SEQ ID NO: 21: primer
SEQ ID NO: 22: primer
SEQ ID NO: 23: primer
SEQ ID NO: 26: primer
SEQ ID NO: 27: primer
SEQ ID NO: 28: primer
SEQ ID NO: 29: primer
SEQ ID NO: 30: primer
SEQ ID NO: 31: primer
SEQ ID NO: 32: primer
SEQ ID NO: 33: primer
SEQ ID NO: 36: primer
SEQ ID NO: 37: primer
SEQ ID NO: 38: primer
SEQ ID NO: 39: primer

TABLE 5

Comparison of growth and productivity of fatty acids and arachidonic acid

| | Host | A4 | H9 | H11 | H20 |
|---|---|---|---|---|---|
| Dry cell weight (g) | 0.129 (1.0) | 0.125 (1.0) | 0.125 (1.0) | 0.125 (1.0) | 0.126 (1.0) |
| Total fatty acids per medium (mg/L broth) | 134.5 (1.0) | 170.1 (1.3) | 166.5 (1.2) | 154.8 (1.2) | 155.3 (1.2) |
| Total fatty acids per cell (mg/g dry cell) | 1156.5 (1.0) | 1420.9 (1.2) | 1383.7 (1.2) | 1293.7 (1.1) | 1308.1 (1.1) |
| Arachidonic acid per medium (mg/L broth) | 24.2 (1.0) | 30.9 (1.3) | 37.9 (1.6) | 38.9 (1.6) | 38.0 (1.6) |
| Arachidonic acid per cell (mg/g dry cell) | 208.4 (1.0) | 258.6 (1.2) | 315.2 (1.5) | 325.2 (1.6) | 319.9 (1.5) |

The invention claimed is:

1. A cDNA comprising any one of (a)-(c) below:
   (a) a nucleotide sequence encoding a protein consisting of an amino acid sequence with deletion, substitution or addition of 1-200 amino acids in the amino acid sequence of SEQ ID NO: 2;
   (b) a nucleotide sequence sharing an identity of 90% or more with the nucleotide sequence consisting of SEQ ID NO: 1; or
   (c) a nucleotide sequence encoding a protein consisting of an amino acid sequence sharing an identity of 90% or more with the amino acid sequence consisting of SEQ ID NO: 2.

2. The cDNA of claim 1, which comprises any one of (a)-(c) below:
   (a) a nucleotide sequence encoding a protein consisting of an amino acid sequence with deletion, substitution or addition of 1-100 amino acids in the amino acid sequence of SEQ ID NO: 2;
   (b) a nucleotide sequence sharing an identity of 95% or more with the nucleotide sequence consisting of SEQ ID NO: 1; or
   (c) a nucleotide sequence encoding a protein consisting of an amino acid sequence sharing an identity of 95% or more with the amino acid sequence consisting of SEQ ID NO: 2.

3. A cDNA comprising any one of (a)-(c) below:
   (a) the nucleotide sequence of SEQ ID NO: 1;
   (b) a nucleotide sequence encoding a protein consisting of the amino acid sequence of SEQ ID NO: 2; or
   (c) the nucleotide sequence of SEQ ID NO: 4.

4. A recombinant vector comprising the cDNA of claim 1.

5. An isolated cell transformed with the recombinant vector of claim 4.

6. A method for preparing a fatty acid composition obtained by culturing the transformed cell of claim 5, comprising collecting the fatty acid composition from cultures of the transformed cell of claim 5.

* * * * *

SEQUENCE LISTING

<160> NUMBER OF SEQ ID NOS: 40

<210> SEQ ID NO 1
<211> LENGTH: 6684
<212> TYPE: DNA
<213> ORGANISM: Mortierella alpina
<220> FEATURE:
<221> NAME/KEY: CDS
<222> LOCATION: (1)..(6684)

<400> SEQUENCE: 1

| | | | | | | | | | | | | | | | | |
|---|---|---|---|---|---|---|---|---|---|---|---|---|---|---|---|---|
| atg | act | acc | aac | gta | cag | tcc | ttc | att | gga | gga | aac | gca | tta | gag | aac | 48 |
| Met | Thr | Thr | Asn | Val | Gln | Ser | Phe | Ile | Gly | Gly | Asn | Ala | Leu | Glu | Asn | |
| 1 | | | | 5 | | | | | 10 | | | | | 15 | | |

| gcc | cct | gct | gga | gct | gtc | cgc | gag | ttt | gtt | aac | cag | cat | gga | ggc | cac | 96 |
|---|---|---|---|---|---|---|---|---|---|---|---|---|---|---|---|---|
| Ala | Pro | Ala | Gly | Ala | Val | Arg | Glu | Phe | Val | Asn | Gln | His | Gly | Gly | His | |
| | | | 20 | | | | | 25 | | | | | 30 | | | |

| agc | gtg | atc | acc | aag | atc | ctg | atc | gcc | aac | aac | ggt | att | gcg | gcc | gtc | 144 |
|---|---|---|---|---|---|---|---|---|---|---|---|---|---|---|---|---|
| Ser | Val | Ile | Thr | Lys | Ile | Leu | Ile | Ala | Asn | Asn | Gly | Ile | Ala | Ala | Val | |
| | | 35 | | | | | 40 | | | | | 45 | | | | |

| aag | gag | atc | cga | tct | gtc | cgc | aag | tgg | gcg | tac | gag | acc | ttt | gga | gat | 192 |
|---|---|---|---|---|---|---|---|---|---|---|---|---|---|---|---|---|
| Lys | Glu | Ile | Arg | Ser | Val | Arg | Lys | Trp | Ala | Tyr | Glu | Thr | Phe | Gly | Asp | |
| 50 | | | | | 55 | | | | | 60 | | | | | | |

| gag | cgt | gcg | atc | cag | ttc | acg | gtc | atg | gct | acg | cca | gag | gat | ctg | aag | 240 |
|---|---|---|---|---|---|---|---|---|---|---|---|---|---|---|---|---|
| Glu | Arg | Ala | Ile | Gln | Phe | Thr | Val | Met | Ala | Thr | Pro | Glu | Asp | Leu | Lys | |
| 65 | | | | | 70 | | | | | 75 | | | | | 80 | |

| atc | aat | gct | gaa | tat | atc | cgc | atg | gcc | gac | cag | tat | gtc | gaa | gta | ccg | 288 |
|---|---|---|---|---|---|---|---|---|---|---|---|---|---|---|---|---|
| Ile | Asn | Ala | Glu | Tyr | Ile | Arg | Met | Ala | Asp | Gln | Tyr | Val | Glu | Val | Pro | |
| | | | | 85 | | | | | 90 | | | | | 95 | | |

| gga | gga | tcc | aac | aac | aac | aac | tac | gcc | aac | gtt | gac | ctc | att | gtc | gac | 336 |
|---|---|---|---|---|---|---|---|---|---|---|---|---|---|---|---|---|
| Gly | Gly | Ser | Asn | Asn | Asn | Asn | Tyr | Ala | Asn | Val | Asp | Leu | Ile | Val | Asp | |
| | | | 100 | | | | | 105 | | | | | 110 | | | |

| att | gcc | gaa | cgc | acc | ggc | gtc | cat | gct | gtg | tgg | gct | gga | tgg | gga | cat | 384 |
|---|---|---|---|---|---|---|---|---|---|---|---|---|---|---|---|---|
| Ile | Ala | Glu | Arg | Thr | Gly | Val | His | Ala | Val | Trp | Ala | Gly | Trp | Gly | His | |
| | | 115 | | | | | 120 | | | | | 125 | | | | |

| gcc | tcg | gag | aac | ccc | aaa | ctc | cca | gag | tct | ctt | cgc | gac | agc | cct | caa | 432 |
|---|---|---|---|---|---|---|---|---|---|---|---|---|---|---|---|---|
| Ala | Ser | Glu | Asn | Pro | Lys | Leu | Pro | Glu | Ser | Leu | Arg | Asp | Ser | Pro | Gln | |
| 130 | | | | | 135 | | | | | 140 | | | | | | |

| aag | atc | atc | ttc | atc | gga | ccc | ccc | ggc | tcc | gcc | atg | cgc | tcg | ttg | ggt | 480 |
|---|---|---|---|---|---|---|---|---|---|---|---|---|---|---|---|---|
| Lys | Ile | Ile | Phe | Ile | Gly | Pro | Pro | Gly | Ser | Ala | Met | Arg | Ser | Leu | Gly | |
| 145 | | | | | 150 | | | | | 155 | | | | | 160 | |

| gac | aag | atc | tcg | tcc | acg | atc | gtc | gct | caa | tcg | gcc | gac | gtc | cct | acg | 528 |
|---|---|---|---|---|---|---|---|---|---|---|---|---|---|---|---|---|
| Asp | Lys | Ile | Ser | Ser | Thr | Ile | Val | Ala | Gln | Ser | Ala | Asp | Val | Pro | Thr | |
| | | | 165 | | | | | 170 | | | | | 175 | | | |

| atg | ggc | tgg | tcc | gga | act | ggc | atc | aca | gag | act | acc | atg | gat | gct | aat | 576 |
|---|---|---|---|---|---|---|---|---|---|---|---|---|---|---|---|---|
| Met | Gly | Trp | Ser | Gly | Thr | Gly | Ile | Thr | Glu | Thr | Thr | Met | Asp | Ala | Asn | |
| | | 180 | | | | | 185 | | | | | 190 | | | | |

| ggt | ttc | gtc | atg | gtg | ccc | gag | gat | gct | tac | cag | gct | gcc | tgt | gtc | acc | 624 |
|---|---|---|---|---|---|---|---|---|---|---|---|---|---|---|---|---|
| Gly | Phe | Val | Met | Val | Pro | Glu | Asp | Ala | Tyr | Gln | Ala | Ala | Cys | Val | Thr | |
| | | | 195 | | | | | 200 | | | | | 205 | | | |

| gat | gca | gag | gat | ggt | ctt | cag | aag | gcc | cac | acc | atc | ggc | ttc | ccg | gtc | 672 |
|---|---|---|---|---|---|---|---|---|---|---|---|---|---|---|---|---|
| Asp | Ala | Glu | Asp | Gly | Leu | Gln | Lys | Ala | His | Thr | Ile | Gly | Phe | Pro | Val | |
| 210 | | | | | 215 | | | | | 220 | | | | | | |

| atg | atc | aag | gct | tca | gag | ggt | ggt | gga | gga | aag | ggt | att | cgt | aag | gtt | 720 |
|---|---|---|---|---|---|---|---|---|---|---|---|---|---|---|---|---|
| Met | Ile | Lys | Ala | Ser | Glu | Gly | Gly | Gly | Gly | Lys | Gly | Ile | Arg | Lys | Val | |
| 225 | | | | | 230 | | | | | 235 | | | | | 240 | |

| gag | gaa | cca | gaa | aag | ttc | gct | cag | gcc | ttc | aac | cag | gtt | ttg | ggc | gag | 768 |
|---|---|---|---|---|---|---|---|---|---|---|---|---|---|---|---|---|
| Glu | Glu | Pro | Glu | Lys | Phe | Ala | Gln | Ala | Phe | Asn | Gln | Val | Leu | Gly | Glu | |
| | | | | 245 | | | | | 250 | | | | | 255 | | |

| gtc | ccc | ggt | tcc | ccc | gtc | ttc | atc | atg | aag | ttg | gct | ggt | aac | gcg | cgc | 816 |
|---|---|---|---|---|---|---|---|---|---|---|---|---|---|---|---|---|
| Val | Pro | Gly | Ser | Pro | Val | Phe | Ile | Met | Lys | Leu | Ala | Gly | Asn | Ala | Arg | |

-continued

| | | | |
|---|---|---|---|
| | 260 | 265 | 270 |
| cat ctg gag gtc cag ctt ttg gcc gat cag tat gga aat gcc atc tcg<br>His Leu Glu Val Gln Leu Leu Ala Asp Gln Tyr Gly Asn Ala Ile Ser<br>          275                  280                  285 | | | 864 |
| ctc ttt gga cgc gat tgc tct gtc cag cgt cgc cat cag aag att att<br>Leu Phe Gly Arg Asp Cys Ser Val Gln Arg Arg His Gln Lys Ile Ile<br>290                  295                  300 | | | 912 |
| gag gaa gct ccc gtc acc att gcc aag ccc gac acc ttc gag tcg atg<br>Glu Glu Ala Pro Val Thr Ile Ala Lys Pro Asp Thr Phe Glu Ser Met<br>305                  310                  315                  320 | | | 960 |
| gag aag gct gca gtg cgt ctg gcc aag ttg gtc gga tac gtt tct gca<br>Glu Lys Ala Ala Val Arg Leu Ala Lys Leu Val Gly Tyr Val Ser Ala<br>                  325                  330                  335 | | | 1008 |
| ggt acc gtc gag tac ctg tac tcg cac tcg act gac acc ttc ttc ttc<br>Gly Thr Val Glu Tyr Leu Tyr Ser His Ser Thr Asp Thr Phe Phe Phe<br>                  340                  345                  350 | | | 1056 |
| ctg gag ttg aac ccc aga ctt cag gtc gag cat cct acc acc gag atg<br>Leu Glu Leu Asn Pro Arg Leu Gln Val Glu His Pro Thr Thr Glu Met<br>                  355                  360                  365 | | | 1104 |
| gtc tca ggt gtc aac ctg cca gct gct cag ctc cag atc gcc atg ggt<br>Val Ser Gly Val Asn Leu Pro Ala Ala Gln Leu Gln Ile Ala Met Gly<br>370                  375                  380 | | | 1152 |
| ctt cct ttg aac cgc atc aag gac atc cgt gtt ctc tat ggt ctt caa<br>Leu Pro Leu Asn Arg Ile Lys Asp Ile Arg Val Leu Tyr Gly Leu Gln<br>385                  390                  395                  400 | | | 1200 |
| ccc aca gga acg tcc gag atc gac ttt gag ttt tca cag cag atc tcg<br>Pro Thr Gly Thr Ser Glu Ile Asp Phe Glu Phe Ser Gln Gln Ile Ser<br>                  405                  410                  415 | | | 1248 |
| tat gag act cag cgc aag ccc gcc cct aag gga cac gtc att gct gtc<br>Tyr Glu Thr Gln Arg Lys Pro Ala Pro Lys Gly His Val Ile Ala Val<br>                  420                  425                  430 | | | 1296 |
| cgt atc aca gcc gag aac ccc gat gca gga ttc aag ccc tca agc gga<br>Arg Ile Thr Ala Glu Asn Pro Asp Ala Gly Phe Lys Pro Ser Ser Gly<br>                  435                  440                  445 | | | 1344 |
| atg atg cag gaa ctc aat ttc aga tca tct acc aac gtc tgg ggc tac<br>Met Met Gln Glu Leu Asn Phe Arg Ser Ser Thr Asn Val Trp Gly Tyr<br>450                  455                  460 | | | 1392 |
| ttc tct gtc aac tct gca gga gga ctg cac gag ttt gcc gat tct cag<br>Phe Ser Val Asn Ser Ala Gly Gly Leu His Glu Phe Ala Asp Ser Gln<br>465                  470                  475                  480 | | | 1440 |
| ttt ggt cat atc ttt gcc tat gga cag gat cgt ggt cag tct aga aag<br>Phe Gly His Ile Phe Ala Tyr Gly Gln Asp Arg Gly Gln Ser Arg Lys<br>                  485                  490                  495 | | | 1488 |
| aac atg gtc gtt gcc ctc aag gaa ctc tcc att cgt ggt gat ttc cgc<br>Asn Met Val Val Ala Leu Lys Glu Leu Ser Ile Arg Gly Asp Phe Arg<br>                  500                  505                  510 | | | 1536 |
| act acg gtc gag tac ttg atc cgc ctt ttg gag aca cag gag ttc gag<br>Thr Thr Val Glu Tyr Leu Ile Arg Leu Leu Glu Thr Gln Glu Phe Glu<br>                  515                  520                  525 | | | 1584 |
| gaa aac acc att aac act ggc tgg ctc gac agc ttg atc tcc aac aac<br>Glu Asn Thr Ile Asn Thr Gly Trp Leu Asp Ser Leu Ile Ser Asn Asn<br>530                  535                  540 | | | 1632 |
| ctc act gct gaa cgc cct gag acc atg ttg gct gtc atg tgt ggt gct<br>Leu Thr Ala Glu Arg Pro Glu Thr Met Leu Ala Val Met Cys Gly Ala<br>545                  550                  555                  560 | | | 1680 |
| gtt aac aga gcc cac acc atc tcc gag aac tgc att aag gag tac aag<br>Val Asn Arg Ala His Thr Ile Ser Glu Asn Cys Ile Lys Glu Tyr Lys<br>                  565                  570                  575 | | | 1728 |
| aag tcg ctg gag aag ggt caa gtg cct agc aag gac gtt ctg cgc tcg | | | 1776 |

|                                                                                      |      |
|--------------------------------------------------------------------------------------|------|
| Lys Ser Leu Glu Lys Gly Gln Val Pro Ser Lys Asp Val Leu Arg Ser<br>580             585             590 |      |
| gtc aac cag ctt gac ttt att tac gac ggc gtc cgc tac aac ttc acc<br>Val Asn Gln Leu Asp Phe Ile Tyr Asp Gly Val Arg Tyr Asn Phe Thr<br>595             600             605 | 1824 |
| gcc act cgc tct gga ccc aac tcg tac act ctg tac ttg aat gga tcc<br>Ala Thr Arg Ser Gly Pro Asn Ser Tyr Thr Leu Tyr Leu Asn Gly Ser<br>610             615             620 | 1872 |
| atg atc tcc atc tct gtg cgt cca ttg acc gat ggc ggt ctc ttg gtc<br>Met Ile Ser Ile Ser Val Arg Pro Leu Thr Asp Gly Gly Leu Leu Val<br>625             630             635             640 | 1920 |
| ctt ttg gat ggc aag gct cac acg act tac tcg ttg gaa gag gtc cag<br>Leu Leu Asp Gly Lys Ala His Thr Thr Tyr Ser Leu Glu Glu Val Gln<br>645             650             655 | 1968 |
| gcc act cgc ctg atg gtc gat gga aag act tgt ttg ttg gag aag gag<br>Ala Thr Arg Leu Met Val Asp Gly Lys Thr Cys Leu Leu Glu Lys Glu<br>660             665             670 | 2016 |
| aac gac cct act caa ctc cgc tcc ccc tcc cca ggc aaa ctt gtt cgc<br>Asn Asp Pro Thr Gln Leu Arg Ser Pro Ser Pro Gly Lys Leu Val Arg<br>675             680             685 | 2064 |
| tac ctt gtc gag tct ggc gac cat gtt acg gcc agc cag gcc tat gct<br>Tyr Leu Val Glu Ser Gly Asp His Val Thr Ala Ser Gln Ala Tyr Ala<br>690             695             700 | 2112 |
| gag att gag gtc atg aag atg tat atg ccc ttg atc gcc acc gag gac<br>Glu Ile Glu Val Met Lys Met Tyr Met Pro Leu Ile Ala Thr Glu Asp<br>705             710             715             720 | 2160 |
| ggt att gtg cag ttc atc aag caa ccc ggc acc act ctg gat gct ggt<br>Gly Ile Val Gln Phe Ile Lys Gln Pro Gly Thr Thr Leu Asp Ala Gly<br>725             730             735 | 2208 |
| gat atc att ggt atc ctc agc ttg gac gat ccc tcc cgc gtt cgc cac<br>Asp Ile Ile Gly Ile Leu Ser Leu Asp Asp Pro Ser Arg Val Arg His<br>740             745             750 | 2256 |
| gct aag ccc ttc gaa ggt cag ctc cct ccc atg ggt cag ccc acc att<br>Ala Lys Pro Phe Glu Gly Gln Leu Pro Pro Met Gly Gln Pro Thr Ile<br>755             760             765 | 2304 |
| cac gga gct aag ccc cat cag cgt tac cgc gag ctg cga ctc gtc ctc<br>His Gly Ala Lys Pro His Gln Arg Tyr Arg Glu Leu Arg Leu Val Leu<br>770             775             780 | 2352 |
| gac aat gcc atg gat ggc tac gat aac cag gct ttg gtc cag cct acg<br>Asp Asn Ala Met Asp Gly Tyr Asp Asn Gln Ala Leu Val Gln Pro Thr<br>785             790             795             800 | 2400 |
| ctg aag gag atc ttt gag gtc ctc cag acc ccg gag ctg ccc tac ttg<br>Leu Lys Glu Ile Phe Glu Val Leu Gln Thr Pro Glu Leu Pro Tyr Leu<br>805             810             815 | 2448 |
| gaa ttc aac gag gtc ttt gct tcg cta agc gga aga atc cca ccc aag<br>Glu Phe Asn Glu Val Phe Ala Ser Leu Ser Gly Arg Ile Pro Pro Lys<br>820             825             830 | 2496 |
| ctg gaa att gcc ctg cac cag gag gtg gat cag tcc atg aag aac cac<br>Leu Glu Ile Ala Leu His Gln Glu Val Asp Gln Ser Met Lys Asn His<br>835             840             845 | 2544 |
| gag cac ttc ccc gct cgt act ctt cag gcc ctg att gac tcg cac tgc<br>Glu His Phe Pro Ala Arg Thr Leu Gln Ala Leu Ile Asp Ser His Cys<br>850             855             860 | 2592 |
| cgc gcc aac ttc tcc aag gcc gcc gat atc aat gcg ttc caa gcc tcg<br>Arg Ala Asn Phe Ser Lys Ala Ala Asp Ile Asn Ala Phe Gln Ala Ser<br>865             870             875             880 | 2640 |
| gtg gga cct ctg acc gcc atc atc aag gag tac caa cac ggt ttg aaa<br>Val Gly Pro Leu Thr Ala Ile Ile Lys Glu Tyr Gln His Gly Leu Lys<br>885             890             895 | 2688 |

-continued

| | |
|---|---|
| act cac tcc tgg ggc ttc att gct gat tac ctc aac aag tac cat gaa<br>Thr His Ser Trp Gly Phe Ile Ala Asp Tyr Leu Asn Lys Tyr His Glu<br>                  900                 905                910 | 2736 |
| gtc gag tcg ctc ttt gat gac tct gct cgt gag gaa gag atc ttc ctg<br>Val Glu Ser Leu Phe Asp Asp Ser Ala Arg Glu Glu Glu Ile Phe Leu<br>                  915                 920                925 | 2784 |
| tcc ctg cgt gat cag aac aag gac gac gtc gag aag gtc atc cgc atc<br>Ser Leu Arg Asp Gln Asn Lys Asp Asp Val Glu Lys Val Ile Arg Ile<br>   930                 935                940 | 2832 |
| gca ctc tcg cac tcg cgt gtc act gcc aag aac aac ttg gtt ttg acc<br>Ala Leu Ser His Ser Arg Val Thr Ala Lys Asn Asn Leu Val Leu Thr<br>945                  950                955                960 | 2880 |
| ctt ctt gac cag atc aaa cct acg gcc tct gga gga gcg ctc gac aag<br>Leu Leu Asp Gln Ile Lys Pro Thr Ala Ser Gly Gly Ala Leu Asp Lys<br>                  965                 970                975 | 2928 |
| ttc ttc tcg cct gtg ctc aag aag ctg gct gag ctt act ggc cgt ctc<br>Phe Phe Ser Pro Val Leu Lys Lys Leu Ala Glu Leu Thr Gly Arg Leu<br>   980                 985                990 | 2976 |
| acc gcc aag gtc tcg ctc aag gcc aga gag ctc ctt att cat gtt cag<br>Thr Ala Lys Val Ser Leu Lys Ala Arg Glu Leu Leu Ile His Val Gln<br>                  995                 1000              1005 | 3024 |
| ttg ccc agc ttt gag gaa cgc cag tcg cag atg gag aag atc ctc<br>Leu Pro Ser Phe Glu Glu Arg Gln Ser Gln Met Glu Lys Ile Leu<br>  1010                 1015              1020 | 3069 |
| cgc tcg agc gtc act gag gag gtt tat ggt ggt gaa cac gag gcc<br>Arg Ser Ser Val Thr Glu Glu Val Tyr Gly Gly Glu His Glu Ala<br>  1025                 1030              1035 | 3114 |
| cgc atg cct gcc ttt gag aac atc aag gag ttg gtc gac acc acc<br>Arg Met Pro Ala Phe Glu Asn Ile Lys Glu Leu Val Asp Thr Thr<br>  1040                 1045              1050 | 3159 |
| tac aca gtc ttt gat gtc ttg cct aac ttc ttt tac cat gag tcg<br>Tyr Thr Val Phe Asp Val Leu Pro Asn Phe Phe Tyr His Glu Ser<br>  1055                 1060              1065 | 3204 |
| ttg cat gtc cgc att gcc gcg ttc gag gtg tac tgc cgt cgt gcc<br>Leu His Val Arg Ile Ala Ala Phe Glu Val Tyr Cys Arg Arg Ala<br>  1070                 1075              1080 | 3249 |
| tac cat gcg tac gag att ttg gac atc aat tac cac atg gag cac<br>Tyr His Ala Tyr Glu Ile Leu Asp Ile Asn Tyr His Met Glu His<br>  1085                 1090              1095 | 3294 |
| cag ccc ttg ctg atc act tgg aag ttc ttg ctc aac acc ccc aac<br>Gln Pro Leu Leu Ile Thr Trp Lys Phe Leu Leu Asn Thr Pro Asn<br>  1100                 1105              1110 | 3339 |
| aag tcc gag tct ggt ccc aac cgt gtg gct agt gtc agt gac atg<br>Lys Ser Glu Ser Gly Pro Asn Arg Val Ala Ser Val Ser Asp Met<br>  1115                 1120              1125 | 3384 |
| agt tac ttg atc aac aag gct gac cct gag cct gtt cgt acc ggt<br>Ser Tyr Leu Ile Asn Lys Ala Asp Pro Glu Pro Val Arg Thr Gly<br>  1130                 1135              1140 | 3429 |
| gcc att ctt gcc gtt cgc gac gtg aag gag ctg gag gac aga ttc<br>Ala Ile Leu Ala Val Arg Asp Val Lys Glu Leu Glu Asp Arg Phe<br>  1145                 1150              1155 | 3474 |
| gag agc atc ctc aac ttc ttc ccc tct cac aag tcg aac aag cac<br>Glu Ser Ile Leu Asn Phe Phe Pro Ser His Lys Ser Asn Lys His<br>  1160                 1165              1170 | 3519 |
| ttg agc cat ctc gct gcc gcc agc gtc cac aac aat gtg ttg aac<br>Leu Ser His Leu Ala Ala Ala Ser Val His Asn Asn Val Leu Asn<br>  1175                 1180              1185 | 3564 |
| gtt gtc atc aag tcc gag tcg gtt cac ccc aac gat gat gac tac<br>Val Val Ile Lys Ser Glu Ser Val His Pro Asn Asp Asp Asp Tyr<br>  1190                 1195              1200 | 3609 |

-continued

```
tgg ctg aac ctc ctc agc ccc atc gtg aag ggc gag acc gag cgc      3654
Trp Leu Asn Leu Leu Ser Pro Ile Val Lys Gly Glu Thr Glu Arg
    1205            1210                1215 ctt cgc tcg cac ggc atc cgt cgc atg acc ttc ttg atc ttc cgt      3699
Leu Arg Ser His Gly Ile Arg Arg Met Thr Phe Leu Ile Phe Arg
    1220            1225                1230 cag ggc aac tac ccc tcg tac ttc acc ttc cgt gag cgt aac aac      3744
Gln Gly Asn Tyr Pro Ser Tyr Phe Thr Phe Arg Glu Arg Asn Asn
    1235            1240                1245 tac gct gag gat cag acc atc cgt cac atc gag ccc gcc atg gca      3789
Tyr Ala Glu Asp Gln Thr Ile Arg His Ile Glu Pro Ala Met Ala
    1250            1255                1260 tac cgt ctt gag ttg gcg cgc ttg tcc aac ttt gac atc aag ccc      3834
Tyr Arg Leu Glu Leu Ala Arg Leu Ser Asn Phe Asp Ile Lys Pro
    1265            1270                1275 tgc ttc att gac aat cgc cag gtt cat gtg tac tat gct gtg ggc      3879
Cys Phe Ile Asp Asn Arg Gln Val His Val Tyr Tyr Ala Val Gly
    1280            1285                1290 aag gag aac att tcg gac tgc cgc ttc ttt gtc tgc gcc ttg gtt      3924
Lys Glu Asn Ile Ser Asp Cys Arg Phe Phe Val Cys Ala Leu Val
    1295            1300                1305 cgt cct ggt cgc ctg cgc tct agc gtt cgt acg gcg gat tac ttg      3969
Arg Pro Gly Arg Leu Arg Ser Ser Val Arg Thr Ala Asp Tyr Leu
    1310            1315                1320 att tcg gag acc gac cgt ctg ttg aac gat att ctg gat gct ctg      4014
Ile Ser Glu Thr Asp Arg Leu Leu Asn Asp Ile Leu Asp Ala Leu
    1325            1330                1335 gag att gtg ggt gcc acc tac aag cag agt gac tgc aac cac ttg      4059
Glu Ile Val Gly Ala Thr Tyr Lys Gln Ser Asp Cys Asn His Leu
    1340            1345                1350 ttt atc aac ttc atc ccc act ttc cag ttg gac gct acc gag gtt      4104
Phe Ile Asn Phe Ile Pro Thr Phe Gln Leu Asp Ala Thr Glu Val
    1355            1360                1365 gag act gcc ctc aag gga ttc att gac cgc cac ggc aag cgt ctc      4149
Glu Thr Ala Leu Lys Gly Phe Ile Asp Arg His Gly Lys Arg Leu
    1370            1375                1380 tgg cgt ctt cgc gtc act ggc gct gag att cgc ttc aat gtt cag      4194
Trp Arg Leu Arg Val Thr Gly Ala Glu Ile Arg Phe Asn Val Gln
    1385            1390                1395 tcc aag tct gcg aat ggc gtt gag gcc gac ccc gtt cct ctt cga      4239
Ser Lys Ser Ala Asn Gly Val Glu Ala Asp Pro Val Pro Leu Arg
    1400            1405                1410 ttc atc atc tcc aac gtc tct gga tat gtc ttg aac gtc gac acc      4284
Phe Ile Ile Ser Asn Val Ser Gly Tyr Val Leu Asn Val Asp Thr
    1415            1420                1425 tac cgc gag gtt cag acc gag aag ggt gcc atc ttc aag tcg gtt      4329
Tyr Arg Glu Val Gln Thr Glu Lys Gly Ala Ile Phe Lys Ser Val
    1430            1435                1440 ggt cct acc ggt ccc ttc cat ctc ttg cct gtg aac cag ccc tac      4374
Gly Pro Thr Gly Pro Phe His Leu Leu Pro Val Asn Gln Pro Tyr
    1445            1450                1455 ccc aca aag gag tgg ctt cag ccc aga cgt tac aag gca cac ttg      4419
Pro Thr Lys Glu Trp Leu Gln Pro Arg Arg Tyr Lys Ala His Leu
    1460            1465                1470 atg ggc acg act tac gtc tat gac ttt ggc gag ctc ttc cgc cag      4464
Met Gly Thr Thr Tyr Val Tyr Asp Phe Gly Glu Leu Phe Arg Gln
    1475            1480                1485 gcc gtc cgt gct cag tgg aac cat gcc atc aag cag aac tct tcg      4509
Ala Val Arg Ala Gln Trp Asn His Ala Ile Lys Gln Asn Ser Ser
```

-continued

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     | 1490 |     |     |     | 1495 |     |     |     | 1500 |     |     |     |      |
| ctc | aag | gtc | cca | tcc | cag | gtc | ttg | gag | atg | cgc | gag | ctg | gtc | ttg | 4554 |
| Leu | Lys | Val | Pro | Ser | Gln | Val | Leu | Glu | Met | Arg | Glu | Leu | Val | Leu |      |
|     | 1505 |     |     |     | 1510 |     |     |     | 1515 |     |     |     |     |     |      |
| gat | gag | aga | cag | cag | ttg | cag | cag | gtc | gtt | cgc | gat | gcc | ggt | tcc | 4599 |
| Asp | Glu | Arg | Gln | Gln | Leu | Gln | Gln | Val | Val | Arg | Asp | Ala | Gly | Ser |      |
| 1520 |     |     |     | 1525 |     |     |     | 1530 |     |     |     |     |     |     |      |
| aac | aac | tgc | ggc | atg | gtt | gcc | tgg | att | ttc | act | ctc | cgt | acc | ccc | 4644 |
| Asn | Asn | Cys | Gly | Met | Val | Ala | Trp | Ile | Phe | Thr | Leu | Arg | Thr | Pro |      |
|     | 1535 |     |     |     | 1540 |     |     |     | 1545 |     |     |     |     |     |      |
| gag | tac | ccc | gag | ggt | cga | cag | atc | att | gtc | att | gcc | aac | gat | atc | 4689 |
| Glu | Tyr | Pro | Glu | Gly | Arg | Gln | Ile | Ile | Val | Ile | Ala | Asn | Asp | Ile |      |
|     |     | 1550 |     |     |     | 1555 |     |     |     | 1560 |     |     |     |     |      |
| acc | ttc | aac | att | gga | tcg | ttt | gga | ccc | gag | gag | gac | ctg | gtc | ttc | 4734 |
| Thr | Phe | Asn | Ile | Gly | Ser | Phe | Gly | Pro | Glu | Glu | Asp | Leu | Val | Phe |      |
|     |     | 1565 |     |     |     | 1570 |     |     |     | 1575 |     |     |     |     |      |
| tac | aag | gcg | tcc | gag | atg | gcc | aga | aag | ttg | ggc | att | ccc | cgt | gtt | 4779 |
| Tyr | Lys | Ala | Ser | Glu | Met | Ala | Arg | Lys | Leu | Gly | Ile | Pro | Arg | Val |      |
|     | 1580 |     |     |     | 1585 |     |     |     | 1590 |     |     |     |     |     |      |
| tac | ctc | tct | gcc | aac | tct | ggt | gcc | cgc | att | ggt | ctt | gct | agt | gaa | 4824 |
| Tyr | Leu | Ser | Ala | Asn | Ser | Gly | Ala | Arg | Ile | Gly | Leu | Ala | Ser | Glu |      |
|     | 1595 |     |     |     | 1600 |     |     |     | 1605 |     |     |     |     |     |      |
| gtg | att | ggt | ctc | ttc | aac | tct | tgc | tgg | aac | gac | gct | tcc | aac | ccc | 4869 |
| Val | Ile | Gly | Leu | Phe | Asn | Ser | Cys | Trp | Asn | Asp | Ala | Ser | Asn | Pro |      |
| 1610 |     |     |     | 1615 |     |     |     | 1620 |     |     |     |     |     |     |      |
| tcc | aag | ggc | ttc | aag | tac | atc | tac | ctc | acg | gac | gct | gga | ctg | aag | 4914 |
| Ser | Lys | Gly | Phe | Lys | Tyr | Ile | Tyr | Leu | Thr | Asp | Ala | Gly | Leu | Lys |      |
|     | 1625 |     |     |     | 1630 |     |     |     | 1635 |     |     |     |     |     |      |
| cag | ttg | gag | gct | cag | gag | gag | cgc | tct | ggt | aag | aag | agc | gtc | atc | 4959 |
| Gln | Leu | Glu | Ala | Gln | Glu | Glu | Arg | Ser | Gly | Lys | Lys | Ser | Val | Ile |      |
|     | 1640 |     |     |     | 1645 |     |     |     | 1650 |     |     |     |     |     |      |
| aca | gag | acc | att | gtt | gag | gat | ggc | gag | acc | cgc | cat | aag | atc | acg | 5004 |
| Thr | Glu | Thr | Ile | Val | Glu | Asp | Gly | Glu | Thr | Arg | His | Lys | Ile | Thr |      |
| 1655 |     |     |     | 1660 |     |     |     | 1665 |     |     |     |     |     |     |      |
| gat | gtc | atc | ggt | gct | gtc | gac | ggt | ctt | ggt | gtt | gag | aac | ttg | cgc | 5049 |
| Asp | Val | Ile | Gly | Ala | Val | Asp | Gly | Leu | Gly | Val | Glu | Asn | Leu | Arg |      |
|     | 1670 |     |     |     | 1675 |     |     |     | 1680 |     |     |     |     |     |      |
| gga | agt | ggt | ctg | att | gct | gga | gag | acc | tcg | cga | gcc | tac | gac | gac | 5094 |
| Gly | Ser | Gly | Leu | Ile | Ala | Gly | Glu | Thr | Ser | Arg | Ala | Tyr | Asp | Asp |      |
|     | 1685 |     |     |     | 1690 |     |     |     | 1695 |     |     |     |     |     |      |
| atc | ttt | acc | att | act | ttg | gtc | acc | tgc | cgc | tct | gtt | ggt | atc | ggt | 5139 |
| Ile | Phe | Thr | Ile | Thr | Leu | Val | Thr | Cys | Arg | Ser | Val | Gly | Ile | Gly |      |
| 1700 |     |     |     | 1705 |     |     |     | 1710 |     |     |     |     |     |     |      |
| gcg | tac | ttg | gtt | cgt | ttg | ggt | cag | cgt | act | att | cag | aat | gag | ggc | 5184 |
| Ala | Tyr | Leu | Val | Arg | Leu | Gly | Gln | Arg | Thr | Ile | Gln | Asn | Glu | Gly |      |
|     | 1715 |     |     |     | 1720 |     |     |     | 1725 |     |     |     |     |     |      |
| cag | ccc | atc | att | ttg | act | ggt | gcc | cct | gcc | ctc | aac | aag | ttg | ctt | 5229 |
| Gln | Pro | Ile | Ile | Leu | Thr | Gly | Ala | Pro | Ala | Leu | Asn | Lys | Leu | Leu |      |
| 1730 |     |     |     | 1735 |     |     |     | 1740 |     |     |     |     |     |     |      |
| ggt | cgc | gat | gtc | tac | acc | tcg | aac | ttg | cag | ctc | gga | ggc | act | cag | 5274 |
| Gly | Arg | Asp | Val | Tyr | Thr | Ser | Asn | Leu | Gln | Leu | Gly | Gly | Thr | Gln |      |
|     | 1745 |     |     |     | 1750 |     |     |     | 1755 |     |     |     |     |     |      |
| att | atg | tac | aag | aac | gga | gtg | tcg | cac | ttg | acc | gct | cag | aac | gac | 5319 |
| Ile | Met | Tyr | Lys | Asn | Gly | Val | Ser | His | Leu | Thr | Ala | Gln | Asn | Asp |      |
| 1760 |     |     |     | 1765 |     |     |     | 1770 |     |     |     |     |     |     |      |
| tat | gag | ggt | att | ggc | aag | atc | gtc | aac | tgg | ctc | tcg | tac | att | cct | 5364 |
| Tyr | Glu | Gly | Ile | Gly | Lys | Ile | Val | Asn | Trp | Leu | Ser | Tyr | Ile | Pro |      |
|     | 1775 |     |     |     | 1780 |     |     |     | 1785 |     |     |     |     |     |      |
| gag | cgc | aag | aat | gca | ccg | gtg | ccc | atc | acg | gtc | agc | aac | gac | acc | 5409 |

```
                                                     -continued

Glu Arg Lys Asn Ala Pro Val Pro Ile Thr Val Ser Asn Asp Thr
    1790            1795                1800 tgg gac cgc gac atc gac tac ttg cct ccc aag ggt gca gtc tat    5454
Trp Asp Arg Asp Ile Asp Tyr Leu Pro Pro Lys Gly Ala Val Tyr
    1805            1810                1815 gat ccc cgc tgg ttg atc gct ggt aag gag gct gag gag gag ggc    5499
Asp Pro Arg Trp Leu Ile Ala Gly Lys Glu Ala Glu Glu Glu Gly
    1820            1825                1830 gcc tct ttc cag act ggt ttc ttc gac aag gat tcg ttt acc gag    5544
Ala Ser Phe Gln Thr Gly Phe Phe Asp Lys Asp Ser Phe Thr Glu
    1835            1840                1845 aca ttg acg ggc tgg gcc cgc acg gtt gtt gtt gga cgt gcc cgt    5589
Thr Leu Thr Gly Trp Ala Arg Thr Val Val Val Gly Arg Ala Arg
    1850            1855                1860 ctc ggt ggt gtc cct atg gga gtg att gca gtt gag acc cgc tcg    5634
Leu Gly Gly Val Pro Met Gly Val Ile Ala Val Glu Thr Arg Ser
    1865            1870                1875 gtc gag cac atc atc cct gct gat ccc gcc aac ggc gac tct gtc    5679
Val Glu His Ile Ile Pro Ala Asp Pro Ala Asn Gly Asp Ser Val
    1880            1885                1890 gag cag gtc ttg atg gag gct gga aat gtt tgg tac ccc aac tcg    5724
Glu Gln Val Leu Met Glu Ala Gly Asn Val Trp Tyr Pro Asn Ser
    1895            1900                1905 gct tac aag act gcg cag gcc atc aac gac ttc aac aag gga gag    5769
Ala Tyr Lys Thr Ala Gln Ala Ile Asn Asp Phe Asn Lys Gly Glu
    1910            1915                1920 cag ctt cca ctg atg atc ttt gcc aac tgg cgt gga ttc tcg ggt    5814
Gln Leu Pro Leu Met Ile Phe Ala Asn Trp Arg Gly Phe Ser Gly
    1925            1930                1935 ggt cag cgc gac atg tac aat gag atc ctc aag tac ggt tcc ttc    5859
Gly Gln Arg Asp Met Tyr Asn Glu Ile Leu Lys Tyr Gly Ser Phe
    1940            1945                1950 att gtc gat gct ctg agc tca tac aag cag cct gtg ttt gtc tat    5904
Ile Val Asp Ala Leu Ser Ser Tyr Lys Gln Pro Val Phe Val Tyr
    1955            1960                1965 gtg gtt ccc aac gga gag ctt cgt gga ggt gct tgg gtc gtc gtt    5949
Val Val Pro Asn Gly Glu Leu Arg Gly Gly Ala Trp Val Val Val
    1970            1975                1980 gac cct act atc aac gag gac atg atg gag atg tat gct gac aag    5994
Asp Pro Thr Ile Asn Glu Asp Met Met Glu Met Tyr Ala Asp Lys
    1985            1990                1995 cgg tca aga gcc ggt gtc ttg gag cct gag ggt att gtt gag atc    6039
Arg Ser Arg Ala Gly Val Leu Glu Pro Glu Gly Ile Val Glu Ile
    2000            2005                2010 aag ttc cgt aag gcc cag ttg ttg gcg acc atg gag cgt ttg gac    6084
Lys Phe Arg Lys Ala Gln Leu Leu Ala Thr Met Glu Arg Leu Asp
    2015            2020                2025 gac aag tac cgc gca ttg aag gcc cag tac gag aac cca gcc ttg    6129
Asp Lys Tyr Arg Ala Leu Lys Ala Gln Tyr Glu Asn Pro Ala Leu
    2030            2035                2040 gtt ggt acc gag cgc gag gag atc aag acg aag ctg acg gag cgc    6174
Val Gly Thr Glu Arg Glu Glu Ile Lys Thr Lys Leu Thr Glu Arg
    2045            2050                2055 gag caa gag ctg ttg cct gtg tac cag cag ctg gcg atc caa ttc    6219
Glu Gln Glu Leu Leu Pro Val Tyr Gln Gln Leu Ala Ile Gln Phe
    2060            2065                2070 gcg gat ctg cac gac act gcg gga cgc atg aag gcc aag ggc acg    6264
Ala Asp Leu His Asp Thr Ala Gly Arg Met Lys Ala Lys Gly Thr
    2075            2080                2085
```

```
att cgt gaa gcc ttg gac tgg acc aat gcc cgt cgc tac ttc tac    6309
Ile Arg Glu Ala Leu Asp Trp Thr Asn Ala Arg Arg Tyr Phe Tyr
    2090            2095                2100 tgg cgc gtg cgc aga aga ttg gct gag gag tac att cgt cgc aag    6354
Trp Arg Val Arg Arg Arg Leu Ala Glu Glu Tyr Ile Arg Arg Lys
2105            2110                2115 atg gct att gcc aac aag gac ttg agc cgt gag gag cag acc aag    6399
Met Ala Ile Ala Asn Lys Asp Leu Ser Arg Glu Glu Gln Thr Lys
    2120            2125                2130 tcg ctg ctg tct tgg ttc ggc cgt gac acg gtg cac tcg agc gag    6444
Ser Leu Leu Ser Trp Phe Gly Arg Asp Thr Val His Ser Ser Glu
2135            2140                2145 agc gag ctg gag cag atc tgg gaa tct gac gat cgc gtg gtg ttg    6489
Ser Glu Leu Glu Gln Ile Trp Glu Ser Asp Asp Arg Val Val Leu
    2150            2155                2160 gag tgg ttc gag gga cac gag agc aag gtg act gga ttg atc cag    6534
Glu Trp Phe Glu Gly His Glu Ser Lys Val Thr Gly Leu Ile Gln
2165            2170                2175 gag ctg aac aat gcg gcg act gcc agc gag gtg ctg aga atg tac    6579
Glu Leu Asn Asn Ala Ala Thr Ala Ser Glu Val Leu Arg Met Tyr
    2180            2185                2190 acc tcc aac cgc gct ggt gtg gtc gag ggc ttc gat cgt atc ctt    6624
Thr Ser Asn Arg Ala Gly Val Val Glu Gly Phe Asp Arg Ile Leu
2195            2200                2205 cag agc ctg tcg gac cag gag aag cag gac atc ctt gcc aag ttc    6669
Gln Ser Leu Ser Asp Gln Glu Lys Gln Asp Ile Leu Ala Lys Phe
    2210            2215                2220 gcc acg atg acc gtt                                             6684
Ala Thr Met Thr Val
2225

<210> SEQ ID NO 2
<211> LENGTH: 2228
<212> TYPE: PRT
<213> ORGANISM: Mortierella alpina

<400> SEQUENCE: 2

Met Thr Thr Asn Val Gln Ser Phe Ile Gly Gly Asn Ala Leu Glu Asn
1               5                   10                  15

Ala Pro Ala Gly Ala Val Arg Glu Phe Val Asn Gln His Gly Gly His
                20                  25                  30

Ser Val Ile Thr Lys Ile Leu Ile Ala Asn Asn Gly Ile Ala Ala Val
            35                  40                  45

Lys Glu Ile Arg Ser Val Arg Lys Trp Ala Tyr Glu Thr Phe Gly Asp
50                  55                  60

Glu Arg Ala Ile Gln Phe Thr Val Met Ala Thr Pro Glu Asp Leu Lys
65                  70                  75                  80

Ile Asn Ala Glu Tyr Ile Arg Met Ala Asp Gln Tyr Val Glu Val Pro
                85                  90                  95

Gly Gly Ser Asn Asn Asn Tyr Ala Asn Val Asp Leu Ile Val Asp
                100                 105                 110

Ile Ala Glu Arg Thr Gly Val His Ala Val Trp Ala Gly Trp Gly His
            115                 120                 125

Ala Ser Glu Asn Pro Lys Leu Pro Glu Ser Leu Arg Asp Ser Pro Gln
        130                 135                 140

Lys Ile Ile Phe Ile Gly Pro Pro Gly Ser Ala Met Arg Ser Leu Gly
145                 150                 155                 160

Asp Lys Ile Ser Ser Thr Ile Val Ala Gln Ser Ala Asp Val Pro Thr
```

```
                165                 170                 175
Met Gly Trp Ser Gly Thr Gly Ile Thr Glu Thr Thr Met Asp Ala Asn
            180                 185                 190
Gly Phe Val Met Val Pro Glu Asp Ala Tyr Gln Ala Ala Cys Val Thr
        195                 200                 205
Asp Ala Glu Asp Gly Leu Gln Lys Ala His Thr Ile Gly Phe Pro Val
    210                 215                 220
Met Ile Lys Ala Ser Glu Gly Gly Gly Lys Gly Ile Arg Lys Val
225                 230                 235                 240
Glu Glu Pro Glu Lys Phe Ala Gln Ala Phe Asn Gln Val Leu Gly Glu
                245                 250                 255
Val Pro Gly Ser Pro Val Phe Ile Met Lys Leu Ala Gly Asn Ala Arg
            260                 265                 270
His Leu Glu Val Gln Leu Leu Ala Asp Gln Tyr Gly Asn Ala Ile Ser
        275                 280                 285
Leu Phe Gly Arg Asp Cys Ser Val Gln Arg His Gln Lys Ile Ile
    290                 295                 300
Glu Glu Ala Pro Val Thr Ile Ala Lys Pro Asp Thr Phe Glu Ser Met
305                 310                 315                 320
Glu Lys Ala Ala Val Arg Leu Ala Lys Leu Val Gly Tyr Val Ser Ala
                325                 330                 335
Gly Thr Val Glu Tyr Leu Tyr Ser His Ser Thr Asp Thr Phe Phe Phe
            340                 345                 350
Leu Glu Leu Asn Pro Arg Leu Gln Val Glu His Pro Thr Thr Glu Met
        355                 360                 365
Val Ser Gly Val Asn Leu Pro Ala Ala Gln Leu Gln Ile Ala Met Gly
    370                 375                 380
Leu Pro Leu Asn Arg Ile Lys Asp Ile Arg Val Leu Tyr Gly Leu Gln
385                 390                 395                 400
Pro Thr Gly Thr Ser Glu Ile Asp Phe Glu Phe Ser Gln Gln Ile Ser
                405                 410                 415
Tyr Glu Thr Gln Arg Lys Pro Ala Pro Lys Gly His Val Ile Ala Val
            420                 425                 430
Arg Ile Thr Ala Glu Asn Pro Asp Ala Gly Phe Lys Pro Ser Ser Gly
        435                 440                 445
Met Met Gln Glu Leu Asn Phe Arg Ser Ser Thr Asn Val Trp Gly Tyr
    450                 455                 460
Phe Ser Val Asn Ser Ala Gly Gly Leu His Glu Phe Ala Asp Ser Gln
465                 470                 475                 480
Phe Gly His Ile Phe Ala Tyr Gly Gln Asp Arg Gly Gln Ser Arg Lys
                485                 490                 495
Asn Met Val Val Ala Leu Lys Glu Leu Ser Ile Arg Gly Asp Phe Arg
            500                 505                 510
Thr Thr Val Glu Tyr Leu Ile Arg Leu Leu Glu Thr Gln Glu Phe Glu
        515                 520                 525
Glu Asn Thr Ile Asn Thr Gly Trp Leu Asp Ser Leu Ile Ser Asn Asn
    530                 535                 540
Leu Thr Ala Glu Arg Pro Glu Thr Met Leu Ala Val Met Cys Gly Ala
545                 550                 555                 560
Val Asn Arg Ala His Thr Ile Ser Glu Asn Cys Ile Lys Glu Tyr Lys
                565                 570                 575
Lys Ser Leu Glu Lys Gly Gln Val Pro Ser Lys Asp Val Leu Arg Ser
            580                 585                 590
```

```
Val Asn Gln Leu Asp Phe Ile Tyr Asp Gly Val Arg Tyr Asn Phe Thr
        595                 600                 605
Ala Thr Arg Ser Gly Pro Asn Ser Tyr Thr Leu Tyr Leu Asn Gly Ser
        610                 615                 620
Met Ile Ser Ile Ser Val Arg Pro Leu Thr Asp Gly Gly Leu Leu Val
625                 630                 635                 640
Leu Leu Asp Gly Lys Ala His Thr Thr Tyr Ser Leu Glu Glu Val Gln
                645                 650                 655
Ala Thr Arg Leu Met Val Asp Gly Lys Thr Cys Leu Leu Glu Lys Glu
                660                 665                 670
Asn Asp Pro Thr Gln Leu Arg Ser Pro Ser Pro Gly Lys Leu Val Arg
                675                 680                 685
Tyr Leu Val Glu Ser Gly Asp His Val Thr Ala Ser Gln Ala Tyr Ala
        690                 695                 700
Glu Ile Glu Val Met Lys Met Tyr Met Pro Leu Ile Ala Thr Glu Asp
705                 710                 715                 720
Gly Ile Val Gln Phe Ile Lys Gln Pro Gly Thr Thr Leu Asp Ala Gly
                725                 730                 735
Asp Ile Ile Gly Ile Leu Ser Leu Asp Asp Pro Ser Arg Val Arg His
                740                 745                 750
Ala Lys Pro Phe Glu Gly Gln Leu Pro Pro Met Gly Gln Pro Thr Ile
        755                 760                 765
His Gly Ala Lys Pro His Gln Arg Tyr Arg Glu Leu Arg Leu Val Leu
        770                 775                 780
Asp Asn Ala Met Asp Gly Tyr Asp Asn Gln Ala Leu Val Gln Pro Thr
785                 790                 795                 800
Leu Lys Glu Ile Phe Glu Val Leu Gln Thr Pro Glu Leu Pro Tyr Leu
                805                 810                 815
Glu Phe Asn Glu Val Phe Ala Ser Leu Ser Gly Arg Ile Pro Pro Lys
                820                 825                 830
Leu Glu Ile Ala Leu His Gln Glu Val Asp Gln Ser Met Lys Asn His
        835                 840                 845
Glu His Phe Pro Ala Arg Thr Leu Gln Ala Leu Ile Asp Ser His Cys
        850                 855                 860
Arg Ala Asn Phe Ser Lys Ala Ala Asp Ile Asn Ala Phe Gln Ala Ser
865                 870                 875                 880
Val Gly Pro Leu Thr Ala Ile Ile Lys Glu Tyr Gln His Gly Leu Lys
                885                 890                 895
Thr His Ser Trp Gly Phe Ile Ala Asp Tyr Leu Asn Lys Tyr His Glu
                900                 905                 910
Val Glu Ser Leu Phe Asp Asp Ser Ala Arg Glu Glu Ile Phe Leu
        915                 920                 925
Ser Leu Arg Asp Gln Asn Lys Asp Asp Val Glu Lys Val Ile Arg Ile
        930                 935                 940
Ala Leu Ser His Ser Arg Val Thr Ala Lys Asn Asn Leu Val Leu Thr
945                 950                 955                 960
Leu Leu Asp Gln Ile Lys Pro Thr Ala Ser Gly Gly Ala Leu Asp Lys
                965                 970                 975
Phe Phe Ser Pro Val Leu Lys Lys Leu Ala Glu Leu Thr Gly Arg Leu
                980                 985                 990
Thr Ala Lys Val Ser Leu Lys Ala  Arg Glu Leu Leu Ile  His Val Gln
        995                 1000                1005
```

-continued

```
Leu Pro Ser Phe Glu Glu Arg Gln Ser Gln Met Glu Lys Ile Leu
    1010                1015                1020

Arg Ser Ser Val Thr Glu Glu Val Tyr Gly Gly Glu His Glu Ala
    1025                1030                1035

Arg Met Pro Ala Phe Glu Asn Ile Lys Glu Leu Val Asp Thr Thr
    1040                1045                1050

Tyr Thr Val Phe Asp Val Leu Pro Asn Phe Phe Tyr His Glu Ser
    1055                1060                1065

Leu His Val Arg Ile Ala Ala Phe Glu Val Tyr Cys Arg Arg Ala
    1070                1075                1080

Tyr His Ala Tyr Glu Ile Leu Asp Ile Asn Tyr His Met Glu His
    1085                1090                1095

Gln Pro Leu Leu Ile Thr Trp Lys Phe Leu Leu Asn Thr Pro Asn
    1100                1105                1110

Lys Ser Glu Ser Gly Pro Asn Arg Val Ala Ser Val Ser Asp Met
    1115                1120                1125

Ser Tyr Leu Ile Asn Lys Ala Asp Pro Glu Pro Val Arg Thr Gly
    1130                1135                1140

Ala Ile Leu Ala Val Arg Asp Val Lys Glu Leu Glu Asp Arg Phe
    1145                1150                1155

Glu Ser Ile Leu Asn Phe Phe Pro Ser His Lys Ser Asn Lys His
    1160                1165                1170

Leu Ser His Leu Ala Ala Ala Ser Val His Asn Asn Val Leu Asn
    1175                1180                1185

Val Val Ile Lys Ser Glu Ser Val His Pro Asn Asp Asp Asp Tyr
    1190                1195                1200

Trp Leu Asn Leu Leu Ser Pro Ile Val Lys Gly Glu Thr Glu Arg
    1205                1210                1215

Leu Arg Ser His Gly Ile Arg Arg Met Thr Phe Leu Ile Phe Arg
    1220                1225                1230

Gln Gly Asn Tyr Pro Ser Tyr Phe Thr Phe Arg Glu Arg Asn Asn
    1235                1240                1245

Tyr Ala Glu Asp Gln Thr Ile Arg His Ile Glu Pro Ala Met Ala
    1250                1255                1260

Tyr Arg Leu Glu Leu Ala Arg Leu Ser Asn Phe Asp Ile Lys Pro
    1265                1270                1275

Cys Phe Ile Asp Asn Arg Gln Val His Val Tyr Tyr Ala Val Gly
    1280                1285                1290

Lys Glu Asn Ile Ser Asp Cys Arg Phe Phe Val Cys Ala Leu Val
    1295                1300                1305

Arg Pro Gly Arg Leu Arg Ser Ser Val Arg Thr Ala Asp Tyr Leu
    1310                1315                1320

Ile Ser Glu Thr Asp Arg Leu Leu Asn Asp Ile Leu Asp Ala Leu
    1325                1330                1335

Glu Ile Val Gly Ala Thr Tyr Lys Gln Ser Asp Cys Asn His Leu
    1340                1345                1350

Phe Ile Asn Phe Ile Pro Thr Phe Gln Leu Asp Ala Thr Glu Val
    1355                1360                1365

Glu Thr Ala Leu Lys Gly Phe Ile Asp Arg His Gly Lys Arg Leu
    1370                1375                1380

Trp Arg Leu Arg Val Thr Gly Ala Glu Ile Arg Phe Asn Val Gln
    1385                1390                1395

Ser Lys Ser Ala Asn Gly Val Glu Ala Asp Pro Val Pro Leu Arg
```

-continued

```
            1400                1405                1410
Phe Ile Ile Ser Asn Val Ser Gly Tyr Val Leu Asn Val Asp Thr
        1415                1420                1425
Tyr Arg Glu Val Gln Thr Glu Lys Gly Ala Ile Phe Lys Ser Val
        1430                1435                1440
Gly Pro Thr Gly Pro Phe His Leu Leu Pro Val Asn Gln Pro Tyr
        1445                1450                1455
Pro Thr Lys Glu Trp Leu Gln Pro Arg Arg Tyr Lys Ala His Leu
        1460                1465                1470
Met Gly Thr Thr Tyr Val Tyr Asp Phe Gly Leu Phe Arg Gln
        1475                1480                1485
Ala Val Arg Ala Gln Trp Asn His Ala Ile Lys Gln Asn Ser Ser
        1490                1495                1500
Leu Lys Val Pro Ser Gln Val Leu Glu Met Arg Glu Leu Val Leu
        1505                1510                1515
Asp Glu Arg Gln Gln Leu Gln Gln Val Val Arg Asp Ala Gly Ser
        1520                1525                1530
Asn Asn Cys Gly Met Val Ala Trp Ile Phe Thr Leu Arg Thr Pro
        1535                1540                1545
Glu Tyr Pro Glu Gly Arg Gln Ile Ile Val Ile Ala Asn Asp Ile
        1550                1555                1560
Thr Phe Asn Ile Gly Ser Phe Gly Pro Glu Glu Asp Leu Val Phe
        1565                1570                1575
Tyr Lys Ala Ser Glu Met Ala Arg Lys Leu Gly Ile Pro Arg Val
        1580                1585                1590
Tyr Leu Ser Ala Asn Ser Gly Ala Arg Ile Gly Leu Ala Ser Glu
        1595                1600                1605
Val Ile Gly Leu Phe Asn Ser Cys Trp Asn Asp Ala Ser Asn Pro
        1610                1615                1620
Ser Lys Gly Phe Lys Tyr Ile Tyr Leu Thr Asp Ala Gly Leu Lys
        1625                1630                1635
Gln Leu Glu Ala Gln Glu Glu Arg Ser Gly Lys Lys Ser Val Ile
        1640                1645                1650
Thr Glu Thr Ile Val Glu Asp Gly Glu Thr Arg His Lys Ile Thr
        1655                1660                1665
Asp Val Ile Gly Ala Val Asp Gly Leu Gly Val Glu Asn Leu Arg
        1670                1675                1680
Gly Ser Gly Leu Ile Ala Gly Glu Thr Ser Arg Ala Tyr Asp Asp
        1685                1690                1695
Ile Phe Thr Ile Thr Leu Val Thr Cys Arg Ser Val Gly Ile Gly
        1700                1705                1710
Ala Tyr Leu Val Arg Leu Gly Gln Arg Thr Ile Gln Asn Glu Gly
        1715                1720                1725
Gln Pro Ile Ile Leu Thr Gly Ala Pro Ala Leu Asn Lys Leu Leu
        1730                1735                1740
Gly Arg Asp Val Tyr Thr Ser Asn Leu Gln Leu Gly Gly Thr Gln
        1745                1750                1755
Ile Met Tyr Lys Asn Gly Val Ser His Leu Thr Ala Gln Asn Asp
        1760                1765                1770
Tyr Glu Gly Ile Gly Lys Ile Val Asn Trp Leu Ser Tyr Ile Pro
        1775                1780                1785
Glu Arg Lys Asn Ala Pro Val Pro Ile Thr Val Ser Asn Asp Thr
        1790                1795                1800
```

```
Trp Asp Arg Asp Ile Asp Tyr Leu Pro Pro Lys Gly Ala Val Tyr
1805                1810                1815

Asp Pro Arg Trp Leu Ile Ala Gly Lys Glu Ala Glu Glu Glu Gly
1820                1825                1830

Ala Ser Phe Gln Thr Gly Phe Phe Asp Lys Asp Ser Phe Thr Glu
1835                1840                1845

Thr Leu Thr Gly Trp Ala Arg Thr Val Val Gly Arg Ala Arg
1850                1855                1860

Leu Gly Gly Val Pro Met Gly Val Ile Ala Val Glu Thr Arg Ser
1865                1870                1875

Val Glu His Ile Ile Pro Ala Asp Pro Ala Asn Gly Asp Ser Val
1880                1885                1890

Glu Gln Val Leu Met Glu Ala Gly Asn Val Trp Tyr Pro Asn Ser
1895                1900                1905

Ala Tyr Lys Thr Ala Gln Ala Ile Asn Asp Phe Asn Lys Gly Glu
1910                1915                1920

Gln Leu Pro Leu Met Ile Phe Ala Asn Trp Arg Gly Phe Ser Gly
1925                1930                1935

Gly Gln Arg Asp Met Tyr Asn Glu Ile Leu Lys Tyr Gly Ser Phe
1940                1945                1950

Ile Val Asp Ala Leu Ser Ser Tyr Lys Gln Pro Val Phe Val Tyr
1955                1960                1965

Val Val Pro Asn Gly Glu Leu Arg Gly Gly Ala Trp Val Val Val
1970                1975                1980

Asp Pro Thr Ile Asn Glu Asp Met Met Glu Met Tyr Ala Asp Lys
1985                1990                1995

Arg Ser Arg Ala Gly Val Leu Glu Pro Glu Gly Ile Val Glu Ile
2000                2005                2010

Lys Phe Arg Lys Ala Gln Leu Leu Ala Thr Met Glu Arg Leu Asp
2015                2020                2025

Asp Lys Tyr Arg Ala Leu Lys Ala Gln Tyr Glu Asn Pro Ala Leu
2030                2035                2040

Val Gly Thr Glu Arg Glu Glu Ile Lys Thr Lys Leu Thr Glu Arg
2045                2050                2055

Glu Gln Glu Leu Leu Pro Val Tyr Gln Gln Leu Ala Ile Gln Phe
2060                2065                2070

Ala Asp Leu His Asp Thr Ala Gly Arg Met Lys Ala Lys Gly Thr
2075                2080                2085

Ile Arg Glu Ala Leu Asp Trp Thr Asn Ala Arg Arg Tyr Phe Tyr
2090                2095                2100

Trp Arg Val Arg Arg Arg Leu Ala Glu Glu Tyr Ile Arg Arg Lys
2105                2110                2115

Met Ala Ile Ala Asn Lys Asp Leu Ser Arg Glu Glu Gln Thr Lys
2120                2125                2130

Ser Leu Leu Ser Trp Phe Gly Arg Asp Thr Val His Ser Ser Glu
2135                2140                2145

Ser Glu Leu Glu Gln Ile Trp Glu Ser Asp Asp Arg Val Val Leu
2150                2155                2160

Glu Trp Phe Glu Gly His Glu Ser Lys Val Thr Gly Leu Ile Gln
2165                2170                2175

Glu Leu Asn Asn Ala Ala Thr Ala Ser Glu Val Leu Arg Met Tyr
2180                2185                2190
```

```
Thr Ser  Asn Arg Ala Gly Val  Val Glu Gly Phe Asp  Arg Ile Leu
    2195             2200             2205

Gln Ser  Leu Ser Asp Gln Glu  Lys Gln Asp Ile Leu  Ala Lys Phe
    2210             2215             2220

Ala Thr  Met Thr Val
    2225

<210> SEQ ID NO 3
<211> LENGTH: 6687
<212> TYPE: DNA
<213> ORGANISM: Mortierella alpina

<400> SEQUENCE: 3
atgactacca acgtacagtc cttcattgga ggaaacgcat tagagaacgc ccctgctgga      60
gctgtccgcg agtttgttaa ccagcatgga ggccacagcg tgatcaccaa gatcctgatc     120
gccaacaacg gtattgcggc cgtcaaggag atccgatctg tccgcaagtg ggcgtacgag     180
acctttggag atgagcgtgc gatccagttc acggtcatgg ctacgccaga ggatctgaag     240
atcaatgctg aatatatccg catggccgac cagtatgtcg aagtaccggg aggatccaac     300
aacaacaact acgccaacgt tgacctcatt gtcgacattg ccgaacgcac cggcgtccat     360
gctgtgtggg ctggatgggg acatgcctcg gagaacccca actcccaga gtctcttcgc     420 gacagccctc aaaagatcat cttcatcgga ccccccggct ccgccatgcg ctcgttgggt     480
gacaagatct cgtccacgat cgtcgctcaa tcggccgacg tccctacgat gggctggtcc     540
ggaactggca tcacagagac taccatggat gctaatggtt cgtcatggt gcccgaggat     600 gcttaccagg ctgcctgtgt caccgatgca gaggatggtc ttcagaaggc ccacaccatc     660 ggcttccccgg tcatgatcaa ggcttcagag ggtggtggag aaagggtat tcgtaaggtt     720 gaggaaccag aaaagttcgc tcaggccttc aaccaggttt gggcgaggt ccccggttcc     780 cccgtcttca tcatgaagtt ggctggtaac gcgcgccatc tggaggtcca gcttttggcc     840
gatcagtatg gaaatgccat ctcgctcttt ggacgcgatt gctctgtcca cgtcgccat     900 cagaagatta ttgaggaagc tcccgtcacc attgccaagc ccgacacctt cgagtcgatg     960
gagaaggctg cagtgcgtct ggccaagttg gtcggatacg tttctgcagg taccgtcgag    1020
tacctgtact cgcactcgac tgacaccttc ttcttcctgg agttgaaccc cagacttcag    1080
gtcgagcatc ctaccaccga tggtctca ggtgtcaacc tgccagctgc tcagctccag    1140
atcgccatgg gtcttccttt gaaccgcatc aaggacatcc gtgttctcta tggtcttcaa    1200
cccacaggaa cgtccgagat cgactttgag ttttcacagc agatctcgta tgagactcag    1260
cgcaagcccg cccctaaggg acacgtcatt gctgtccgta tcacagccga aaccccgat    1320 gcaggattca agccctcaag cggaatgatg caggaactca atttcagatc atctaccaac    1380
gtctggggct acttctctgt caactctgca ggaggactgc acgagtttgc cgattctcag    1440
tttggtcata tctttgccta tggacaggat cgtggtcagt ctagaaagaa catggtcgtt    1500
gccctcaagg aactctccat tcgtggtgat ttccgcacta cggtcgagta cttgatccgc    1560
cttttggaga cacaggagtt cgaggaaaac accattaaca ctggctggct cgacagcttg    1620
atctccaaca acctcactgc tgaacgccct gagaccatgt tggctgtcat gtgtggtgct    1680
gttaacagag cccacaccat ctccgagaac tgcattaagg agtacaagaa gtcgctggag    1740
aagggtcaag tgcctagcaa ggacgttctg cgctcggtca accagcttga ctttatttac    1800
gacggcgtcc gctacaactt caccgccact cgctctggac ccaactcgta cactctgtac    1860
```

```
ttgaatggat ccatgatctc catctctgtg cgtccattga ccgatggcgg tctcttggtc    1920
cttttggatg gcaaggctca cacgacttac tcgttggaag aggtccaggc cactcgcctg    1980
atggtcgatg gaaagacttg tttgttggag aaggagaacg accctactca actccgctcc    2040
ccctccccag gcaaacttgt tcgctacctt gtcgagtctg cgaccatgt tacggccagc     2100
caggcctatg ctgagattga ggtcatgaag atgtatatgc ccttgatcgc caccgaggac    2160
ggtattgtgc agttcatcaa gcaacccggc accactctgg atgctggtga tatcattggt    2220
atcctcagct tggacgatcc ctcccgcgtt cgccacgcta agcccttcga aggtcagctc    2280
cctcccatgg gtcagcccac cattcacgga gctaagcccc atcagcgtta ccgcgagctg    2340
cgactcgtcc tcgacaatgc catggatggc tacgataacc aggctttggt ccagcctacg    2400
ctgaaggaga tctttgaggt cctccagacc ccggagctgc cctacttgga attcaacgag    2460
gtctttgctt cgctaagcgg aagaatccca cccaagctgg aaattgccct gcaccaggag    2520
gtggatcagt ccatgaagaa ccacgagcac ttccccgctc gtactcttca ggccctgatt    2580
gactcgcact gccgcgccaa cttctccaag gccgccgata tcaatgcgtt ccaagcctcg    2640
gtgggacctc tgaccgccat catcaaggag taccaacacg gtttgaaaac tcactcctgg    2700
ggcttcattg ctgattacct caacaagtac catgaagtcg agtcgctctt tgatgactct    2760
gctcgtgagg aagagatctt cctgtccctg cgtgatcaga acaaggacga cgtcgagaag    2820
gtcatccgca tcgcactctc gcactcgcgt gtcactgcca gaacaacttt ggttttgacc    2880
cttcttgacc agatcaaacc tacggcctct ggaggagcgc tcgacaagtt cttctcgcct    2940
gtgctcaaga agctggctga gcttactggc cgtctcaccg ccaaggtctc gctcaaggcc    3000
agagagctcc ttattcatgt tcagttgccc agctttgagg aacgccagtc gcagatggag    3060
aagatcctcc gctcgagcgt cactgaggag gtttatggtg gtgaacacga ggcccgcatg    3120
cctgcctttg agaacatcaa ggagttggtc gacaccacct acacagtctt tgatgtcttg    3180
cctaacttct tttaccatga gtcgttgcat gtccgcattg ccgcgttcga ggtgtactgc    3240
cgtcgtgcct accatgcgta cgagattttg gacatcaatt accacatgga gcaccagccc    3300
ttgctgatca cttggaagtt cttgctcaac accccccaaca gtccgagtc tggtcccaac    3360
cgtgtggcta gtgtcagtga catgagttac ttgatcaaca aggctgaccc tgagcctgtt    3420
cgtaccggtg ccattcttgc cgttcgcgac gtgaaggagc tggaggacag attcgagagc    3480
atcctcaact tcttcccctc tcacaagtcg aacaagcact tgagccatct cgctgccgcc    3540
agcgtccaca caatgtgtt gaacgttgtc atcaagtccg agtcggttca ccccaacgat    3600
gatgactact ggctgaacct cctcagcccc atcgtgaagg gcgagaccga gcgccttcgc    3660
tcgcacggca tccgtcgcat gaccttcttg atcttccgtc agggcaacta cccctcgtac    3720
ttcaccttcc gtgagcgtaa caactacgct gaggatcaga ccatccgtca catcgagccc    3780
gccatggcat accgtcttga gttggcgcgc ttgtccaact tgacatcaa gccctgcttc    3840
attgacaatc gccaggttca tgtgtactat gctgtgggca aggagaacat ttcggactgc    3900
cgcttctttg tctgcgcctt ggttcgtcct ggtcgcctgc gctctagcgt tcgtacggcg    3960
gattacttga tttcggagac cgaccgtctg ttgaacgata ttctggatgc tctggagatt    4020
gtgggtgcca cctacaagca gagtgactgc aaccacttgt ttatcaactt catccccact    4080
ttccagttgg acgctaccga ggttgagact gccctcaagg gattcattga ccgcacggc    4140
aagcgtctct ggcgtcttcg cgtcactggc gctgagattc gcttcaatgt tcagtccaag    4200
tctgcgaatg gcgttgaggc cgaccccgtt cctcttcgat tcatcatctc caacgtctct    4260
```

```
ggatatgtct tgaacgtcga cacctaccgc gaggttcaga ccgagaaggg tgccatcttc    4320
aagtcggttg gtcctaccgg tcccttccat ctcttgcctg tgaaccagcc ctaccccaca    4380
aaggagtggc ttcagcccag acgttacaag gcacacttga tgggcacgac ttacgtctat    4440
gactttggcg agctcttccg ccaggccgtc cgtgctcagt ggaaccatgc catcaagcag    4500
aactcttcgc tcaaggtccc atcccaggtc ttggagatgc gcgagctggt cttggatgag    4560
agacagcagt tgcagcaggt cgttcgcgat gccggttcca acaactgcgg catggttgcc    4620
tggattttca ctctccgtac ccccgagtac cccgagggtc gacagatcat tgtcattgcc    4680
aacgatatca ccttcaacat tggatcgttt ggacccgagg aggacctggt cttctacaag    4740
gcgtccgaga tggccagaaa gttgggcatt ccccgtgttt acctctctgc caactctggt    4800
gcccgcattg gtcttgctag tgaagtgatt ggtctcttca actcttgctg gaacgacgct    4860
tccaacccct ccaagggctt caagtacatc tacctcacgg acgctggact gaagcagttg    4920
gaggctcagg aggagcgctc tggtaagaag agcgtcatca cagagaccat tgttgaggat    4980
ggcgagaccc gccataagat cacggatgtc atcggtgctg tcgacggtct tggtgttgag    5040
aacttgcgcg gaagtggtct gattgctgga gagacctcgc gagcctacga cgacatctt    5100 accattactt tggtcacctg ccgctctgtt ggtatcggtg cgtacttggt tcgtttgggt    5160
cagcgtacta ttcagaatga gggccagccc atcattttga ctggtgcccc tgccctcaac    5220
aagttgcttg gtcgcgatgt ctacacctcg aacttgcagc tcggaggcac tcagattatg    5280
tacaagaacg gagtgtcgca cttgaccgct cagaacgact atgagggtat tggcaagatc    5340
gtcaactggc tctcgtacat tcctgagcgc aagaatgcac cggtgcccat cacggtcagc    5400
aacgacacct gggaccgcga catcgactac ttgcctccca agggtgcagt ctatgatccc    5460
cgctggttga tcgctggtaa ggaggctgag gaggagggcg cctctttcca gactggtttc    5520
ttcgacaagg attcgtttac cgagacattg acgggctggg cccgcacggt tgttgttgga    5580
cgtgcccgtc tcggtggtgt ccctatggga gtgattgcag ttgagacccg ctcggtcgag    5640
cacatcatcc ctgctgatcc cgccaacggc gactctgtcg agcaggtctt gatggaggct    5700
ggaaatgttt ggtaccccaa ctcggcttac aagactgcgc aggccatcaa cgacttcaac    5760
aagggagagc agcttccact gatgatcttt gccaactggc gtggattctc gggtggtcag    5820
cgcgacatgt acaatgagat cctcaagtac ggttccttca ttgtcgatgc tctgagctca    5880
tacaagcagc ctgtgtttgt ctatgtggtt cccaacggag agcttcgtgg aggtgcttgg    5940
gtcgtcgttg accctactat caacgaggac atgatggaga tgtatgctga caagcggtca    6000
agagccggtg tcttggagcc tgagggtatt gttgagatca agttccgtaa ggcccagttg    6060
ttggcgacca tggagcgttt ggacgacaag taccgcgcat tgaaggccca gtacgagaac    6120
ccagccttgg ttggtaccga gcgcgaggag atcaagacga agctgacgga gcgcgagcaa    6180
gagctgttgc ctgtgtacca gcagctggcg atccaattcg cggatctgca cgacactgcg    6240
ggacgcatga aggccaaggg cacgattcgt gaagccttgg actggaccaa tgcccgtcgc    6300
tacttctact ggcgcgtgcg cagaagattg gctgaggagt acattcgtcg caagatggct    6360
attgccaaca aggacttgag ccgtgaggag cagaccaagt cgctgctgtc ttggttcggc    6420
cgtgacacgg tgcactcgag cgagagcgag ctggagcaga tctgggaatc tgacgatcgc    6480
gtggtgttgg agtggttcga gggacacgag agcaaggtga ctggattgat ccaggagctg    6540
aacaatgcgg cgactgccag cgaggtgctg agaatgtaca cctccaaccg cgctggtgtg    6600
```

-continued

```
gtcgagggct tcgatcgtat ccttcagagc ctgtcggacc aggagaagca ggacatcctt      6660
gccaagttcg ccacgatgac cgtttaa                                          6687

<210> SEQ ID NO 4
<211> LENGTH: 6865
<212> TYPE: DNA
<213> ORGANISM: Mortierella alpina
<220> FEATURE:
<221> NAME/KEY: CDS
<222> LOCATION: (45)..(6728)
<220> FEATURE:
<221> NAME/KEY: modified_base
<222> LOCATION: (6745)..(6746)
<223> OTHER INFORMATION: a, c, t, g, unknown or other

<400> SEQUENCE: 4
tcccactgac tcaagcggaa cttccaagca accataatcc catc atg act acc aac        56
                                                Met Thr Thr Asn
                                                  1 gta cag tcc ttc att gga gga aac gca tta gag aac gcc cct gct gga        104
Val Gln Ser Phe Ile Gly Gly Asn Ala Leu Glu Asn Ala Pro Ala Gly
  5                  10                  15                  20 gct gtc cgc gag ttt gtt aac cag cat gga ggc cac agc gtg atc acc        152
Ala Val Arg Glu Phe Val Asn Gln His Gly Gly His Ser Val Ile Thr
             25                  30                  35 aag atc ctg atc gcc aac aac ggt att gcg gcc gtc aag gag atc cga        200
Lys Ile Leu Ile Ala Asn Asn Gly Ile Ala Ala Val Lys Glu Ile Arg
         40                  45                  50 tct gtc cgc aag tgg gcg tac gag acc ttt gga gat gag cgt gcg atc        248
Ser Val Arg Lys Trp Ala Tyr Glu Thr Phe Gly Asp Glu Arg Ala Ile
     55                  60                  65 cag ttc acg gtc atg gct acg cca gag gat ctg aag atc aat gct gaa        296
Gln Phe Thr Val Met Ala Thr Pro Glu Asp Leu Lys Ile Asn Ala Glu
 70                  75                  80 tat atc cgc atg gcc gac cag tat gtc gaa gta ccg gga gga tcc aac        344
Tyr Ile Arg Met Ala Asp Gln Tyr Val Glu Val Pro Gly Gly Ser Asn
 85                  90                  95                 100 aac aac aac tac gcc aac gtt gac ctc att gtc gac att gcc gaa cgc        392
Asn Asn Asn Tyr Ala Asn Val Asp Leu Ile Val Asp Ile Ala Glu Arg
                105                 110                 115 acc ggc gtc cat gct gtg tgg gct gga tgg gga cat gcc tcg gag aac        440
Thr Gly Val His Ala Val Trp Ala Gly Trp Gly His Ala Ser Glu Asn
            120                 125                 130 ccc aaa ctc cca gag tct ctt cgc gac agc cct caa aag atc atc ttc        488
Pro Lys Leu Pro Glu Ser Leu Arg Asp Ser Pro Gln Lys Ile Ile Phe
        135                 140                 145 atc gga ccc ccc ggc tcc gcc atg cgc tcg ttg ggt gac aag atc tcg        536
Ile Gly Pro Pro Gly Ser Ala Met Arg Ser Leu Gly Asp Lys Ile Ser
    150                 155                 160 tcc acg atc gtc gct caa tcg gcc gac gtc cct acg atg ggc tgg tcc        584
Ser Thr Ile Val Ala Gln Ser Ala Asp Val Pro Thr Met Gly Trp Ser
165                 170                 175                 180 gga act ggc atc aca gag act acc atg gat gct aat ggt ttc gtc atg        632
Gly Thr Gly Ile Thr Glu Thr Thr Met Asp Ala Asn Gly Phe Val Met
                185                 190                 195 gtg ccc gag gat gct tac cag gct gcc tgt gtc acc gat gca gag gat        680
Val Pro Glu Asp Ala Tyr Gln Ala Ala Cys Val Thr Asp Ala Glu Asp
            200                 205                 210 ggt ctt cag aag gcc cac acc atc ggc ttc ccg gtc atg atc aag gct        728
Gly Leu Gln Lys Ala His Thr Ile Gly Phe Pro Val Met Ile Lys Ala
        215                 220                 225
```

-continued

| | | | | | | | | | | | | | | | | |
|---|---|---|---|---|---|---|---|---|---|---|---|---|---|---|---|---|
| tca | gag | ggt | ggt | gga | gga | aag | ggt | att | cgt | aag | gtt | gag | gaa | cca | gaa | 776 |
| Ser | Glu | Gly | Gly | Gly | Gly | Lys | Gly | Ile | Arg | Lys | Val | Glu | Glu | Pro | Glu | |
| 230 | | | | | 235 | | | | | 240 | | | | | | |
| aag | ttc | gct | cag | gcc | ttc | aac | cag | gtt | ttg | ggc | gag | gtc | ccc | ggt | tcc | 824 |
| Lys | Phe | Ala | Gln | Ala | Phe | Asn | Gln | Val | Leu | Gly | Glu | Val | Pro | Gly | Ser | |
| 245 | | | | | 250 | | | | | 255 | | | | | 260 | |
| ccc | gtc | ttc | atc | atg | aag | ttg | gct | ggt | aac | gcg | cgc | cat | ctg | gag | gtc | 872 |
| Pro | Val | Phe | Ile | Met | Lys | Leu | Ala | Gly | Asn | Ala | Arg | His | Leu | Glu | Val | |
| | | | | 265 | | | | | 270 | | | | | 275 | | |
| cag | ctt | ttg | gcc | gat | cag | tat | gga | aat | gcc | atc | tcg | ctc | ttt | gga | cgc | 920 |
| Gln | Leu | Leu | Ala | Asp | Gln | Tyr | Gly | Asn | Ala | Ile | Ser | Leu | Phe | Gly | Arg | |
| | | | 280 | | | | | 285 | | | | | 290 | | | |
| gat | tgc | tct | gtc | cag | cgt | cgc | cat | cag | aag | att | att | gag | gaa | gct | ccc | 968 |
| Asp | Cys | Ser | Val | Gln | Arg | Arg | His | Gln | Lys | Ile | Ile | Glu | Glu | Ala | Pro | |
| | | 295 | | | | | 300 | | | | | 305 | | | | |
| gtc | acc | att | gcc | aag | ccc | gac | acc | ttc | gag | tcg | atg | gag | aag | gct | gca | 1016 |
| Val | Thr | Ile | Ala | Lys | Pro | Asp | Thr | Phe | Glu | Ser | Met | Glu | Lys | Ala | Ala | |
| | 310 | | | | | 315 | | | | | 320 | | | | | |
| gtg | cgt | ctg | gcc | aag | ttg | gtc | gga | tac | gtt | tct | gca | ggt | acc | gtc | gag | 1064 |
| Val | Arg | Leu | Ala | Lys | Leu | Val | Gly | Tyr | Val | Ser | Ala | Gly | Thr | Val | Glu | |
| 325 | | | | | 330 | | | | | 335 | | | | | 340 | |
| tac | ctg | tac | tcg | cac | tcg | act | gac | acc | ttc | ttc | ttc | ctg | gag | ttg | aac | 1112 |
| Tyr | Leu | Tyr | Ser | His | Ser | Thr | Asp | Thr | Phe | Phe | Phe | Leu | Glu | Leu | Asn | |
| | | | | 345 | | | | | 350 | | | | | 355 | | |
| ccc | aga | ctt | cag | gtc | gag | cat | cct | acc | acc | gag | atg | gtc | tca | ggt | gtc | 1160 |
| Pro | Arg | Leu | Gln | Val | Glu | His | Pro | Thr | Thr | Glu | Met | Val | Ser | Gly | Val | |
| | | | 360 | | | | | 365 | | | | | 370 | | | |
| aac | ctg | cca | gct | gct | cag | ctc | cag | atc | gcc | atg | ggt | ctt | cct | ttg | aac | 1208 |
| Asn | Leu | Pro | Ala | Ala | Gln | Leu | Gln | Ile | Ala | Met | Gly | Leu | Pro | Leu | Asn | |
| | | 375 | | | | | 380 | | | | | 385 | | | | |
| cgc | atc | aag | gac | atc | cgt | gtt | ctc | tat | ggt | ctt | caa | ccc | aca | gga | acg | 1256 |
| Arg | Ile | Lys | Asp | Ile | Arg | Val | Leu | Tyr | Gly | Leu | Gln | Pro | Thr | Gly | Thr | |
| | 390 | | | | | 395 | | | | | 400 | | | | | |
| tcc | gag | atc | gac | ttt | gag | ttt | tca | cag | cag | atc | tcg | tat | gag | act | cag | 1304 |
| Ser | Glu | Ile | Asp | Phe | Glu | Phe | Ser | Gln | Gln | Ile | Ser | Tyr | Glu | Thr | Gln | |
| 405 | | | | | 410 | | | | | 415 | | | | | 420 | |
| cgc | aag | ccc | gcc | cct | aag | gga | cac | gtc | att | gct | gtc | cgt | atc | aca | gcc | 1352 |
| Arg | Lys | Pro | Ala | Pro | Lys | Gly | His | Val | Ile | Ala | Val | Arg | Ile | Thr | Ala | |
| | | | | 425 | | | | | 430 | | | | | 435 | | |
| gag | aac | ccc | gat | gca | gga | ttc | aag | ccc | tca | agc | gga | atg | atg | cag | gaa | 1400 |
| Glu | Asn | Pro | Asp | Ala | Gly | Phe | Lys | Pro | Ser | Ser | Gly | Met | Met | Gln | Glu | |
| | | | 440 | | | | | 445 | | | | | 450 | | | |
| ctc | aat | ttc | aga | tca | tct | acc | aac | gtc | tgg | ggc | tac | ttc | tct | gtc | aac | 1448 |
| Leu | Asn | Phe | Arg | Ser | Ser | Thr | Asn | Val | Trp | Gly | Tyr | Phe | Ser | Val | Asn | |
| | | 455 | | | | | 460 | | | | | 465 | | | | |
| tct | gca | gga | gga | ctg | cac | gag | ttt | gcc | gat | tct | cag | ttt | ggt | cat | atc | 1496 |
| Ser | Ala | Gly | Gly | Leu | His | Glu | Phe | Ala | Asp | Ser | Gln | Phe | Gly | His | Ile | |
| | 470 | | | | | 475 | | | | | 480 | | | | | |
| ttt | gcc | tat | gga | cag | gat | cgt | ggt | cag | tct | aga | aag | aac | atg | gtc | gtt | 1544 |
| Phe | Ala | Tyr | Gly | Gln | Asp | Arg | Gly | Gln | Ser | Arg | Lys | Asn | Met | Val | Val | |
| 485 | | | | | 490 | | | | | 495 | | | | | 500 | |
| gcc | ctc | aag | gaa | ctc | tcc | att | cgt | ggt | gat | ttc | cgc | act | acg | gtc | gag | 1592 |
| Ala | Leu | Lys | Glu | Leu | Ser | Ile | Arg | Gly | Asp | Phe | Arg | Thr | Thr | Val | Glu | |
| | | | | 505 | | | | | 510 | | | | | 515 | | |
| tac | ttg | atc | cgc | ctt | ttg | gag | aca | cag | gag | ttc | gag | gaa | aac | acc | att | 1640 |
| Tyr | Leu | Ile | Arg | Leu | Leu | Glu | Thr | Gln | Glu | Phe | Glu | Glu | Asn | Thr | Ile | |
| | | | 520 | | | | | 525 | | | | | 530 | | | |
| aac | act | ggc | tgg | ctc | gac | agc | ttg | atc | tcc | aac | aac | ctc | act | gct | gaa | 1688 |
| Asn | Thr | Gly | Trp | Leu | Asp | Ser | Leu | Ile | Ser | Asn | Asn | Leu | Thr | Ala | Glu | |
| | | 535 | | | | | 540 | | | | | 545 | | | | |

-continued

| | | |
|---|---|---|
| cgc cct gag acc atg ttg gct gtc atg tgt ggt gct gtt aac aga gcc<br>Arg Pro Glu Thr Met Leu Ala Val Met Cys Gly Ala Val Asn Arg Ala<br>550                                            555                                 560 | 1736 |

```
cgc cct gag acc atg ttg gct gtc atg tgt ggt gct gtt aac aga gcc    1736
Arg Pro Glu Thr Met Leu Ala Val Met Cys Gly Ala Val Asn Arg Ala
550                 555                 560 cac acc atc tcc gag aac tgc att aag gag tac aag aag tcg ctg gag    1784
His Thr Ile Ser Glu Asn Cys Ile Lys Glu Tyr Lys Lys Ser Leu Glu
565                 570                 575                 580 aag ggt caa gtg cct agc aag gac gtt ctg cgc tcg gtc aac cag ctt    1832
Lys Gly Gln Val Pro Ser Lys Asp Val Leu Arg Ser Val Asn Gln Leu
            585                 590                 595 gac ttt att tac gac ggc gtc cgc tac aac ttc acc gcc act cgc tct    1880
Asp Phe Ile Tyr Asp Gly Val Arg Tyr Asn Phe Thr Ala Thr Arg Ser
600                 605                 610 gga ccc aac tcg tac act ctg tac ttg aat gga tcc atg atc tcc atc    1928
Gly Pro Asn Ser Tyr Thr Leu Tyr Leu Asn Gly Ser Met Ile Ser Ile
            615                 620                 625 tct gtg cgt cca ttg acc gat ggc ggt ctc ttg gtc ctt ttg gat ggc    1976
Ser Val Arg Pro Leu Thr Asp Gly Gly Leu Leu Val Leu Leu Asp Gly
630                 635                 640 aag gct cac acg act tac tcg ttg gaa gag gtc cag gcc act cgc ctg    2024
Lys Ala His Thr Thr Tyr Ser Leu Glu Glu Val Gln Ala Thr Arg Leu
645                 650                 655                 660 atg gtc gat gga aag act tgt ttg ttg gag aag gag aac gac cct act    2072
Met Val Asp Gly Lys Thr Cys Leu Leu Glu Lys Glu Asn Asp Pro Thr
            665                 670                 675 caa ctc cgc tcc ccc tcc cca ggc aaa ctt gtt cgc tac ctt gtc gag    2120
Gln Leu Arg Ser Pro Ser Pro Gly Lys Leu Val Arg Tyr Leu Val Glu
            680                 685                 690 tct ggc gac cat gtt acg gcc agc cag gcc tat gct gag att gag gtc    2168
Ser Gly Asp His Val Thr Ala Ser Gln Ala Tyr Ala Glu Ile Glu Val
            695                 700                 705 atg aag atg tat atg ccc ttg atc gcc acc gag gac ggt att gtg cag    2216
Met Lys Met Tyr Met Pro Leu Ile Ala Thr Glu Asp Gly Ile Val Gln
            710                 715                 720 ttc atc aag caa ccc ggc acc act ctg gat gct ggt gat atc att ggt    2264
Phe Ile Lys Gln Pro Gly Thr Thr Leu Asp Ala Gly Asp Ile Ile Gly
725                 730                 735                 740 atc ctc agc ttg gac gat ccc tcc cgc gtt cgc cac gct aag ccc ttc    2312
Ile Leu Ser Leu Asp Asp Pro Ser Arg Val Arg His Ala Lys Pro Phe
            745                 750                 755 gaa ggt cag ctc cct ccc atg ggt cag ccc acc att cac gga gct aag    2360
Glu Gly Gln Leu Pro Pro Met Gly Gln Pro Thr Ile His Gly Ala Lys
            760                 765                 770 ccc cat cag cgt tac cgc gag ctg cga ctc gtc ctc gac aat gcc atg    2408
Pro His Gln Arg Tyr Arg Glu Leu Arg Leu Val Leu Asp Asn Ala Met
            775                 780                 785 gat ggc tac gat aac cag gct ttg gtc cag cct acg ctg aag gag atc    2456
Asp Gly Tyr Asp Asn Gln Ala Leu Val Gln Pro Thr Leu Lys Glu Ile
            790                 795                 800 ttt gag gtc ctc cag acc ccg gag ctg ccc tac ttg gaa ttc aac gag    2504
Phe Glu Val Leu Gln Thr Pro Glu Leu Pro Tyr Leu Glu Phe Asn Glu
805                 810                 815                 820 gtc ttt gct tcg cta agc gga aga atc cca ccc aag ctg gaa att gcc    2552
Val Phe Ala Ser Leu Ser Gly Arg Ile Pro Pro Lys Leu Glu Ile Ala
            825                 830                 835 ctg cac cag gag gtg gat cag tcc atg aag aac cac gag cac ttc ccc    2600
Leu His Gln Glu Val Asp Gln Ser Met Lys Asn His Glu His Phe Pro
            840                 845                 850 gct cgt act ctt cag gcc ctg att gac tcg cac tgc cgc gcc aac ttc    2648
Ala Arg Thr Leu Gln Ala Leu Ile Asp Ser His Cys Arg Ala Asn Phe
```

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 855 |     |     |     |     | 860 |     |     |     |     | 865 |     |     |     |      |
| tcc | aag | gcc | gcc | gat | atc | aat | gcg | ttc | caa | gcc | tcg | gtg | gga | cct | ctg | 2696 |
| Ser | Lys | Ala | Ala | Asp | Ile | Asn | Ala | Phe | Gln | Ala | Ser | Val | Gly | Pro | Leu |      |
|     |     | 870 |     |     |     | 875 |     |     |     |     | 880 |     |     |     |     |      |
| acc | gcc | atc | atc | aag | gag | tac | caa | cac | ggt | ttg | aaa | act | cac | tcc | tgg | 2744 |
| Thr | Ala | Ile | Ile | Lys | Glu | Tyr | Gln | His | Gly | Leu | Lys | Thr | His | Ser | Trp |      |
| 885 |     |     |     |     | 890 |     |     |     |     | 895 |     |     |     |     | 900 |      |
| ggc | ttc | att | gct | gat | tac | ctc | aac | aag | tac | cat | gaa | gtc | gag | tcg | ctc | 2792 |
| Gly | Phe | Ile | Ala | Asp | Tyr | Leu | Asn | Lys | Tyr | His | Glu | Val | Glu | Ser | Leu |      |
|     |     |     |     | 905 |     |     |     |     | 910 |     |     |     |     | 915 |     |      |
| ttt | gat | gac | tct | gct | cgt | gag | gaa | gag | atc | ttc | ctg | tcc | ctg | cgt | gat | 2840 |
| Phe | Asp | Asp | Ser | Ala | Arg | Glu | Glu | Glu | Ile | Phe | Leu | Ser | Leu | Arg | Asp |      |
|     |     | 920 |     |     |     |     | 925 |     |     |     |     | 930 |     |     |     |      |
| cag | aac | aag | gac | gac | gtc | gag | aag | gtc | atc | cgc | atc | gca | ctc | tcg | cac | 2888 |
| Gln | Asn | Lys | Asp | Asp | Val | Glu | Lys | Val | Ile | Arg | Ile | Ala | Leu | Ser | His |      |
|     |     |     | 935 |     |     |     |     | 940 |     |     |     |     | 945 |     |     |      |
| tcg | cgt | gtc | act | gcc | aag | aac | aac | ttg | gtt | ttg | acc | ctt | ctt | gac | cag | 2936 |
| Ser | Arg | Val | Thr | Ala | Lys | Asn | Asn | Leu | Val | Leu | Thr | Leu | Leu | Asp | Gln |      |
|     | 950 |     |     |     |     | 955 |     |     |     |     | 960 |     |     |     |     |      |
| atc | aaa | cct | acg | gcc | tct | gga | gga | gcg | ctc | gac | aag | ttc | ttc | tcg | cct | 2984 |
| Ile | Lys | Pro | Thr | Ala | Ser | Gly | Gly | Ala | Leu | Asp | Lys | Phe | Phe | Ser | Pro |      |
| 965 |     |     |     |     | 970 |     |     |     |     | 975 |     |     |     |     | 980 |      |
| gtg | ctc | aag | aag | ctg | gct | gag | ctt | act | ggc | cgt | ctc | acc | gcc | aag | gtc | 3032 |
| Val | Leu | Lys | Lys | Leu | Ala | Glu | Leu | Thr | Gly | Arg | Leu | Thr | Ala | Lys | Val |      |
|     |     |     |     | 985 |     |     |     |     | 990 |     |     |     |     | 995 |     |      |
| tcg | ctc | aag | gcc | aga | gag | ctc | ctt | att | cat | gtt | cag | ttg | ccc | agc |     | 3077 |
| Ser | Leu | Lys | Ala | Arg | Glu | Leu | Leu | Ile | His | Val | Gln | Leu | Pro | Ser |     |      |
|     |     | 1000 |    |     |     | 1005 |    |     |     |     | 1010 |    |     |     |     |      |
| ttt | gag | gaa | cgc | cag | tcg | cag | atg | gag | aag | atc | ctc | cgc | tcg | agc |     | 3122 |
| Phe | Glu | Glu | Arg | Gln | Ser | Gln | Met | Glu | Lys | Ile | Leu | Arg | Ser | Ser |     |      |
|     |     | 1015 |    |     |     | 1020 |    |     |     |     | 1025 |    |     |     |     |      |
| gtc | act | gag | gag | gtt | tat | ggt | ggt | gaa | cac | gag | gcc | cgc | atg | cct |     | 3167 |
| Val | Thr | Glu | Glu | Val | Tyr | Gly | Gly | Glu | His | Glu | Ala | Arg | Met | Pro |     |      |
|     |     | 1030 |    |     |     | 1035 |    |     |     |     | 1040 |    |     |     |     |      |
| gcc | ttt | gag | aac | atc | aag | gag | ttg | gtc | gac | acc | acc | tac | aca | gtc |     | 3212 |
| Ala | Phe | Glu | Asn | Ile | Lys | Glu | Leu | Val | Asp | Thr | Thr | Tyr | Thr | Val |     |      |
|     |     | 1045 |    |     |     | 1050 |    |     |     |     | 1055 |    |     |     |     |      |
| ttt | gat | gtc | ttg | cct | aac | ttc | ttt | tac | cat | gag | tcg | ttg | cat | gtc |     | 3257 |
| Phe | Asp | Val | Leu | Pro | Asn | Phe | Phe | Tyr | His | Glu | Ser | Leu | His | Val |     |      |
|     |     | 1060 |    |     |     | 1065 |    |     |     |     | 1070 |    |     |     |     |      |
| cgc | att | gcc | gcg | ttc | gag | gtg | tac | tgc | cgt | cgt | gcc | tac | cat | gcg |     | 3302 |
| Arg | Ile | Ala | Ala | Phe | Glu | Val | Tyr | Cys | Arg | Arg | Ala | Tyr | His | Ala |     |      |
|     |     | 1075 |    |     |     | 1080 |    |     |     |     | 1085 |    |     |     |     |      |
| tac | gag | att | ttg | gac | atc | aat | tac | cac | atg | gag | cac | cag | ccc | ttg |     | 3347 |
| Tyr | Glu | Ile | Leu | Asp | Ile | Asn | Tyr | His | Met | Glu | His | Gln | Pro | Leu |     |      |
|     |     | 1090 |    |     |     | 1095 |    |     |     |     | 1100 |    |     |     |     |      |
| ctg | atc | act | tgg | aag | ttc | ttg | ctc | aac | acc | ccc | aac | aag | tcc | gag |     | 3392 |
| Leu | Ile | Thr | Trp | Lys | Phe | Leu | Leu | Asn | Thr | Pro | Asn | Lys | Ser | Glu |     |      |
|     |     | 1105 |    |     |     | 1110 |    |     |     |     | 1115 |    |     |     |     |      |
| tct | ggt | ccc | aac | cgt | gtg | gct | agt | gtc | agt | gac | atg | agt | tac | ttg |     | 3437 |
| Ser | Gly | Pro | Asn | Arg | Val | Ala | Ser | Val | Ser | Asp | Met | Ser | Tyr | Leu |     |      |
|     |     | 1120 |    |     |     | 1125 |    |     |     |     | 1130 |    |     |     |     |      |
| atc | aac | aag | gct | gac | cct | gag | cct | gtt | cgt | acc | ggt | gcc | att | ctt |     | 3482 |
| Ile | Asn | Lys | Ala | Asp | Pro | Glu | Pro | Val | Arg | Thr | Gly | Ala | Ile | Leu |     |      |
|     |     | 1135 |    |     |     | 1140 |    |     |     |     | 1145 |    |     |     |     |      |
| gcc | gtt | cgc | gac | gtg | aag | gag | ctg | gag | gac | aga | ttc | gag | agc | atc |     | 3527 |
| Ala | Val | Arg | Asp | Val | Lys | Glu | Leu | Glu | Asp | Arg | Phe | Glu | Ser | Ile |     |      |
|     |     | 1150 |    |     |     | 1155 |    |     |     |     | 1160 |    |     |     |     |      |
| ctc | aac | ttc | ttc | ccc | tct | cac | aag | tcg | aac | aag | cac | ttg | agc | cat |     | 3572 |

```
            Leu Asn Phe Phe Pro Ser His Lys Ser Asn Lys His Leu Ser His
                        1165                1170                1175 ctc gct gcc gcc agc gtc cac aac aat gtg ttg aac gtt gtc atc        3617
Leu Ala Ala Ala Ser Val His Asn Asn Val Leu Asn Val Val Ile
            1180                1185                1190 aag tcc gag tcg gtt cac ccc aac gat gat gac tac tgg ctg aac        3662
Lys Ser Glu Ser Val His Pro Asn Asp Asp Asp Tyr Trp Leu Asn
            1195                1200                1205 ctc ctc agc ccc atc gtg aag ggc gag acc gag cgc ctt cgc tcg        3707
Leu Leu Ser Pro Ile Val Lys Gly Glu Thr Glu Arg Leu Arg Ser
            1210                1215                1220 cac ggc atc cgt cgc atg acc ttc ttg atc ttc cgt cag ggc aac        3752
His Gly Ile Arg Arg Met Thr Phe Leu Ile Phe Arg Gln Gly Asn
            1225                1230                1235 tac ccc tcg tac ttc acc ttc cgt gag cgt aac aac tac gct gag        3797
Tyr Pro Ser Tyr Phe Thr Phe Arg Glu Arg Asn Asn Tyr Ala Glu
            1240                1245                1250 gat cag acc atc cgt cac atc gag ccc gcc atg gca tac cgt ctt        3842
Asp Gln Thr Ile Arg His Ile Glu Pro Ala Met Ala Tyr Arg Leu
            1255                1260                1265 gag ttg gcg cgc ttg tcc aac ttt gac atc aag ccc tgc ttc att        3887
Glu Leu Ala Arg Leu Ser Asn Phe Asp Ile Lys Pro Cys Phe Ile
            1270                1275                1280 gac aat cgc cag gtt cat gtg tac tat gct gtg ggc aag gag aac        3932
Asp Asn Arg Gln Val His Val Tyr Tyr Ala Val Gly Lys Glu Asn
            1285                1290                1295 att tcg gac tgc cgc ttc ttt gtc tgc gcc ttg gtt cgt cct ggt        3977
Ile Ser Asp Cys Arg Phe Phe Val Cys Ala Leu Val Arg Pro Gly
            1300                1305                1310 cgc ctg cgc tct agc gtt cgt acg gcg gat tac ttg att tcg gag        4022
Arg Leu Arg Ser Ser Val Arg Thr Ala Asp Tyr Leu Ile Ser Glu
            1315                1320                1325 acc gac cgt ctg ttg aac gat att ctg gat gct ctg gag att gtg        4067
Thr Asp Arg Leu Leu Asn Asp Ile Leu Asp Ala Leu Glu Ile Val
            1330                1335                1340 ggt gcc acc tac aag cag agt gac tgc aac cac ttg ttt atc aac        4112
Gly Ala Thr Tyr Lys Gln Ser Asp Cys Asn His Leu Phe Ile Asn
            1345                1350                1355 ttc atc ccc act ttc cag ttg gac gct acc gag gtt gag act gcc        4157
Phe Ile Pro Thr Phe Gln Leu Asp Ala Thr Glu Val Glu Thr Ala
            1360                1365                1370 ctc aag gga ttc att gac cgc cac ggc aag cgt ctc tgg cgt ctt        4202
Leu Lys Gly Phe Ile Asp Arg His Gly Lys Arg Leu Trp Arg Leu
            1375                1380                1385 cgc gtc act ggc gct gag att cgc ttc aat gtt cag tcc aag tct        4247
Arg Val Thr Gly Ala Glu Ile Arg Phe Asn Val Gln Ser Lys Ser
            1390                1395                1400 gcg aat ggc gtt gag gcc gac ccc gtt cct ctt cga ttc atc atc        4292
Ala Asn Gly Val Glu Ala Asp Pro Val Pro Leu Arg Phe Ile Ile
            1405                1410                1415 tcc aac gtc tct gga tat gtc ttg aac gtc gac acc tac cgc gag        4337
Ser Asn Val Ser Gly Tyr Val Leu Asn Val Asp Thr Tyr Arg Glu
            1420                1425                1430 gtt cag acc gag aag ggt gcc atc ttc aag tcg gtt ggt cct acc        4382
Val Gln Thr Glu Lys Gly Ala Ile Phe Lys Ser Val Gly Pro Thr
            1435                1440                1445 ggt ccc ttc cat ctc ttg cct gtg aac cag ccc tac ccc aca aag        4427
Gly Pro Phe His Leu Leu Pro Val Asn Gln Pro Tyr Pro Thr Lys
            1450                1455                1460
```

```
gag tgg ctt cag ccc aga cgt tac aag gca cac ttg atg ggc acg        4472
Glu Trp Leu Gln Pro Arg Arg Tyr Lys Ala His Leu Met Gly Thr
            1465                1470                1475 act tac gtc tat gac ttt ggc gag ctc ttc cgc cag gcc gtc cgt        4517
Thr Tyr Val Tyr Asp Phe Gly Glu Leu Phe Arg Gln Ala Val Arg
        1480                1485                1490 gct cag tgg aac cat gcc atc aag cag aac tct tcg ctc aag gtc        4562
Ala Gln Trp Asn His Ala Ile Lys Gln Asn Ser Ser Leu Lys Val
    1495                1500                1505 cca tcc cag gtc ttg gag atg cgc gag ctg gtc ttg gat gag aga        4607
Pro Ser Gln Val Leu Glu Met Arg Glu Leu Val Leu Asp Glu Arg
1510                1515                1520 cag cag ttg cag cag gtc gtt cgc gat gcc ggt tcc aac aac tgc        4652
Gln Gln Leu Gln Gln Val Val Arg Asp Ala Gly Ser Asn Asn Cys
        1525                1530                1535 ggc atg gtt gcc tgg att ttc act ctc cgt acc ccc gag tac ccc        4697
Gly Met Val Ala Trp Ile Phe Thr Leu Arg Thr Pro Glu Tyr Pro
    1540                1545                1550 gag ggt cga cag atc att gtc att gcc aac gat atc acc ttc aac        4742
Glu Gly Arg Gln Ile Ile Val Ile Ala Asn Asp Ile Thr Phe Asn
1555                1560                1565 att gga tcg ttt gga ccc gag gag gac ctg gtc ttc tac aag gcg        4787
Ile Gly Ser Phe Gly Pro Glu Glu Asp Leu Val Phe Tyr Lys Ala
        1570                1575                1580 tcc gag atg gcc aga aag ttg ggc att ccc cgt gtt tac ctc tct        4832
Ser Glu Met Ala Arg Lys Leu Gly Ile Pro Arg Val Tyr Leu Ser
    1585                1590                1595 gcc aac tct ggt gcc cgc att ggt ctt gct agt gaa gtg att ggt        4877
Ala Asn Ser Gly Ala Arg Ile Gly Leu Ala Ser Glu Val Ile Gly
1600                1605                1610 ctc ttc aac tct tgc tgg aac gac gct tcc aac ccc tcc aag ggc        4922
Leu Phe Asn Ser Cys Trp Asn Asp Ala Ser Asn Pro Ser Lys Gly
        1615                1620                1625 ttc aag tac atc tac ctc acg gac gct gga ctg aag cag ttg gag        4967
Phe Lys Tyr Ile Tyr Leu Thr Asp Ala Gly Leu Lys Gln Leu Glu
    1630                1635                1640 gct cag gag gag cgc tct ggt aag aag agc gtc atc aca gag acc        5012
Ala Gln Glu Glu Arg Ser Gly Lys Lys Ser Val Ile Thr Glu Thr
1645                1650                1655 att gtt gag gat ggc gag acc cgc cat aag atc acg gat gtc atc        5057
Ile Val Glu Asp Gly Glu Thr Arg His Lys Ile Thr Asp Val Ile
        1660                1665                1670 ggt gct gtc gac ggt ctt ggt gtt gag aac ttg cgc gga agt ggt        5102
Gly Ala Val Asp Gly Leu Gly Val Glu Asn Leu Arg Gly Ser Gly
    1675                1680                1685 ctg att gct gga gag acc tcg cga gcc tac gac gac atc ttt acc        5147
Leu Ile Ala Gly Glu Thr Ser Arg Ala Tyr Asp Asp Ile Phe Thr
1690                1695                1700 att act ttg gtc acc tgc cgc tct gtt ggt atc ggt gcg tac ttg        5192
Ile Thr Leu Val Thr Cys Arg Ser Val Gly Ile Gly Ala Tyr Leu
        1705                1710                1715 gtt cgt ttg ggt cag cgt act att cag aat gag ggc cag ccc atc        5237
Val Arg Leu Gly Gln Arg Thr Ile Gln Asn Glu Gly Gln Pro Ile
    1720                1725                1730 att ttg act ggt gcc cct gcc ctc aac aag ttg ctt ggt cgc gat        5282
Ile Leu Thr Gly Ala Pro Ala Leu Asn Lys Leu Leu Gly Arg Asp
1735                1740                1745 gtc tac acc tcg aac ttg cag ctc gga ggc act cag att atg tac        5327
Val Tyr Thr Ser Asn Leu Gln Leu Gly Gly Thr Gln Ile Met Tyr
        1750                1755                1760
```

| | | | | | | | | | | | | |
|---|---|---|---|---|---|---|---|---|---|---|---|---|
| aag | aac | gga | gtg | tcg | cac | ttg | acc | gct | cag | aac | gac | tat | gag | ggt | 5372 |
| Lys | Asn | Gly | Val | Ser | His | Leu | Thr | Ala | Gln | Asn | Asp | Tyr | Glu | Gly | |
| | | | 1765 | | | | 1770 | | | | 1775 | | | | |

| att | ggc | aag | atc | gtc | aac | tgg | ctc | tcg | tac | att | cct | gag | cgc | aag | 5417 |
|---|---|---|---|---|---|---|---|---|---|---|---|---|---|---|---|
| Ile | Gly | Lys | Ile | Val | Asn | Trp | Leu | Ser | Tyr | Ile | Pro | Glu | Arg | Lys | |
| | | 1780 | | | | | 1785 | | | | | 1790 | | | |

| aat | gca | ccg | gtg | ccc | atc | acg | gtc | agc | aac | gac | acc | tgg | gac | cgc | 5462 |
|---|---|---|---|---|---|---|---|---|---|---|---|---|---|---|---|
| Asn | Ala | Pro | Val | Pro | Ile | Thr | Val | Ser | Asn | Asp | Thr | Trp | Asp | Arg | |
| | | 1795 | | | | | 1800 | | | | | 1805 | | | |

| gac | atc | gac | tac | ttg | cct | ccc | aag | ggt | gca | gtc | tat | gat | ccc | cgc | 5507 |
|---|---|---|---|---|---|---|---|---|---|---|---|---|---|---|---|
| Asp | Ile | Asp | Tyr | Leu | Pro | Pro | Lys | Gly | Ala | Val | Tyr | Asp | Pro | Arg | |
| | | 1810 | | | | | 1815 | | | | | 1820 | | | |

| tgg | ttg | atc | gct | ggt | aag | gag | gct | gag | gag | gag | ggc | gcc | tct | ttc | 5552 |
|---|---|---|---|---|---|---|---|---|---|---|---|---|---|---|---|
| Trp | Leu | Ile | Ala | Gly | Lys | Glu | Ala | Glu | Glu | Glu | Gly | Ala | Ser | Phe | |
| | | 1825 | | | | | 1830 | | | | | 1835 | | | |

| cag | act | ggt | ttc | ttc | gac | aag | gat | tcg | ttt | acc | gag | aca | ttg | acg | 5597 |
|---|---|---|---|---|---|---|---|---|---|---|---|---|---|---|---|
| Gln | Thr | Gly | Phe | Phe | Asp | Lys | Asp | Ser | Phe | Thr | Glu | Thr | Leu | Thr | |
| | | 1840 | | | | | 1845 | | | | | 1850 | | | |

| ggc | tgg | gcc | cgc | acg | gtt | gtt | gtt | gga | cgt | gcc | cgt | ctc | ggt | ggt | 5642 |
|---|---|---|---|---|---|---|---|---|---|---|---|---|---|---|---|
| Gly | Trp | Ala | Arg | Thr | Val | Val | Val | Gly | Arg | Ala | Arg | Leu | Gly | Gly | |
| | | 1855 | | | | | 1860 | | | | | 1865 | | | |

| gtc | cct | atg | gga | gtg | att | gca | gtt | gag | acc | cgc | tcg | gtc | gag | cac | 5687 |
|---|---|---|---|---|---|---|---|---|---|---|---|---|---|---|---|
| Val | Pro | Met | Gly | Val | Ile | Ala | Val | Glu | Thr | Arg | Ser | Val | Glu | His | |
| | | 1870 | | | | | 1875 | | | | | 1880 | | | |

| atc | atc | cct | gct | gat | ccc | gcc | aac | ggc | gac | tct | gtc | gag | cag | gtc | 5732 |
|---|---|---|---|---|---|---|---|---|---|---|---|---|---|---|---|
| Ile | Ile | Pro | Ala | Asp | Pro | Ala | Asn | Gly | Asp | Ser | Val | Glu | Gln | Val | |
| | | 1885 | | | | | 1890 | | | | | 1895 | | | |

| ttg | atg | gag | gct | gga | aat | gtt | tgg | tac | ccc | aac | tcg | gct | tac | aag | 5777 |
|---|---|---|---|---|---|---|---|---|---|---|---|---|---|---|---|
| Leu | Met | Glu | Ala | Gly | Asn | Val | Trp | Tyr | Pro | Asn | Ser | Ala | Tyr | Lys | |
| | | 1900 | | | | | 1905 | | | | | 1910 | | | |

| act | gcg | cag | gcc | atc | aac | gac | ttc | aac | aag | gga | gag | cag | ctt | cca | 5822 |
|---|---|---|---|---|---|---|---|---|---|---|---|---|---|---|---|
| Thr | Ala | Gln | Ala | Ile | Asn | Asp | Phe | Asn | Lys | Gly | Glu | Gln | Leu | Pro | |
| | | 1915 | | | | | 1920 | | | | | 1925 | | | |

| ctg | atg | atc | ttt | gcc | aac | tgg | cgt | gga | ttc | tcg | ggt | ggt | cag | cgc | 5867 |
|---|---|---|---|---|---|---|---|---|---|---|---|---|---|---|---|
| Leu | Met | Ile | Phe | Ala | Asn | Trp | Arg | Gly | Phe | Ser | Gly | Gly | Gln | Arg | |
| | | 1930 | | | | | 1935 | | | | | 1940 | | | |

| gac | atg | tac | aat | gag | atc | ctc | aag | tac | ggt | tcc | ttc | att | gtc | gat | 5912 |
|---|---|---|---|---|---|---|---|---|---|---|---|---|---|---|---|
| Asp | Met | Tyr | Asn | Glu | Ile | Leu | Lys | Tyr | Gly | Ser | Phe | Ile | Val | Asp | |
| | | 1945 | | | | | 1950 | | | | | 1955 | | | |

| gct | ctg | agc | tca | tac | aag | cag | cct | gtg | ttt | gtc | tat | gtg | gtt | ccc | 5957 |
|---|---|---|---|---|---|---|---|---|---|---|---|---|---|---|---|
| Ala | Leu | Ser | Ser | Tyr | Lys | Gln | Pro | Val | Phe | Val | Tyr | Val | Val | Pro | |
| | | 1960 | | | | | 1965 | | | | | 1970 | | | |

| aac | gga | gag | ctt | cgt | gga | ggt | gct | tgg | gtc | gtc | gtt | gac | cct | act | 6002 |
|---|---|---|---|---|---|---|---|---|---|---|---|---|---|---|---|
| Asn | Gly | Glu | Leu | Arg | Gly | Gly | Ala | Trp | Val | Val | Val | Asp | Pro | Thr | |
| | | 1975 | | | | | 1980 | | | | | 1985 | | | |

| atc | aac | gag | gac | atg | atg | gag | atg | tat | gct | gac | aag | cgg | tca | aga | 6047 |
|---|---|---|---|---|---|---|---|---|---|---|---|---|---|---|---|
| Ile | Asn | Glu | Asp | Met | Met | Glu | Met | Tyr | Ala | Asp | Lys | Arg | Ser | Arg | |
| | | 1990 | | | | | 1995 | | | | | 2000 | | | |

| gcc | ggt | gtc | ttg | gag | cct | gag | ggt | att | gtt | gag | atc | aag | ttc | cgt | 6092 |
|---|---|---|---|---|---|---|---|---|---|---|---|---|---|---|---|
| Ala | Gly | Val | Leu | Glu | Pro | Glu | Gly | Ile | Val | Glu | Ile | Lys | Phe | Arg | |
| | | 2005 | | | | | 2010 | | | | | 2015 | | | |

| aag | gcc | cag | ttg | ttg | gcg | acc | atg | gag | cgt | ttg | gac | gac | aag | tac | 6137 |
|---|---|---|---|---|---|---|---|---|---|---|---|---|---|---|---|
| Lys | Ala | Gln | Leu | Leu | Ala | Thr | Met | Glu | Arg | Leu | Asp | Asp | Lys | Tyr | |
| | | 2020 | | | | | 2025 | | | | | 2030 | | | |

| cgc | gca | ttg | aag | gcc | cag | tac | gag | aac | cca | gcc | ttg | gtt | ggt | acc | 6182 |
|---|---|---|---|---|---|---|---|---|---|---|---|---|---|---|---|
| Arg | Ala | Leu | Lys | Ala | Gln | Tyr | Glu | Asn | Pro | Ala | Leu | Val | Gly | Thr | |
| | | 2035 | | | | | 2040 | | | | | 2045 | | | |

| gag | cgc | gag | gag | atc | aag | acg | aag | ctg | acg | gag | cgc | gag | caa | gag | 6227 |
|---|---|---|---|---|---|---|---|---|---|---|---|---|---|---|---|
| Glu | Arg | Glu | Glu | Ile | Lys | Thr | Lys | Leu | Thr | Glu | Arg | Glu | Gln | Glu | |

|     |     |     | 2050 |     |     |     | 2055 |     |     |     | 2060 |     |      |
| --- | --- | --- | --- | --- | --- | --- | --- | --- | --- | --- | --- | --- | ---- |
| ctg | ttg | cct | gtg | tac | cag | cag | ctg | gcg | atc | caa | ttc | gcg | gat  ctg | 6272 |
| Leu | Leu | Pro | Val | Tyr | Gln | Gln | Leu | Ala | Ile | Gln | Phe | Ala | Asp  Leu |
|     |     |     | 2065 |     |     |     | 2070 |     |     |     | 2075 |     |      |

```
ctg ttg cct gtg tac cag cag ctg gcg atc caa ttc gcg gat ctg      6272
Leu Leu Pro Val Tyr Gln Gln Leu Ala Ile Gln Phe Ala Asp Leu
         2065                2070                2075 cac gac act gcg gga cgc atg aag gcc aag ggc acg att cgt gaa      6317
His Asp Thr Ala Gly Arg Met Lys Ala Lys Gly Thr Ile Arg Glu
         2080                2085                2090 gcc ttg gac tgg acc aat gcc cgt cgc tac ttc tac tgg cgc gtg      6362
Ala Leu Asp Trp Thr Asn Ala Arg Arg Tyr Phe Tyr Trp Arg Val
         2095                2100                2105 cgc aga aga ttg gct gag gag tac att cgt cgc aag atg gct att      6407
Arg Arg Arg Leu Ala Glu Glu Tyr Ile Arg Arg Lys Met Ala Ile
         2110                2115                2120 gcc aac aag gac ttg agc cgt gag gag cag acc aag tcg ctg ctg      6452
Ala Asn Lys Asp Leu Ser Arg Glu Glu Gln Thr Lys Ser Leu Leu
         2125                2130                2135 tct tgg ttc ggc cgt gac acg gtg cac tcg agc gag agc gag ctg      6497
Ser Trp Phe Gly Arg Asp Thr Val His Ser Ser Glu Ser Glu Leu
         2140                2145                2150 gag cag atc tgg gaa tct gac gat cgc gtg gtg ttg gag tgg ttc      6542
Glu Gln Ile Trp Glu Ser Asp Asp Arg Val Val Leu Glu Trp Phe
         2155                2160                2165 gag gga cac gag agc aag gtg act gga ttg atc cag gag ctg aac      6587
Glu Gly His Glu Ser Lys Val Thr Gly Leu Ile Gln Glu Leu Asn
         2170                2175                2180 aat gcg gcg act gcc agc gag gtg ctg aga atg tac acc tcc aac      6632
Asn Ala Ala Thr Ala Ser Glu Val Leu Arg Met Tyr Thr Ser Asn
         2185                2190                2195 cgc gct ggt gtg gtc gag ggc ttc gat cgt atc ctt cag agc ctg      6677
Arg Ala Gly Val Val Glu Gly Phe Asp Arg Ile Leu Gln Ser Leu
         2200                2205                2210 tcg gac cag gag aag cag gac atc ctt gcc aag ttc gcc acg atg      6722
Ser Asp Gln Glu Lys Gln Asp Ile Leu Ala Lys Phe Ala Thr Met
         2215                2220                2225 acc gtt taagaattga tttttttnnga atcaattttt agagtagagt gagagtagaa  6778
Thr Val cagagtggag gaactggaca ctcctccatc tttgtgttgt aattataaaa ttcatatcca 6838 ttttcttaca aaaaaaaaaa aaaaaaa                                    6865
```

<210> SEQ ID NO 5
<211> LENGTH: 7892
<212> TYPE: DNA
<213> ORGANISM: Mortierella alpina

<400> SEQUENCE: 5

```
atgactacca acgtacagtc cttcattggt aagaagagtg caacgctttg gacgctatcc     60
tttcttgtga ccgtgggaca aaaaaaaagg caaaaaaaag cagctggcga tcttttgat    120 ccgctgtaag aaacgccaat gagaggcgag aaatgtgcgg gcagaacgat cgctgaggct   180
tttttgctct gtagcgggaa aaggacgtgg acatctggtt gcgttttcca tcgcgagcgt   240
ggtcgataaa ttttcgcta cgacgatgac tttctgctaa ccgcgatact ttgcgcgttg    300
ctctgtgaat tgtaggagga aacgcattag agaacgcccc tgctggagct gtccgcgagt   360
ttgttaacca gcatggaggc cacagcgtga tcaccaagat cctgatcgcc aacaacggta    420
ttgcggccgt caaggagatc cgatctgtcc gcaagtgggc gtacgagacc tttggagatg    480
agcgtgcgat ccagttcacg gtcatggcta cgccagagga tctgaagatc aatgctgaat    540
```

```
atatccgcat ggccgaccag tatgtcgaag taccgggagg atccaacaac aacaactacg    600
ccaacgttga cctcattgtc gacattgccg aacgcaccgg cgtccatgct gtgtgggctg    660
gatggtaagt caagcagttt tgcttgtttg cagctgcaga tcggggttca gttttatctt    720
atggtcgtcg tgtagccaca gtgctttggt gggtgtggat catgcatgaa tatcggcgtc    780
tgttctcagt gggtggagat tgcacaaaga atgtgtttgc cttcggatgt ggccatggtt    840
cgtgcttggg catcttttt gggttgtgtg tttgatgctg acagcaagga atcgatggtt    900
gctatcaaat atctcgttcc ccaaaaacga aaaaagggg ctcccaaaaa aaaaactccc    960
cagcaaaaaa aaaaaaaaaa aaaattgaag tgcggtcaca gcggactatt gaaggagaaa   1020
aaaaaaaaga gcggggcaga accttgtcca agtagagtag gacctcggag tctgtctttg   1080
gccttttatt ttctattgac tcttgcttgg tgatatgggc ttcaagggat tgaaagcctc   1140
cgagacggcg tgctagtgca tgggttggct acagtttgtt atgcgtgtga agaaacaagc   1200
gcgtcgacag gcgtgacagc agcttttac tcacaatact cttcgcctc cttttccttt    1260 tcgttacagg ggacatgcct cggagaaccc caaactccca gagtctcttc gcgacagccc   1320
tcaaaagatc atcttcatcg gaccccccgg ctccgccatg cgctcgttgg gtgacaagat   1380
ctcgtccacg atcgtcgctc aatcggccga cgtccctacg atgggctggt ccggaactgg   1440
catcacagag actaccatgg atgctaatgg tttcgtcatg gtgcccgagg atgcttacca   1500
ggctgcctgt gtcaccgatg cagaggatgg tcttcagaag gcccacacca tcggcttccc   1560
ggtcatgatc aaggcttcag agggtggtgg aggaaagggt attcgtaagg ttgaggaacc   1620
agaaaagttc gctcaggcct tcaaccaggt tttgggcgag gtccccggtt ccccgtctt    1680 catcatgaag ttggctggta acgcgcgcca tctggaggtc cagcttttgg ccgatcagta   1740
tggaaatgcc atctcgctct ttggacgcga ttgctctgtc cagcgtcgcc atcagaagat   1800
tattgaggaa gctcccgtca ccattgccaa gcccgacacc ttcgagtcga tggagaaggc   1860
tgcagtgcgt ctggccaagt tggtcggata cgtttctgca ggtaccgtcg agtacctgta   1920
ctcgcactcg actgacacct tcttcttcct ggagttgaac cccagacttc aggtcgagca   1980
tcctaccacc gagatggtct caggtgtcaa cctgccagct gctcagctcc agatcgccat   2040
gggtcttcct ttgaaccgca tcaaggacat ccgtgttctc tatggtcttc aacccacagg   2100
aacgtccgag atcgactttg agttttcaca gcagatctcg tatgagactc agcgcaagcc   2160
cgcccctaag ggacacgtca ttgctgtccg tatcacagcc gagaacccg atgcaggatt    2220 caagcccctca gcggaatga tgcaggaact caatttcaga tcatctacca acgtctgggg   2280
ctacttctct gtcaactctg caggaggact gcacgagttt gccgattctc agtttggtca   2340
tatctttgcc tatggacagg atcgtggtca gtctagaaag aacatggtcg ttgccctcaa   2400
ggaactctcc attcgtggtg atttccgcac tacggtcgag tacttgatcc gccttttgga   2460
gacacaggag ttcgaggaaa acaccattaa cactggctgg ctcgacagct tgatctccaa   2520
caacctcact gctgaacgcc ctgagaccat gttggctgtc atgtgtggtg ctgttaacag   2580
agcccacacc atctccgaga actgcattaa ggagtacaag aagtcgctgg agaagggtca   2640
agtgcctagc aaggacgttc tgcgctcggt caaccagctt gactttattt acgacggcgt   2700
ccgctacaac ttcaccgcca ctcgctctgg acccaactcg tacactctgt acttgaatgg   2760
atccatgatc tccatctctg tgcgtccatt gaccgatggc ggtctcttgg tccttttgga   2820
tggcaaggtc agtccaaatt gtatttgtga aatgaagtca aatgaagtcg gcgtcatgtg   2880
ctaacctgtt atctgctttc cttttctatt taaaggctca cacgacttac tcgttggaag   2940
```

```
aggtccaggc cactcgcctg atggtcgatg gaaagacttg tttgttggag aaggagaacg    3000
accctactca actccgctcc ccctccccag gcaaacttgt tcgctacctt gtcgagtctg    3060
gcgaccatgt tacggccagc caggcctatg ctgagattga ggtcatgaag atgtatatgc    3120
ccttgatcgc caccgaggac ggtattgtgc agttcatcaa gcaacccggc accactctgg    3180
atgctggtga tatcattggt atcctcagct tggacgatcc ctcccgcgtt cgccacgcta    3240
agcccttcga aggtcagctc cctcccatgg gtcagcccac cattcacgga gctaagcccc    3300
atcagcgtta ccgcgagctg cgactcgtcc tcgacaatgc catggatggc tacgataacc    3360
aggctttggt ccagcctacg ctgaaggaga tcttttgaggt cctccagacc ccggagctgc    3420
cctacttgga attcaacgag gtctttgctt cgctaagcgg aaggtaaaaa aaaaaaaaaa    3480
aaaaaaaagg aactggcccc aggttttatt cccagggtgt ccgcattcgc gcggcaattt    3540
attgatccga gttgtactga ccttaattgt ctcatgtcaa tattcataga atcccaccca    3600
agctggaaat tgccctgcac caggaggtgg atcagtccat gaagaaccac gagcacttcc    3660
ccgctcgtac tcttcaggcc ctgattgact cgcactgccg cgccaacttc tccaaggccg    3720
ccgatatcaa tgcgttccaa gcctcggtgg gacctctgac cgccatcatc aaggagtacc    3780
aacacggttt gaaaactcac tcctggggct tcattgctga ttacctcaac aagtaccatg    3840
aagtcgagtc gctctttgat gactctgctc gtgaggaaga gatcttcctg tccctgcgtg    3900
atcagaacaa ggacgacgtc gagaaggtca tccgcatcgc actctcgcac tcgcgtgtca    3960
ctgccaagaa caacttggtt ttgacccttc ttgaccagat caaacctacg gcctctggag    4020
gagcgctcga caagttcttc tcgcctgtgc tcaagaagct ggctgagctt actggccgtc    4080
tcaccgccaa ggtctcgctc aaggccagag agctccttat tcatgttcag ttgcccagct    4140
ttgaggaacg ccagtcgcag atggagaaga tcctccgctc gagcgtcact gaggaggttt    4200
atggtggtga acacgaggcc cgcatgcctg cctttgagaa catcaaggag ttggtcgaca    4260
ccacctacac agtctttgat gtcttgccta acttcttttta ccatgagtcg ttgcatgtcc    4320
gcattgccgc gttcgaggtg tactgccgtc gtgcctacca tgcgtacgag atttttggaca    4380 tcaattacca catggagcac cagcccttgc tgatcacttg gaagttcttg ctcaacaccc    4440
ccaacaagtc cgagtctggt cccaaccgtg tggctagtgt cagtgacatg agttacttga    4500
tcaacaaggc tgaccctgag cctgttcgta ccggtgccat tcttgccgtt cgcgacgtga    4560
aggagctgga ggacagattc gagagcatcc tcaacttctt cccctctcac aagtcgaaca    4620
agcacttgag ccatctcgct gccgccagcg tccacaacaa tgtgttgaac gttgtcatca    4680
agtccgagtc ggttcacccc aacgatgatg actactggct gaacctcctc agccccatcg    4740
tgaagggcga gaccgagcgc cttcgctcgc acggcatccg tcgcatgacc ttcttgatct    4800
tccgtcaggg caactacccc tcgtacttca ccttccgtga gcgtaacaac tacgctgagg    4860
atcagaccat ccgtcacatc gagcccgcca tggcataccg tcttgagttg gcgcgcttgt    4920
ccaactttga catcaagccc tgcttcattg acaatcgcca ggttcatgtg tactatgctg    4980
tgggcaagga gaacatttcg gactgccgct tctttgtctg cgccttggtt cgtcctggtc    5040
gcctgcgctc tagcgttcgt acggcggatt acttgatttc ggagaccgac cgtctgttga    5100
acgatattct ggatgctctg gagattgtgg gtgccaccta caagcagagt gactgcaacc    5160
acttgtttat caacttcatc cccactttcc agttggacgc taccgaggtt gagactgccc    5220
tcaagggatt cattgaccgc cacggcaagc gtctctggcg tcttcgcgtc actggcgctg    5280
```

```
agattcgctt caatgttcag tccaagtctg cgaatggcgt tgaggccgac cccgttcctc    5340
ttcgattcat catctccaac gtctctggat atgtcttgaa cgtcgacacc taccgcgagg    5400
ttcagaccga aagggtgcc atcttcaagt cggttggtcc taccggtccc ttccatctct     5460
tgcctgtgaa ccagccctac cccacaaagg agtggcttca gcccagacgt tacaaggcac    5520
acttgatggg cacgacttac gtctatgact ttggcgagct cttccgccag gccgtccgtg    5580
ctcagtggaa ccatgccatc aagcagaact cttcgctcaa ggtccatcc caggtcttgg     5640
agatgcgcga gctggtcttg gatgagagac agcagttgca gcaggtcgtt cgcgatgccg    5700
gttccaacaa ctgcggcatg gttgcctgga ttttcactct ccgtaccccc gagtaccccg    5760
agggtcgaca gatcattgtc attgccaacg atatcacctt caacattgga tcgtttggac    5820
ccgaggagga cctggtcttc tacaaggcgt ccgagatggc cagaaagttg gcattcccc     5880
gtgtttacct ctctgccaac tctggtgccc gcattggtct tgctagtgaa gtgattggtc    5940
tcttcaactc ttgctggaac gacgcttcca acccctccaa gggcttcaag tacatctacc    6000
tcacggacgc tggactgaag cagttggagg ctcaggagga gcgctctggt aagaagagcg    6060
tcatcacaga gaccattgtt gaggatggcg agacccgcca taagatcacg gatgtcatcg    6120
gtgctgtcga cggtcttggt gttgagaact tgcgcggaag tggtctgatt gctggagaga    6180
cctcgcgagc ctacgacgac atctttacca ttactttggt cacctgccgc tctgttggtg    6240
agtactccgc acaatgactt gtcaagcaat tgctatcctt ttatgatcga cctgtattct    6300
aattctgcaa attgatttc acactgctca ctttaggtat cggtgcgtac ttggttcgtt     6360
tgggtcagcg tactattcag aatgagggcc agcccatcat tttgactggt gccctgccc     6420
tcaacaagtt gcttggtcgc gatgtctaca cctcgaactt gcagctcgga ggcactcaga    6480
ttatgtacaa gaacggagtg tcgcacttga ccgctcagaa cgactatgag ggtattggca    6540
agatcgtcaa ctggctctcg tacattcctg agcgcaagaa tgcaccggtg cccatcacgg    6600
tcagcaacga cacctgggac cgcgacatcg actacttgcc tcccaagggt gcagtctatg    6660
atccccgctg gttgatcgct ggtaaggagg ctgaggagga gggcgcctct ttccagactg    6720
gtttcttcga caaggattcg tttaccgaga cattgacggg ctgggcccgc acggttgttg    6780
ttggacgtgc ccgtctcggt ggtgtcccta tgggagtgat tgcagttgag acccgctcgg    6840
tcgagcacat catccctgct gatcccgcca acgcgactc tgtcgagcag gtcttgatgg     6900
aggctggaaa tgtttggtac cccaactcgg cttacaagac tgcgcaggcc atcaacgact    6960
tcaacaaggg agagcagctt ccactgatga tcttttgccaa ctggcgtgga ttctcgggtg    7020
gtcagcgcga catgtacaat gagatcctca agtacggttc cttcattgtc gatgctctga    7080
gctcatacaa gcagcctgtg tttgtctatg tggttcccaa cggagagctt cgtggaggtg    7140
cttgggtcgt cgttgaccct actatcaacg aggacatgat ggagatgtat gctgacaagc    7200
ggtcaagagc cggtgtcttg gagcctgagg gtattgttga gatcaagttc cgtaaggccc    7260
agttgttggc gaccatggag cgtttggacg acaagtaccg cgcattgaag gcccagtacg    7320
agaacccagc cttggttggt accgagcgcg aggagatcaa gacgaagctg acggagcgcg    7380
agcaagagct gttgcctgtg taccagcagc tggcgatcca attcgcggat ctgcacgaca    7440
ctgcgggacg catgaaggcc aagggcacga ttcgtgaagc cttggactgg accaatgccc    7500
gtcgctactt ctactggcgc gtgcgcagaa gattggctga ggagtacatt cgtcgcaaga    7560
tggctattgc caacaaggac ttgagccgtg aggagcagac caagtcgctg ctgtcttggt    7620
tcggccgtga cacggtgcac tcgagcgaga gcgagctgga gcagatctgg gaatctgacg    7680
```

```
atcgcgtggt gttggagtgg ttcgagggac acgagagcaa ggtgactgga ttgatccagg    7740
agctgaacaa tgcggcgact gccagcgagg tgctgagaat gtacacctcc aaccgcgctg    7800
gtgtggtcga gggcttcgat cgtatccttc agagcctgtc ggaccaggag aagcaggaca    7860
tccttgccaa gttcgccacg atgaccgttt aa                                  7892
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gccaactggc gtggattctc                                                  20
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
gtcctcgttg atagtagggt c                                                21
```

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
tggtgccggg ttgct                                                       15
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gcaaacttgt tcgctacctt g                                                21
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
tcgttctcct tctccaacaa                                                  20
```

<210> SEQ ID NO 11
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 11
caggcctatg ctgagattga g                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggacctctt ccaacgagta a                                              21

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagggcgttc agcagtg                                                   17

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgagtacttg atccgccttt                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggaaatcacc acgaatggag                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggagttcgag gaaaacacca                                                20

<210> SEQ ID NO 17
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 17
tgaccacgat cctgtccata                                                   20

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcgggcttgg caatg                                                        15

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atctggaggt ccagcttttg                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcgttaccag ccaacttcat                                                   20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcgtcgccat cagaagatta                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aggcctgagc gaactttcct                                                   20

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 23
gcggcggccg ctcccactga ctcaagcgg                                           29

<210> SEQ ID NO 24
<211> LENGTH: 1716
<212> TYPE: DNA
<213> ORGANISM: Mortierella alpina
<220> FEATURE:
<223> OTHER INFORMATION: Origin: M. alpina strain CBS528.72

<400> SEQUENCE: 24
aacaacaaca actatgcgaa cgttgacctc attgtcgaca ttgccgaacg caccggcgtt    60
catgccgtgt gggctggatg gtaagtcaag cagttttgcc tgttggcaaa tggcagatcg   120
gggttcaatt tcatggcgtg gccgccgtgt ggatgaaaag cgcttgatga gaggcgaggg   180
agggcgagga tgtcgcatga atgtcggcgt ctgttctcag tgggtgaaga ttgtacaacg   240
agggtgtttg tccccgggcg tggccatggt tcgtgcttgg gcatcttttt tgggttgtgt   300
gtttgatgct gacagcaagg aatcgatggt tgctatcacc aatttcattc cccaaaaacg   360
aaaaaaaaaa aaaaaaaggg tctcccaaaa aaaaaaactc cccagcaaaa aaaaaaaaaa   420
attgaaatgc ggtcacagcg gactcttaca gagaaaaaaa aaagagcggg gcagaacctt   480
gtccgagtaa gagtgcggaa gagtagggaa cccggtgtct atctttggcc cactgttcac   540
tcttgcctgt tgagcctcaa gggtttggtg acctccgaga cggcgcacaa gcgcgcgggt   600
cagcagcagt gcgctatgtg tgtgaagaat caaccgcgtc acctggccat ggtagctctc   660
cactcaccat gcatcacttc ctttctctct cgccacaggg gacatgcctc cgaaaacccc   720
aagctgccag agtcccttcg cgacagccct cagaagatca tcttcatcgg tcccccggc   780
tccgccatgc gctcgctggg tgacaagatc tcgtccacga tcgtcgctca gtccgccgac   840
gttcctacta tgggctggtc cggaactggc atcacagaaa ctgccatgga tgccaatggc   900
tttgtcactg tgcccgacga cgcctaccag gctgcctgtg tcactgatgc agaggatggt   960
cttcagaagg ctcacaccat tggcttcccc atcatgatca aagcctcgga gggaggtgga  1020
ggaaaaggta tccgtaaggt tgaggatcca gaaaagttcg ctcaggcctt caaccaagtt  1080
ctgggtgagg tccccggttc ccccgtcttc atcatgaagt tggctggtaa tgcccgccat  1140
ctggaggtcc agcttttagc cgatcagtac ggacacgcca tctcgctctt cggacgcgat  1200
tgctcggtcc agcgtcgcca tcaaaagatc attgaggagg ctcccgtcac cattgccaag  1260
cccgacactt ttgagtcgat ggagaaggct gcagtgcgtc tggctaagct ggtcggatac  1320
gtctctgcag gtaccgtcga atacctgtat tcgcactcga ccgacacctt cttcttcctg  1380
gaattgaacc ccagacttca ggttgagcat cctaccaccg agatggtttc tggtgttaac  1440
ctgccagctg ctcagcttca ggtcgccatg ggtcttcctt tgaaccgcat caaggatatc  1500
cgtgtcctct atggccttca gcctaccgga acctccgaga tcgactttga gttctctcag  1560
cagatctcgt atgagaccca gcgcaaaccc gccccaagg gacacgtcat tgccgttcgt  1620
attacggccg agaaccctga tgctggattc aagcccctcga gcggaatgat gcaggagctc  1680
aacttccgat cctcgacgaa ggtttgggc tacttt                              1716

<210> SEQ ID NO 25
<211> LENGTH: 366
<212> TYPE: PRT
<213> ORGANISM: Mortierella alpina
<220> FEATURE:
<223> OTHER INFORMATION: Origin: M. alpina strain CBS528.72

<400> SEQUENCE: 25

Asn Asn Asn Asn Tyr Ala Asn Val Asp Leu Ile Val Asp Ile Ala Glu
1               5                   10                  15

Arg Thr Gly Val His Ala Val Trp Ala Gly Trp Gly His Ala Ser Glu
            20                  25                  30

Asn Pro Lys Leu Pro Glu Ser Leu Arg Asp Ser Pro Gln Lys Ile Ile
        35                  40                  45

Phe Ile Gly Pro Pro Gly Ser Ala Met Arg Ser Leu Gly Asp Lys Ile
    50                  55                  60

Ser Ser Thr Ile Val Ala Gln Ser Ala Asp Val Pro Thr Met Gly Trp
65                  70                  75                  80

Ser Gly Thr Gly Ile Thr Glu Thr Ala Met Asp Ala Asn Gly Phe Val
                85                  90                  95

Thr Val Pro Asp Asp Ala Tyr Gln Ala Ala Cys Val Thr Asp Ala Glu
            100                 105                 110

Asp Gly Leu Gln Lys Ala His Thr Ile Gly Phe Pro Ile Met Ile Lys
        115                 120                 125

Ala Ser Glu Gly Gly Gly Gly Lys Gly Ile Arg Lys Val Glu Asp Pro
    130                 135                 140

Glu Lys Phe Ala Gln Ala Phe Asn Gln Val Leu Gly Glu Val Pro Gly
145                 150                 155                 160

Ser Pro Val Phe Ile Met Lys Leu Ala Gly Asn Ala Arg His Leu Glu
                165                 170                 175

Val Gln Leu Leu Ala Asp Gln Tyr Gly His Ala Ile Ser Leu Phe Gly
            180                 185                 190

Arg Asp Cys Ser Val Gln Arg Arg His Gln Lys Ile Ile Glu Glu Ala
        195                 200                 205

Pro Val Thr Ile Ala Lys Pro Asp Thr Phe Glu Ser Met Glu Lys Ala
    210                 215                 220

Ala Val Arg Leu Ala Lys Leu Val Gly Tyr Val Ser Ala Gly Thr Val
225                 230                 235                 240

Glu Tyr Leu Tyr Ser His Ser Thr Asp Thr Phe Phe Phe Leu Glu Leu
                245                 250                 255

Asn Pro Arg Leu Gln Val Glu His Pro Thr Thr Glu Met Val Ser Gly
            260                 265                 270

Val Asn Leu Pro Ala Ala Gln Leu Gln Val Ala Met Gly Leu Pro Leu
        275                 280                 285

Asn Arg Ile Lys Asp Ile Arg Val Leu Tyr Gly Leu Gln Pro Thr Gly
    290                 295                 300

Thr Ser Glu Ile Asp Phe Glu Phe Ser Gln Ile Ser Tyr Glu Thr
305                 310                 315                 320

Gln Arg Lys Pro Ala Pro Lys Gly His Val Ile Ala Val Arg Ile Thr
                325                 330                 335

Ala Glu Asn Pro Asp Ala Gly Phe Lys Pro Ser Ser Gly Met Met Gln
            340                 345                 350

Glu Leu Asn Phe Arg Ser Ser Thr Lys Val Trp Gly Tyr Phe
        355                 360                 365

<210> SEQ ID NO 26
<211> LENGTH: 8
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 26 gcggccgc                                                                    8

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cccgaaacag cgcagaaaat tag                                                  23

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccagaccggt tttctcgtcc acgtg                                                25

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctgcagcgag gagccgtaat                                                      20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgcattggtc ttgctagtga                                                      20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aagtgcgaca ctccgttctt                                                      20

<210> SEQ ID NO 32
<211> LENGTH: 28
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 32
atgactacca acgtacagtc cttcattg                                            28

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttaaacggtc atcgtggcga acttggc                                             27

<210> SEQ ID NO 34
<211> LENGTH: 2233
<212> TYPE: PRT
<213> ORGANISM: Saccharomyces cerevisiae
<220> FEATURE:
<223> OTHER INFORMATION: Saccharomyces cerevisiae cellular ACC

<400> SEQUENCE: 34

Met Ser Glu Glu Ser Leu Phe Glu Ser Ser Pro Gln Lys Met Glu Tyr
1               5                   10                  15

Glu Ile Thr Asn Tyr Ser Glu Arg His Thr Glu Leu Pro Gly His Phe
            20                  25                  30

Ile Gly Leu Asn Thr Val Asp Lys Leu Glu Glu Ser Pro Leu Arg Asp
        35                  40                  45

Phe Val Lys Ser His Gly Gly His Thr Val Ile Ser Lys Ile Leu Ile
    50                  55                  60

Ala Asn Asn Gly Ile Ala Ala Val Lys Glu Ile Arg Ser Val Arg Lys
65                  70                  75                  80

Trp Ala Tyr Glu Thr Phe Gly Asp Asp Arg Thr Val Gln Phe Val Ala
                85                  90                  95

Met Ala Thr Pro Glu Asp Leu Glu Ala Asn Ala Glu Tyr Ile Arg Met
            100                 105                 110

Ala Asp Gln Tyr Ile Glu Val Pro Gly Gly Thr Asn Asn Asn Asn Tyr
        115                 120                 125

Ala Asn Val Asp Leu Ile Val Asp Ile Ala Glu Arg Ala Asp Val Asp
    130                 135                 140

Ala Val Trp Ala Gly Trp Gly His Ala Ser Glu Asn Pro Leu Leu Pro
145                 150                 155                 160

Glu Lys Leu Ser Gln Ser Lys Arg Lys Val Ile Phe Ile Gly Pro Pro
                165                 170                 175

Gly Asn Ala Met Arg Ser Leu Gly Asp Lys Ile Ser Ser Thr Ile Val
            180                 185                 190

Ala Gln Ser Ala Lys Val Pro Cys Ile Pro Trp Ser Gly Thr Gly Val
        195                 200                 205

Asp Thr Val His Val Asp Glu Lys Thr Gly Leu Val Ser Val Asp Asp
    210                 215                 220

Asp Ile Tyr Gln Lys Gly Cys Cys Thr Ser Pro Glu Asp Gly Leu Gln
225                 230                 235                 240

Lys Ala Lys Arg Ile Gly Phe Pro Val Met Ile Lys Ala Ser Glu Gly
                245                 250                 255

Gly Gly Gly Lys Gly Ile Arg Gln Val Glu Arg Glu Glu Asp Phe Ile

```
                260                 265                 270
Ala Leu Tyr His Gln Ala Ala Asn Glu Ile Pro Gly Ser Pro Ile Phe
            275                 280                 285

Ile Met Lys Leu Ala Gly Arg Ala Arg His Leu Glu Val Gln Leu Leu
            290                 295                 300

Ala Asp Gln Tyr Gly Thr Asn Ile Ser Leu Phe Gly Arg Asp Cys Ser
305                 310                 315                 320

Val Gln Arg Arg His Gln Lys Ile Ile Glu Glu Ala Pro Val Thr Ile
            325                 330                 335

Ala Lys Ala Glu Thr Phe His Glu Met Glu Lys Ala Ala Val Arg Leu
            340                 345                 350

Gly Lys Leu Val Gly Tyr Val Ser Ala Gly Thr Val Glu Tyr Leu Tyr
            355                 360                 365

Ser His Asp Asp Gly Lys Phe Tyr Phe Leu Glu Leu Asn Pro Arg Leu
            370                 375                 380

Gln Val Glu His Pro Thr Thr Glu Met Val Ser Gly Val Asn Leu Pro
385                 390                 395                 400

Ala Ala Gln Leu Gln Ile Ala Met Gly Ile Pro Met His Arg Ile Ser
            405                 410                 415

Asp Ile Arg Thr Leu Tyr Gly Met Asn Pro His Ser Ala Ser Glu Ile
            420                 425                 430

Asp Phe Glu Phe Lys Thr Gln Asp Ala Thr Lys Lys Gln Arg Arg Pro
            435                 440                 445

Ile Pro Lys Gly His Cys Thr Ala Cys Arg Ile Thr Ser Glu Asp Pro
            450                 455                 460

Asn Asp Gly Phe Lys Pro Ser Gly Gly Thr Leu His Glu Leu Asn Phe
465                 470                 475                 480

Arg Ser Ser Ser Asn Val Trp Gly Tyr Phe Ser Val Gly Asn Asn Gly
            485                 490                 495

Asn Ile His Ser Phe Ser Asp Ser Gln Phe Gly His Ile Phe Ala Phe
            500                 505                 510

Gly Glu Asn Arg Gln Ala Ser Arg Lys His Met Val Val Ala Leu Lys
            515                 520                 525

Glu Leu Ser Ile Arg Gly Asp Phe Arg Thr Thr Val Glu Tyr Leu Ile
            530                 535                 540

Lys Leu Leu Glu Thr Glu Asp Phe Glu Asp Asn Thr Ile Thr Thr Gly
545                 550                 555                 560

Trp Leu Asp Asp Leu Ile Thr His Lys Met Thr Ala Glu Lys Pro Asp
            565                 570                 575

Pro Thr Leu Ala Val Ile Cys Gly Ala Ala Thr Lys Ala Phe Leu Ala
            580                 585                 590

Ser Glu Glu Ala Arg His Lys Tyr Ile Glu Ser Leu Gln Lys Gly Gln
            595                 600                 605

Val Leu Ser Lys Asp Leu Leu Gln Thr Met Phe Pro Val Asp Phe Ile
            610                 615                 620

His Glu Gly Lys Arg Tyr Lys Phe Thr Val Ala Lys Ser Gly Asn Asp
625                 630                 635                 640

Arg Tyr Thr Leu Phe Ile Asn Gly Ser Lys Cys Asp Ile Ile Leu Arg
            645                 650                 655

Gln Leu Ser Asp Gly Gly Leu Leu Ile Ala Ile Gly Gly Lys Ser His
            660                 665                 670

Thr Ile Tyr Trp Lys Glu Glu Val Ala Ala Thr Arg Leu Ser Val Asp
            675                 680                 685
```

```
Ser Met Thr Thr Leu Leu Glu Val Glu Asn Asp Pro Thr Gln Leu Arg
    690                 695                 700

Thr Pro Ser Pro Gly Lys Leu Val Lys Phe Leu Val Glu Asn Gly Glu
705                 710                 715                 720

His Ile Ile Lys Gly Gln Pro Tyr Ala Glu Ile Glu Val Met Lys Met
                725                 730                 735

Gln Met Pro Leu Val Ser Gln Glu Asn Gly Ile Val Gln Leu Leu Lys
            740                 745                 750

Gln Pro Gly Ser Thr Ile Val Ala Gly Asp Ile Met Ala Ile Met Thr
        755                 760                 765

Leu Asp Asp Pro Ser Lys Val Lys His Ala Leu Pro Phe Glu Gly Met
770                 775                 780

Leu Pro Asp Phe Gly Ser Pro Val Ile Glu Gly Thr Lys Pro Ala Tyr
785                 790                 795                 800

Lys Phe Lys Ser Leu Val Ser Thr Leu Glu Asn Ile Leu Lys Gly Tyr
                805                 810                 815

Asp Asn Gln Val Ile Met Asn Ala Ser Leu Gln Gln Leu Ile Glu Val
            820                 825                 830

Leu Arg Asn Pro Lys Leu Pro Tyr Ser Glu Trp Lys Leu His Ile Ser
        835                 840                 845

Ala Leu His Ser Arg Leu Pro Ala Lys Leu Asp Glu Gln Met Glu Glu
850                 855                 860

Leu Val Ala Arg Ser Leu Arg Arg Gly Ala Val Phe Pro Ala Arg Gln
865                 870                 875                 880

Leu Ser Lys Leu Ile Asp Met Ala Val Lys Asn Pro Glu Tyr Asn Pro
                885                 890                 895

Asp Lys Leu Leu Gly Ala Val Val Glu Pro Leu Ala Asp Ile Ala His
            900                 905                 910

Lys Tyr Ser Asn Gly Leu Glu Ala His Glu His Ser Ile Phe Val His
        915                 920                 925

Phe Leu Glu Glu Tyr Tyr Glu Val Lys Leu Phe Asn Gly Pro Asn
930                 935                 940

Val Arg Glu Glu Asn Ile Ile Leu Lys Leu Arg Asp Glu Asn Pro Lys
945                 950                 955                 960

Asp Leu Asp Lys Val Ala Leu Thr Val Leu Ser His Ser Lys Val Ser
                965                 970                 975

Ala Lys Asn Asn Leu Ile Leu Ala Ile Leu Lys His Tyr Gln Pro Leu
            980                 985                 990

Cys Lys Leu Ser Ser Lys Val Ser Ala Ile Phe Ser Thr Pro Leu Gln
        995                 1000                1005

His Ile Val Glu Leu Glu Ser Lys Ala Thr Ala Lys Val Ala Leu
    1010                1015                1020

Gln Ala Arg Glu Ile Leu Ile Gln Gly Ala Leu Pro Ser Val Lys
    1025                1030                1035

Glu Arg Thr Glu Gln Ile Glu His Ile Leu Lys Ser Ser Val Val
    1040                1045                1050

Lys Val Ala Tyr Gly Ser Ser Asn Pro Lys Arg Ser Glu Pro Asp
    1055                1060                1065

Leu Asn Ile Leu Lys Asp Leu Ile Asp Ser Asn Tyr Val Val Phe
    1070                1075                1080

Asp Val Leu Leu Gln Phe Leu Thr His Gln Asp Pro Val Val Thr
    1085                1090                1095
```

-continued

Ala Ala Ala Ala Gln Val Tyr Ile Arg Arg Ala Tyr Arg Ala Tyr
1100                1105                1110

Thr Ile Gly Asp Ile Arg Val His Glu Gly Val Thr Val Pro Ile
1115                1120                1125

Val Glu Trp Lys Phe Gln Leu Pro Ser Ala Ala Phe Ser Thr Phe
1130                1135                1140

Pro Thr Val Lys Ser Lys Met Gly Met Asn Arg Ala Val Ser Val
1145                1150                1155

Ser Asp Leu Ser Tyr Val Ala Asn Ser Gln Ser Ser Pro Leu Arg
1160                1165                1170

Glu Gly Ile Leu Met Ala Val Asp His Leu Asp Asp Val Asp Glu
1175                1180                1185

Ile Leu Ser Gln Ser Leu Glu Val Ile Pro Arg His Gln Ser Ser
1190                1195                1200

Ser Asn Gly Pro Ala Pro Asp Arg Ser Gly Ser Ser Ala Ser Leu
1205                1210                1215

Ser Asn Val Ala Asn Val Cys Val Ala Ser Thr Glu Gly Phe Glu
1220                1225                1230

Ser Glu Glu Glu Ile Leu Val Arg Leu Arg Glu Ile Leu Asp Leu
1235                1240                1245

Asn Lys Gln Glu Leu Ile Asn Ala Ser Ile Arg Arg Ile Thr Phe
1250                1255                1260

Met Phe Gly Phe Lys Asp Gly Ser Tyr Pro Lys Tyr Tyr Thr Phe
1265                1270                1275

Asn Gly Pro Asn Tyr Asn Glu Asn Glu Thr Ile Arg His Ile Glu
1280                1285                1290

Pro Ala Leu Ala Phe Gln Leu Glu Leu Gly Arg Leu Ser Asn Phe
1295                1300                1305

Asn Ile Lys Pro Ile Phe Thr Asp Asn Arg Asn Ile His Val Tyr
1310                1315                1320

Glu Ala Val Ser Lys Thr Ser Pro Leu Asp Lys Arg Phe Phe Thr
1325                1330                1335

Arg Gly Ile Ile Arg Thr Gly His Ile Arg Asp Asp Ile Ser Ile
1340                1345                1350

Gln Glu Tyr Leu Thr Ser Glu Ala Asn Arg Leu Met Ser Asp Ile
1355                1360                1365

Leu Asp Asn Leu Glu Val Thr Asp Thr Ser Asn Ser Asp Leu Asn
1370                1375                1380

His Ile Phe Ile Asn Phe Ile Ala Val Phe Asp Ile Ser Pro Glu
1385                1390                1395

Asp Val Glu Ala Ala Phe Gly Gly Phe Leu Glu Arg Phe Gly Lys
1400                1405                1410

Arg Leu Leu Arg Leu Arg Val Ser Ser Ala Glu Ile Arg Ile Ile
1415                1420                1425

Ile Lys Asp Pro Gln Thr Gly Ala Pro Val Pro Leu Arg Ala Leu
1430                1435                1440

Ile Asn Asn Val Ser Gly Tyr Val Ile Lys Thr Glu Met Tyr Thr
1445                1450                1455

Glu Val Lys Asn Ala Lys Gly Glu Trp Val Phe Lys Ser Leu Gly
1460                1465                1470

Lys Pro Gly Ser Met His Leu Arg Pro Ile Ala Thr Pro Tyr Pro
1475                1480                1485

Val Lys Glu Trp Leu Gln Pro Lys Arg Tyr Lys Ala His Leu Met

-continued

```
            1490                1495                1500
Gly Thr Thr Tyr Val Tyr Asp Phe Pro Glu Leu Phe Arg Gln Ala
            1505                1510                1515
Ser Ser Ser Gln Trp Lys Asn Phe Ser Ala Asp Val Lys Leu Thr
            1520                1525                1530
Asp Asp Phe Phe Ile Ser Asn Glu Leu Ile Glu Asp Glu Asn Gly
            1535                1540                1545
Glu Leu Thr Glu Val Glu Arg Glu Pro Gly Ala Asn Ala Ile Gly
            1550                1555                1560
Met Val Ala Phe Lys Ile Thr Val Lys Thr Pro Glu Tyr Pro Arg
            1565                1570                1575
Gly Arg Gln Phe Val Val Ala Asn Asp Ile Thr Phe Lys Ile
            1580                1585                1590
Gly Ser Phe Gly Pro Gln Asp Glu Phe Phe Asn Lys Val Thr
            1595                1600                1605
Glu Tyr Ala Arg Lys Arg Gly Ile Pro Arg Ile Tyr Leu Ala Ala
            1610                1615                1620
Asn Ser Gly Ala Arg Ile Gly Met Ala Glu Glu Ile Val Pro Leu
            1625                1630                1635
Phe Gln Val Ala Trp Asn Asp Ala Ala Asn Pro Asp Lys Gly Phe
            1640                1645                1650
Gln Tyr Leu Tyr Leu Thr Ser Glu Gly Met Glu Thr Leu Lys Lys
            1655                1660                1665
Phe Asp Lys Glu Asn Ser Val Leu Thr Glu Arg Thr Val Ile Asn
            1670                1675                1680
Gly Glu Glu Arg Phe Val Ile Lys Thr Ile Ile Gly Ser Glu Asp
            1685                1690                1695
Gly Leu Gly Val Glu Cys Leu Arg Gly Ser Gly Leu Ile Ala Gly
            1700                1705                1710
Ala Thr Ser Arg Ala Tyr His Asp Ile Phe Thr Ile Thr Leu Val
            1715                1720                1725
Thr Cys Arg Ser Val Gly Ile Gly Ala Tyr Leu Val Arg Leu Gly
            1730                1735                1740
Gln Arg Ala Ile Gln Val Glu Gly Gln Pro Ile Ile Leu Thr Gly
            1745                1750                1755
Ala Pro Ala Ile Asn Lys Met Leu Gly Arg Glu Val Tyr Thr Ser
            1760                1765                1770
Asn Leu Gln Leu Gly Gly Thr Gln Ile Met Tyr Asn Asn Gly Val
            1775                1780                1785
Ser His Leu Thr Ala Val Asp Asp Leu Ala Gly Val Glu Lys Ile
            1790                1795                1800
Val Glu Trp Met Ser Tyr Val Pro Ala Lys Arg Asn Met Pro Val
            1805                1810                1815
Pro Ile Leu Glu Thr Lys Asp Thr Trp Asp Arg Pro Val Asp Phe
            1820                1825                1830
Thr Pro Thr Asn Asp Glu Thr Tyr Asp Val Arg Trp Met Ile Glu
            1835                1840                1845
Gly Arg Glu Thr Glu Ser Gly Phe Glu Tyr Gly Leu Phe Asp Lys
            1850                1855                1860
Gly Ser Phe Phe Glu Thr Leu Ser Gly Trp Ala Lys Gly Val Val
            1865                1870                1875
Val Gly Arg Ala Arg Leu Gly Gly Ile Pro Leu Gly Val Ile Gly
            1880                1885                1890
```

Val Glu Thr Arg Thr Val Glu Asn Leu Ile Pro Ala Asp Pro Ala
    1895                1900                1905

Asn Pro Asn Ser Ala Glu Thr Leu Ile Gln Glu Pro Gly Gln Val
    1910                1915                1920

Trp His Pro Asn Ser Ala Phe Lys Thr Ala Gln Ala Ile Asn Asp
    1925                1930                1935

Phe Asn Asn Gly Glu Gln Leu Pro Met Met Ile Leu Ala Asn Trp
    1940                1945                1950

Arg Gly Phe Ser Gly Gly Gln Arg Asp Met Phe Asn Glu Val Leu
    1955                1960                1965

Lys Tyr Gly Ser Phe Ile Val Asp Ala Leu Val Asp Tyr Lys Gln
    1970                1975                1980

Pro Ile Ile Ile Tyr Ile Pro Pro Thr Gly Glu Leu Arg Gly Gly
    1985                1990                1995

Ser Trp Val Val Val Asp Pro Thr Ile Asn Ala Asp Gln Met Glu
    2000                2005                2010

Met Tyr Ala Asp Val Asn Ala Arg Ala Gly Val Leu Glu Pro Gln
    2015                2020                2025

Gly Met Val Gly Ile Lys Phe Arg Arg Glu Lys Leu Leu Asp Thr
    2030                2035                2040

Met Asn Arg Leu Asp Asp Lys Tyr Arg Glu Leu Arg Ser Gln Leu
    2045                2050                2055

Ser Asn Lys Ser Leu Ala Pro Glu Val His Gln Gln Ile Ser Lys
    2060                2065                2070

Gln Leu Ala Asp Arg Glu Arg Glu Leu Leu Pro Ile Tyr Gly Gln
    2075                2080                2085

Ile Ser Leu Gln Phe Ala Asp Leu His Asp Arg Ser Ser Arg Met
    2090                2095                2100

Val Ala Lys Gly Val Ile Ser Lys Glu Leu Glu Trp Thr Glu Ala
    2105                2110                2115

Arg Arg Phe Phe Phe Trp Arg Leu Arg Arg Arg Leu Asn Glu Glu
    2120                2125                2130

Tyr Leu Ile Lys Arg Leu Ser His Gln Val Gly Glu Ala Ser Arg
    2135                2140                2145

Leu Glu Lys Ile Ala Arg Ile Arg Ser Trp Tyr Pro Ala Ser Val
    2150                2155                2160

Asp His Glu Asp Asp Arg Gln Val Ala Thr Trp Ile Glu Glu Asn
    2165                2170                2175

Tyr Lys Thr Leu Asp Asp Lys Leu Lys Gly Leu Lys Leu Glu Ser
    2180                2185                2190

Phe Ala Gln Asp Leu Ala Lys Lys Ile Arg Ser Asp His Asp Asn
    2195                2200                2205

Ala Ile Asp Gly Leu Ser Glu Val Ile Lys Met Leu Ser Thr Asp
    2210                2215                2220

Asp Lys Glu Lys Leu Leu Lys Thr Leu Lys
    2225                2230

<210> SEQ ID NO 35
<211> LENGTH: 2123
<212> TYPE: PRT
<213> ORGANISM: Saccharomyces cerevisiae
<220> FEATURE:
<223> OTHER INFORMATION: Saccharomyces cerevisiae mitochondrial ACC

<400> SEQUENCE: 35

```
Met Arg Ser Ile Arg Lys Trp Ala Tyr Glu Thr Phe Asn Asp Glu Lys
1               5                   10                  15

Ile Ile Gln Phe Val Val Met Ala Thr Pro Asp Leu His Ala Asn
            20                  25                  30

Ser Glu Tyr Ile Arg Met Ala Asp Gln Tyr Val Gln Val Pro Gly Gly
            35                  40                  45

Thr Asn Asn Asn Tyr Ala Asn Ile Asp Leu Ile Leu Asp Val Ala
    50                  55                  60

Glu Gln Thr Asp Val Asp Ala Val Trp Ala Gly Trp Gly His Ala Ser
65                  70                  75                  80

Glu Asn Pro Cys Leu Pro Glu Leu Leu Ala Ser Ser Gln Arg Lys Ile
                85                  90                  95

Leu Phe Ile Gly Pro Pro Gly Arg Ala Met Arg Ser Leu Gly Asp Lys
                100                 105                 110

Ile Ser Ser Thr Ile Val Ala Gln Ser Ala Lys Ile Pro Cys Ile Pro
            115                 120                 125

Trp Ser Gly Ser His Ile Asp Thr Ile His Ile Asp Asn Lys Thr Asn
130                 135                 140

Phe Val Ser Val Pro Asp Asp Val Tyr Val Arg Gly Cys Cys Ser Ser
145                 150                 155                 160

Pro Glu Asp Ala Leu Glu Lys Ala Lys Leu Ile Gly Phe Pro Val Met
                165                 170                 175

Ile Lys Ala Ser Glu Gly Gly Gly Gly Lys Gly Ile Arg Arg Val Asp
                180                 185                 190

Asn Glu Asp Asp Phe Ile Ala Leu Tyr Arg Gln Ala Val Asn Glu Thr
            195                 200                 205

Pro Gly Ser Pro Met Phe Val Met Lys Val Val Thr Asp Ala Arg His
210                 215                 220

Leu Glu Val Gln Leu Leu Ala Asp Gln Tyr Gly Thr Asn Ile Thr Leu
225                 230                 235                 240

Phe Gly Arg Asp Cys Ser Ile Gln Arg Arg His Gln Lys Ile Ile Glu
                245                 250                 255

Glu Ala Pro Val Thr Ile Thr Lys Pro Glu Thr Phe Gln Arg Met Glu
                260                 265                 270

Arg Ala Ala Ile Arg Leu Gly Glu Leu Val Gly Tyr Val Ser Ala Gly
            275                 280                 285

Thr Val Glu Tyr Leu Tyr Ser Pro Lys Asp Asp Lys Phe Tyr Phe Leu
            290                 295                 300

Glu Leu Asn Pro Arg Leu Gln Val Glu His Pro Thr Thr Glu Met Ile
305                 310                 315                 320

Ser Gly Val Asn Leu Pro Ala Thr Gln Leu Gln Ile Ala Met Gly Ile
                325                 330                 335

Pro Met His Met Ile Ser Asp Ile Arg Lys Leu Tyr Gly Leu Asp Pro
                340                 345                 350

Thr Gly Thr Ser Tyr Ile Asp Phe Lys Asn Leu Lys Arg Pro Ser Pro
            355                 360                 365

Lys Gly His Cys Ile Ser Cys Arg Ile Thr Ser Glu Asp Pro Asn Glu
            370                 375                 380

Gly Phe Lys Pro Ser Thr Gly Lys Ile His Glu Leu Asn Phe Arg Ser
385                 390                 395                 400

Ser Ser Asn Val Trp Gly Tyr Phe Ser Val Gly Asn Asn Gly Ala Ile
                405                 410                 415
```

```
His Ser Phe Ser Asp Ser Gln Phe Gly His Ile Phe Ala Val Gly Asn
            420                 425                 430

Asp Arg Gln Asp Ala Lys Gln Asn Met Val Leu Ala Leu Lys Asp Phe
        435                 440                 445

Ser Ile Arg Gly Glu Phe Lys Thr Pro Ile Glu Tyr Leu Ile Glu Leu
    450                 455                 460

Leu Glu Thr Arg Asp Phe Glu Ser Asn Asn Ile Ser Thr Gly Trp Leu
465                 470                 475                 480

Asp Asp Leu Ile Leu Lys Asn Leu Ser Ser Asp Ser Lys Leu Asp Pro
                485                 490                 495

Thr Leu Ala Ile Ile Cys Gly Ala Ala Met Lys Ala Tyr Val Phe Thr
            500                 505                 510

Glu Lys Val Arg Asn Lys Tyr Leu Glu Leu Leu Arg Arg Gly Gln Val
        515                 520                 525

Pro Pro Lys Asp Phe Leu Lys Thr Lys Phe Pro Val Asp Phe Ile Phe
    530                 535                 540

Asp Asn Asn Arg Tyr Leu Phe Asn Val Ala Gln Ser Ser Glu Glu Gln
545                 550                 555                 560

Phe Ile Leu Ser Ile Asn Lys Ser Gln Cys Glu Val Asn Val Gln Lys
                565                 570                 575

Leu Ser Ser Asp Cys Leu Leu Ile Ser Val Asp Gly Lys Cys His Thr
            580                 585                 590

Val Tyr Trp Lys Asp Asp Ile Arg Gly Thr Arg Leu Ser Ile Asp Ser
        595                 600                 605

Asn Thr Ile Phe Leu Glu Ala Glu Leu Asn Pro Thr Gln Val Ile Ser
    610                 615                 620

Pro Thr Pro Gly Lys Leu Val Lys Tyr Leu Val Arg Ser Gly Asp His
625                 630                 635                 640

Val Phe Ala Gly Gln Gln Tyr Ala Glu Ile Glu Ile Met Lys Met Gln
                645                 650                 655

Met Pro Leu Val Ala Lys Ser Asp Gly Val Ile Glu Leu Leu Arg Gln
            660                 665                 670

Pro Gly Ser Ile Ile Glu Ala Gly Asp Val Ile Ala Lys Leu Thr Leu
        675                 680                 685

Asp Ser Pro Ser Lys Ala Asn Glu Ser Ser Leu Tyr Arg Gly Glu Leu
    690                 695                 700

Pro Val Leu Gly Pro Pro Leu Ile Glu Gly Ser Arg Pro Asn His Lys
705                 710                 715                 720

Leu Arg Val Leu Ile Asn Arg Leu Glu Asn Ile Leu Asn Gly Tyr His
                725                 730                 735

Glu Asn Ser Gly Ile Glu Thr Thr Leu Lys Glu Leu Ile Lys Ile Leu
            740                 745                 750

Arg Asp Gly Arg Leu Pro Tyr Ser Glu Trp Asp Ser Gln Ile Ser Thr
        755                 760                 765

Val Arg Asn Arg Leu Pro Arg Gln Leu Asn Glu Gly Leu Gly Asn Leu
    770                 775                 780

Val Lys Lys Ser Val Ser Phe Pro Ala Lys Glu Leu His Lys Leu Met
785                 790                 795                 800

Lys Arg Tyr Leu Glu Glu Asn Thr Asn Asp His Val Val Tyr Val Ala
                805                 810                 815

Leu Gln Pro Leu Leu Lys Ile Ser Glu Arg Tyr Ser Glu Gly Leu Ala
            820                 825                 830

Asn His Glu Cys Glu Ile Phe Leu Lys Leu Ile Lys Lys Tyr Tyr Ala
```

```
                835              840              845
Val Glu Lys Ile Phe Glu Asn His Asp Ile His Glu Arg Asn Leu
850              855              860

Leu Asn Leu Arg Arg Lys Asp Leu Thr Asn Leu Lys Lys Ile Leu Cys
865              870              875              880

Ile Ser Leu Ser His Ala Asn Val Val Ala Lys Asn Lys Leu Val Thr
                885              890              895

Ala Ile Leu His Glu Tyr Glu Pro Leu Cys Gln Asp Ser Ser Lys Met
                900              905              910

Ser Leu Lys Phe Arg Ala Val Ile His Asp Leu Ala Ser Leu Glu Ser
                915              920              925

Lys Trp Ala Lys Glu Val Ala Val Lys Ala Arg Ser Val Leu Leu Arg
                930              935              940

Gly Ile Phe Pro Pro Ile Lys Lys Arg Lys Glu His Ile Lys Thr Leu
945              950              955              960

Leu Gln Leu His Ile Lys Asp Thr Gly Ala Glu Asn Ile His Ser Arg
                965              970              975

Asn Ile Tyr Ser Cys Met Arg Asp Phe Gly Asn Leu Ile His Ser Asn
                980              985              990

Leu Ile Gln Leu Gln Asp Leu Phe  Phe Phe Phe Gly His  Gln Asp Thr
                995              1000              1005

Ala Leu Ser Ser Ile Ala Ser  Glu Ile Tyr Ala Arg  Tyr Ala Tyr
                1010              1015              1020

Gly Asn  Tyr Gln Leu Lys Ser  Ile Lys Ile His Lys  Gly Ala Pro
                1025              1030              1035

Asp Leu  Leu Met Ser Trp Gln  Phe Ser Ser Leu Arg  Asn Tyr Leu
                1040              1045              1050

Val Asn  Ser Asp Gly Glu Ser  Asp Glu Phe Thr Lys  Leu Ser Lys
                1055              1060              1065

Pro Pro  Ser Thr Ser Gly Lys  Ser Ser Ala Asn Ser  Phe Gly Leu
                1070              1075              1080

Leu Val  Asn Met Arg Ala Leu  Glu Ser Leu Glu Lys  Thr Leu Asp
                1085              1090              1095

Glu Val  Tyr Glu Gln Ile His  Ile Pro Glu Glu Arg  Leu Ser Ser
                1100              1105              1110

Gly Glu  Asn Ser Leu Ile Val  Asn Ile Leu Ser Pro  Ile Arg Tyr
                1115              1120              1125

Arg Ser  Glu Asn Asp Leu Ile  Lys Thr Leu Lys Ile  Lys Leu His
                1130              1135              1140

Glu Asn  Glu Arg Gly Leu Ser  Lys Leu Lys Val Asn  Arg Ile Thr
                1145              1150              1155

Phe Ala  Phe Ile Ala Ala Asn  Ala Pro Ala Val Lys  Phe Tyr Ser
                1160              1165              1170

Phe Asp  Gly Thr Thr Tyr Asp  Glu Ile Ser Gln Ile  Arg Asn Met
                1175              1180              1185

Asp Pro  Ser Tyr Glu Ala Pro  Leu Glu Leu Gly Lys  Met Ser Asn
                1190              1195              1200

Tyr Lys  Ile Arg Ser Leu Pro  Thr Tyr Asp Ser Ser  Ile Arg Ile
                1205              1210              1215

Phe Glu  Gly Ile Ser Lys Phe  Thr Pro Leu Asp Lys  Arg Phe Phe
                1220              1225              1230

Val Arg  Lys Ile Ile Asn Ser  Phe Met Tyr Asn Asp  Gln Lys Thr
                1235              1240              1245
```

```
Thr Glu Glu Asn Leu Lys Ala Glu Ile Asn Ala Gln Val Val Tyr
    1250            1255            1260

Met Leu Glu His Leu Gly Ala Val Asp Ile Ser Asn Ser Asp Leu
    1265            1270            1275

Asn His Ile Phe Leu Ser Phe Asn Thr Val Leu Asn Ile Pro Val
    1280            1285            1290

His Arg Leu Glu Glu Ile Val Ser Thr Ile Leu Lys Thr His Glu
    1295            1300            1305

Thr Arg Leu Phe Gln Glu Arg Ile Thr Asp Val Glu Ile Cys Ile
    1310            1315            1320

Ser Val Glu Cys Leu Glu Thr Lys Lys Pro Ala Pro Leu Arg Leu
    1325            1330            1335

Leu Ile Ser Asn Lys Ser Gly Tyr Val Val Lys Ile Glu Thr Tyr
    1340            1345            1350

Tyr Glu Lys Ile Gly Lys Asn Gly Asn Leu Ile Leu Glu Pro Cys
    1355            1360            1365

Ser Glu Gln Ser His Tyr Ser Gln Lys Ser Leu Ser Leu Pro Tyr
    1370            1375            1380

Ser Val Lys Asp Trp Leu Gln Pro Lys Arg Tyr Lys Ala Gln Phe
    1385            1390            1395

Met Gly Thr Thr Tyr Val Tyr Asp Phe Pro Gly Leu Phe His Gln
    1400            1405            1410

Ala Ala Ile Gln Gln Trp Lys Arg Tyr Phe Pro Lys His Lys Leu
    1415            1420            1425

Asn Asp Ser Phe Phe Ser Trp Val Glu Leu Ile Glu Gln Asn Gly
    1430            1435            1440

Asn Leu Ile Lys Val Asn Arg Glu Pro Gly Leu Asn Asn Ile Gly
    1445            1450            1455

Met Val Ala Phe Glu Ile Met Val Gln Thr Pro Glu Tyr Pro Glu
    1460            1465            1470

Gly Arg Asn Met Ile Val Ile Ser Asn Asp Ile Thr Tyr Asn Ile
    1475            1480            1485

Gly Ser Phe Gly Pro Arg Glu Asp Leu Phe Phe Asp Arg Val Thr
    1490            1495            1500

Asn Tyr Ala Arg Glu Arg Gly Ile Pro Arg Ile Tyr Leu Ala Ala
    1505            1510            1515

Asn Ser Gly Ala Lys Leu Gly Ile Ala Glu Glu Leu Ile Pro Leu
    1520            1525            1530

Phe Arg Val Ala Trp Asn Asp Pro Ser Asp Pro Thr Lys Gly Phe
    1535            1540            1545

Gln Tyr Leu Tyr Leu Ala Pro Lys Asp Met Gln Leu Leu Lys Asp
    1550            1555            1560

Ser Gly Lys Gly Asn Ser Val Val Val Glu His Lys Met Val Tyr
    1565            1570            1575

Gly Glu Glu Arg Tyr Ile Ile Lys Ala Ile Val Gly Phe Glu Glu
    1580            1585            1590

Gly Leu Gly Val Glu Cys Leu Gln Gly Ser Gly Leu Ile Ala Gly
    1595            1600            1605

Ala Thr Ser Lys Ala Tyr Arg Asp Ile Phe Thr Ile Thr Ala Val
    1610            1615            1620

Thr Cys Arg Ser Val Gly Ile Gly Ser Tyr Leu Val Arg Leu Gly
    1625            1630            1635
```

```
Gln Arg Thr Ile Gln Val Glu Asp Lys Pro Ile Ile Leu Thr Gly
1640                1645                1650

Ala Ser Ala Ile Asn Lys Val Leu Gly Thr Asp Ile Tyr Thr Ser
1655                1660                1665

Asn Leu Gln Ile Gly Gly Thr Gln Ile Met Tyr Lys Asn Gly Ile
1670                1675                1680

Ala His Leu Thr Ala Ser Asn Asp Met Lys Ala Ile Glu Lys Ile
1685                1690                1695

Met Thr Trp Leu Ser Tyr Val Pro Ala Lys Arg Asp Met Ser Pro
1700                1705                1710

Pro Leu Leu Glu Thr Met Asp Arg Trp Asp Arg Asp Val Asp Phe
1715                1720                1725

Lys Pro Ala Lys Gln Val Pro Tyr Glu Ala Arg Trp Leu Ile Glu
1730                1735                1740

Gly Lys Trp Asp Ser Asn Asn Phe Gln Ser Gly Leu Phe Asp
1745                1750                1755

Lys Asp Ser Phe Phe Glu Thr Leu Ser Gly Trp Ala Lys Gly Val
1760                1765                1770

Ile Val Gly Arg Ala Arg Leu Gly Gly Ile Pro Val Gly Val Ile
1775                1780                1785

Ala Val Glu Thr Lys Thr Ile Glu Glu Ile Ile Pro Ala Asp Pro
1790                1795                1800

Ala Asn Leu Asp Ser Ser Glu Phe Ser Val Lys Glu Ala Gly Gln
1805                1810                1815

Val Trp Tyr Pro Asn Ser Ala Phe Lys Thr Ala Gln Thr Ile Asn
1820                1825                1830

Asp Phe Asn Tyr Gly Glu Gln Leu Pro Leu Ile Ile Leu Ala Asn
1835                1840                1845

Trp Arg Gly Phe Ser Gly Gly Gln Arg Asp Met Tyr Asn Glu Val
1850                1855                1860

Leu Lys Tyr Gly Ser Phe Ile Val Asp Ala Leu Val Asp Tyr Lys
1865                1870                1875

Gln Pro Ile Leu Ile Tyr Ile Pro Pro Phe Gly Glu Leu Arg Gly
1880                1885                1890

Gly Ser Trp Val Val Ile Asp Pro Thr Ile Asn Pro Glu Gln Met
1895                1900                1905

Glu Met Tyr Ala Asp Val Glu Ser Arg Gly Gly Val Leu Glu Pro
1910                1915                1920

Asp Gly Val Val Ser Ile Lys Tyr Arg Lys Glu Lys Met Ile Glu
1925                1930                1935

Thr Met Ile Arg Leu Asp Ser Thr Tyr Gly His Leu Arg Arg Thr
1940                1945                1950

Leu Thr Glu Lys Lys Leu Ser Leu Glu Lys Gln Asn Asp Leu Thr
1955                1960                1965

Lys Arg Leu Lys Ile Arg Glu Arg Gln Leu Ile Pro Ile Tyr Asn
1970                1975                1980

Gln Ile Ser Ile Gln Phe Ala Asp Leu His Asp Arg Ser Thr Arg
1985                1990                1995

Met Leu Val Lys Gly Val Ile Arg Asn Glu Leu Glu Trp Lys Lys
2000                2005                2010

Ser Arg Arg Phe Leu Tyr Trp Arg Leu Arg Arg Leu Asn Glu
2015                2020                2025

Gly Gln Val Ile Lys Arg Leu Gln Lys Lys Thr Cys Asp Asn Lys
```

-continued

```
                    2030                2035                2040

Thr Lys Met Lys Tyr Asp Asp Leu Leu Lys Ile Val Gln Ser Trp
            2045                2050                2055

Tyr Asn Asp Leu Asp Val Asn Asp Asp Arg Ala Val Val Glu Phe
        2060                2065                2070

Ile Glu Arg Asn Ser Lys Lys Ile Asp Lys Asn Ile Glu Glu Phe
        2075                2080                2085

Glu Ile Ser Leu Leu Ile Asp Glu Leu Lys Lys Phe Glu Asp
        2090                2095                2100

Arg Arg Gly Asn Ile Val Leu Glu Glu Leu Thr Arg Leu Val Asp
        2105                2110                2115

Ser Lys Arg Lys Arg
        2120

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      primer ACCExF-SpeI

<400> SEQUENCE: 36
atactagtat gactaccaac gtacagtcc                                          29

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer ACCExF-SpeI

<400> SEQUENCE: 37
ggactagtct taaacggtca tcgtggcg                                           28

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer ACC-F7

<400> SEQUENCE: 38
gcttggtcgc gatgtctaca cctcg                                              25

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      primer trpCt-R

<400> SEQUENCE: 39
acgtatctta tcgagatcct gaacacca                                           28

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
```

```
    oligonucleotide

<400> SEQUENCE: 40
tttttttttt tttttttttt tttttttttt                                    30
```